US011041169B2

(12) United States Patent
Nishida

(10) Patent No.: US 11,041,169 B2
(45) Date of Patent: Jun. 22, 2021

(54) METHOD FOR MODIFYING TARGET SITE IN DOUBLE-STRANDED DNA IN CELL

(71) Applicant: NATIONAL UNIVERSITY CORPORATION KOBE UNIVERSITY, Kobe (JP)

(72) Inventor: Keiji Nishida, Kobe (JP)

(73) Assignee: NATIONAL UNIVERSITY CORPORATION KOBE UNIVERSITY, Kobe (JP)

( * ) Notice: Subject to any disclaimer, the term of this patent is extended or adjusted under 35 U.S.C. 154(b) by 0 days.

(21) Appl. No.: 16/643,402

(22) PCT Filed: Mar. 26, 2019

(86) PCT No.: PCT/JP2019/012807

§ 371 (c)(1),
(2) Date: Feb. 28, 2020

(87) PCT Pub. No.: WO2019/189147

PCT Pub. Date: Oct. 3, 2019

(65) Prior Publication Data

US 2020/0270631 A1 Aug. 27, 2020

(30) Foreign Application Priority Data

Mar. 26, 2018 (JP) ............................ JP2018-059073

(51) Int. Cl.
*C12N 15/85* (2006.01)
*C12N 9/22* (2006.01)
*C12N 15/113* (2010.01)

(52) U.S. Cl.
CPC ............... *C12N 15/85* (2013.01); *C12N 9/22* (2013.01); *C12N 15/113* (2013.01); *C12N 2310/20* (2017.05); *C12N 2800/80* (2013.01)

(58) Field of Classification Search
None
See application file for complete search history.

(56) References Cited

U.S. PATENT DOCUMENTS

2015/0044772 A1 2/2015 Zhao
2017/0073670 A1* 3/2017 Nishida .......... C12Y 305/04005
2017/0121693 A1* 5/2017 Liu ......................... A61P 35/00
2017/0321210 A1 11/2017 Nishida et al.
2019/0024098 A1 1/2019 Nishida et al.
2019/0085342 A1 3/2019 Nishida et al.
2019/0203198 A1 7/2019 Mukoyama et al.

FOREIGN PATENT DOCUMENTS

CN 106459957 A 2/2017
EP 3636753 A1 5/2020
WO WO 2013/176772 A1 11/2013
WO WO 2015/133554 A1 9/2015
WO WO 2016/072399 A1 5/2016
WO WO 2017/043573 A1 3/2017
WO WO 2017/043656 A1 3/2017
WO WO 2017/053312 A1 3/2017
WO WO 2017/090761 A1 6/2017
WO WO 2018/230731 A1 12/2018

OTHER PUBLICATIONS

Kim et al. (2017) Increasing the genome-targeting scope and precision of base editing with engineered Cas9-cytidine deaminase fusions. Nature Biotechnology, 35(4):371-376 (Year: 2017).*
Koonin et al. (2017) Diversity, classification and evolution of CRISPR-Cas systems. Current Opinion in Microbiology, 37:67-78 (Year : 2017).*
Harrington et al. (2018) Programmed DNA destruction by miniature CRISPR-Cas14 enzymes. Science, 362:839-842 (Year: 2018).*
Ran et al. (2013) Double Nicking by RNA-Guided CRISPR Cas9 for Enhanced Genome Editing Specificity. Cell, 154:1380-1389 (Year: 2013).*
Kim et al. (2012) Overview of Base Excision Repair Biochemistry. Current Molecular Pharmacology, 5:3-13 (Year: 2012).*
Hendricks et al. (2002) the *S. cerevisiae* Mag1 3-methyladenine DNA glycosylase modulates susceptibility to homologous recombination. DNA Repair, 1:645-659 (Year: 2002).*
Cong et al., “Multiplex Genome Engineering Using CRISPR/Cas Systems”, *Science*, 339(6121): 819-823 and Supplementary Materials (Feb. 15, 2013).
Mali et al., “RNA-Guided Human Genome Engineering via Cas9”, *Science*, 339(6121): 823-826 and Supplementary Materials (Feb. 15, 2013).
Japanese Patent Office, International Search Report in International Patent Application No. PCT/JP2019/012807 (dated Jul. 2, 2019).
Japanese Patent Office, Written Opinion of the International Searching Authority in International Patent Application No. PCT/JP2019/012807 (dated Jul. 2, 2019).
Gaudelli et al., “Programmable base editing of A•T to G•C in genomic DNA without DNA cleavage,” *Nature*, 551(7681): 464-471 and Supplementary Information (2017) and Publisher Correction (2018).

(Continued)

*Primary Examiner* — Neil P Hammell
(74) *Attorney, Agent, or Firm* — Leydig, Voit & Mayer, Ltd.

(57) ABSTRACT

The present invention provides a method for modifying a targeted site of a double-stranded DNA in a cell, the method including a step of bringing a complex in which a nucleic acid sequence-recognizing module that specifically binds to a selected target nucleotide sequence in a double-stranded DNA and a nucleic acid base converting enzyme or DNA glycosylase are linked, and a donor DNA containing an insertion sequence into contact with said double-stranded DNA, to substitute the targeted site with the insertion sequence, or insert the insertion sequence into said targeted site, without cleaving at least one strand of said double-stranded DNA in the targeted site.

14 Claims, 12 Drawing Sheets

Specification includes a Sequence Listing.

(56) References Cited

OTHER PUBLICATIONS

Komor et al., "Editing the Genome Without Double-Stranded DNA Breaks," *ACS Chem. Biol.*, 13(2): 383-388 (2018).
Matsoukas, "Commentary: Programmable base editing of A•T to G•C in genomic DNA without DNA cleavage," *Front. Genet.* 9: 21 (2018).
Paquet et al., "Efficient introduction of specific homozygous and heterozygous mutations using CRISPR/Cas9," *Nature*, 553(7601): 125-129 and Supplementary Information (2016).
Shimatani et al., "Inheritance of co-edited genes by CRISPR-based targeted nucleotide substitutions in rice," *Plant Physiol. Biochem.*, 131: 78-83 (2018).
Komor et al., "Programmable editing of a target base in genomic DNA without double-stranded DNA cleavage," *Nature*, 533(7603): 420-424 and Online Content—Methods, Extended Data Figures 1-9, and Extended Data Table 1 (2016).
Ma et al., "Targeted AID-mediated mutagenesis (TAM) enables efficient genomic diversification in mammalian cells," *Nat. Methods*, 13(12): 1029-1035 and Online Methods (2016).
Nishida et al., "Targeted nucleotide editing using hybrid prokaryotic and vertebrate adaptive immune systems," *Science*, 353(6305): aaf8729 (2016).
Ran et al., "Genome engineering using the CRISPR-Cas9 system," *Nat. Protoc.*, 8(11): 2281-2308 (2013).
Brocken et al., "dCas9: a Versatile Tool for Epigenome Editing," *Curr. Issues Mol. Biol.*, 26: 15-32 (2018).

* cited by examiner

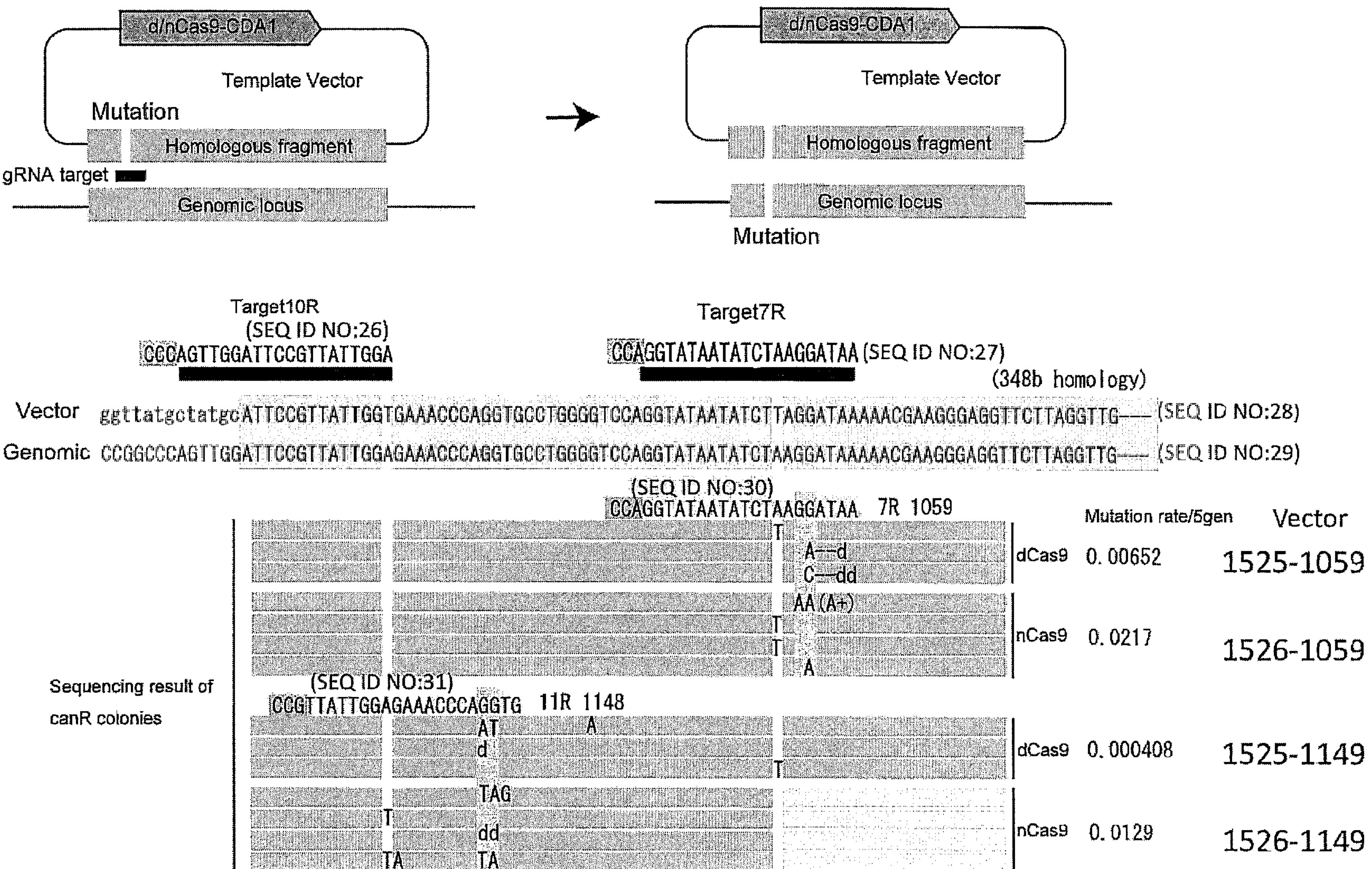

Fig 2
d/nCas9-CDA1
Template Vector
Mutation
Homologous fragment
gRNA target
Genomic locus
d/nCas9-CDA1
Template Vector
Homologous fragment
Genomic locus
Mutation
Target10R
(SEQ ID NO:26)
CGCAGTTGGATTCCGTTATTGGA
Target7R
CCAGGTATAATATCTAAGGATAA (SEQ ID NO:27)
(348b homology)
Vector ggttatgctatgcATTCCGTTATTGGTGAAACCCAGGTGCCTGGGGTCCAGGTATAATATCTTAGGATAAAAACGAAGGGAGGTTCTTAGGTTG--- (SEQ ID NO:28)
Genomic CCGGCCCAGTTGGATTCCGTTATTGGAGAAACCCAGGTGCCTGGGGTCCAGGTATAATATCTAAGGATAAAAACGAAGGGAGGTTCTTAGGTTG--- (SEQ ID NO:29)
(SEQ ID NO:30)
CCAGGTATAATATCTAAGGATAA 7R 1059
Mutation rate/5gen
Vector
T
A—d
C—dd
dCas9 0.00652
1525-1059
AA (A+)
T
T
A
nCas9 0.0217
1526-1059
Sequencing result of canR colonies
(SEQ ID NO:31)
CCGTTATTGGAGAAACCCAGGTG 11R 1148
AT
A
d
T
dCas9 0.000408
1525-1149
TAG
T
dd
TA
TA
nCas9 0.0129
1526-1149

Fig 6
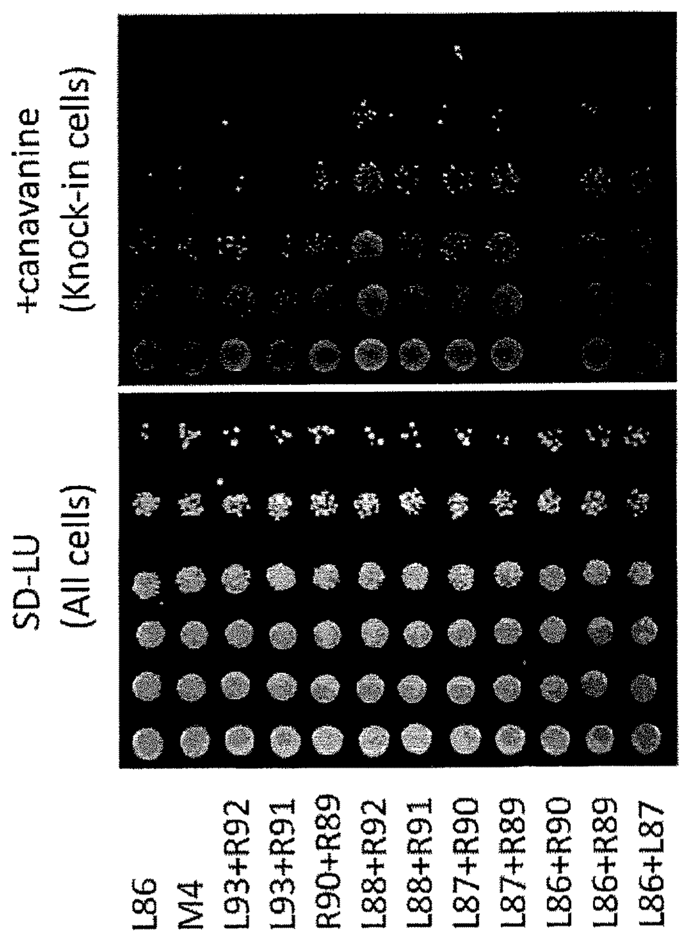
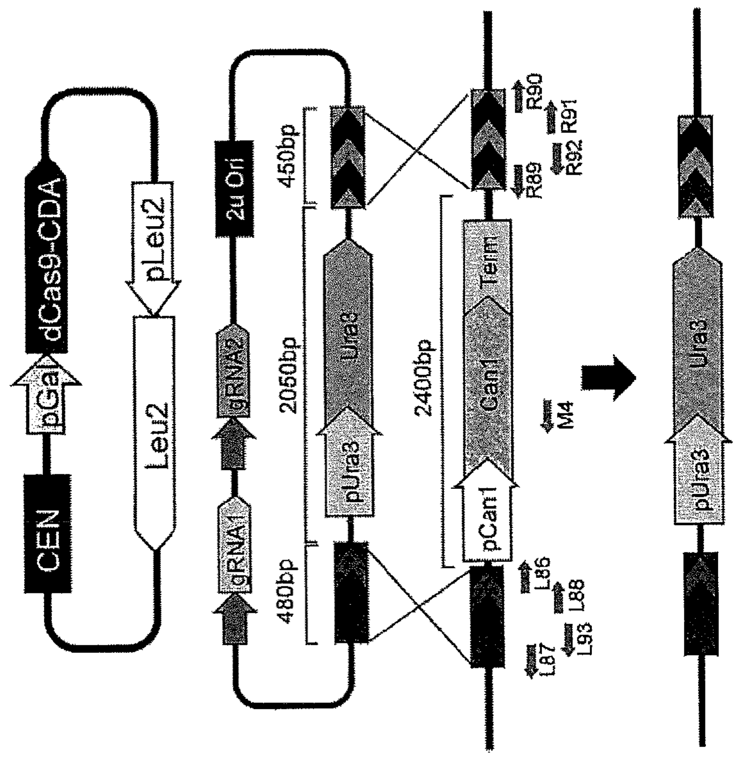

Cas9
AGGTG
TCCAC
CDA1
nCas9
dCas9
Fw1
Fw2
Fw3
AGATG
Oligo-Fw1
Oligo-Fw2
Oligo-Fw3
Normalized recombination efficiency
Cas9
Cas9-CDA1
nCas9
nCas9-CDA1
dCas9
dCas9-CDA1
0
1
2
3
4
5
6
EGFP+iRFP positive cell/iRFP positive cell (%)

A
nCas9
PmCDA1
EF1
D10A
H840A
NGGTG
NCCAC
deamination
Nick
70 bp
70 bp
70 bp
50 bp
70bp
EGFP+iRFP positive cell/iRFP positive cell (%)

SEQUENCE LISTING

```
<160> NUMBER OF SEQ ID NOS: 48

<210> SEQ ID NO 1
<211> LENGTH: 19
<212> TYPE: RNA
<213> ORGANISM: Francisella novicida
<220> FEATURE:
<221> NAME/KEY: misc_structure
<222> LOCATION: (1)..(19)
<223> OTHER INFORMATION: crRNA direct repeat sequence

<400> SEQUENCE: 1

aauuucuacu guuguagau                                                19


<210> SEQ ID NO 2
<211> LENGTH: 83
<212> TYPE: DNA
<213> ORGANISM: Streptococcus pyogenes
<220> FEATURE:
<221> NAME/KEY: misc_structure
<222> LOCATION: (1)..(83)
<223> OTHER INFORMATION: tracrRNA

<400> SEQUENCE: 2

gttttagagc tagaaatagc aagttaaaat aaggctagtc cgttatcaac ttgaaaaagt    60

ggcaccgagt cggtgctttt ttt                                            83


<210> SEQ ID NO 3
<211> LENGTH: 83
<212> TYPE: DNA
<213> ORGANISM: Streptococcus pyogenes
```

<220> FEATURE:
<221> NAME/KEY: misc_structure
<222> LOCATION: (1)..(83)
<223> OTHER INFORMATION: tracrRNA

<400> SEQUENCE: 3
gttttagagc tagaaatagc aagttaaaat aaggctagtc cgttatcaac ttgaaaaagt 60
ggcaccgagt cggtggtgct ttt 83

<210> SEQ ID NO 4
<211> LENGTH: 12344
<212> TYPE: DNA
<213> ORGANISM: Artificial Sequence
<220> FEATURE:
<223> OTHER INFORMATION: Synthetic Sequence - Plasmid Vector 1525(dCas9/nCas9-CDA)
<220> FEATURE:
<221> NAME/KEY: misc_structure
<222> LOCATION: (70)..(573)
<223> OTHER INFORMATION: CEN/ARS
<220> FEATURE:
<221> NAME/KEY: promoter
<222> LOCATION: (610)..(714)
<223> OTHER INFORMATION: AmpR pro
<220> FEATURE:
<221> NAME/KEY: rep_origin
<222> LOCATION: (1746)..(2334)
<223> OTHER INFORMATION: ori
<220> FEATURE:
<221> NAME/KEY: promoter
<222> LOCATION: (2852)..(3516)
<223> OTHER INFORMATION: GAL1,10 promoter
<220> FEATURE:
<221> NAME/KEY: misc_feature
<222> LOCATION: (3068)..(3185)
<223> OTHER INFORMATION: Gal4 UAS
<220> FEATURE:
<221> NAME/KEY: gene
<222> LOCATION: (3519)..(7655)
<223> OTHER INFORMATION: dCas9(D10A, H840A)/nCas9(D10A)
<220> FEATURE:
<221> NAME/KEY: mutation
<222> LOCATION: (3546)..(3548)
<223> OTHER INFORMATION: D10A
<220> FEATURE:
<221> NAME/KEY: mutation
<222> LOCATION: (6036)..(6038)
<223> OTHER INFORMATION: H840A or Wild Type
<220> FEATURE:
<221> NAME/KEY: misc_feature
<222> LOCATION: (7635)..(7655)
<223> OTHER INFORMATION: SV40 NLS
<220> FEATURE:
<221> NAME/KEY: misc_feature
<222> LOCATION: (7686)..(7856)
<223> OTHER INFORMATION: dead SH3
<220> FEATURE:
<221> NAME/KEY: misc_feature
<222> LOCATION: (7863)..(7928)
<223> OTHER INFORMATION: 3xFLAG
<220> FEATURE:
<221> NAME/KEY: gene
<222> LOCATION: (7935)..(8558)
<223> OTHER INFORMATION: PmCDA1
<220> FEATURE:
<221> NAME/KEY: terminator
<222> LOCATION: (8589)..(8776)
<223> OTHER INFORMATION: ADH1 terminator
<220> FEATURE:
<221> NAME/KEY: misc_feature
<222> LOCATION: (8862)..(9209)
<223> OTHER INFORMATION: CAN1(mut) fragment
<220> FEATURE:
<221> NAME/KEY: mutation
<222> LOCATION: (8875)..(8875)
<223> OTHER INFORMATION: Mutation 1

```
<220> FEATURE:
<221> NAME/KEY: mutation
<222> LOCATION: (8911)..(8911)
<223> OTHER INFORMATION: Mutation 2
<220> FEATURE:
<221> NAME/KEY: promoter
<222> LOCATION: (10171)..(10575)
<223> OTHER INFORMATION: S. cerevisiae LEU2 LEU2 prom
<220> FEATURE:
<221> NAME/KEY: gene
<222> LOCATION: (10588)..(11682)
<223> OTHER INFORMATION: S. cerevisiae LEU2

<400> SEQUENCE: 4

gacgaaaggg cctcgtgata cgcctatttt tataggttaa tgtcatgata ataatggttt     60

cttaggacgg atcgcttgcc tgtaacttac acgcgcctcg tatcttttaa tgatggaata    120

atttgggaat ttactctgtg tttatttatt tttatgtttt gtatttggat tttagaaagt    180

aaataaagaa ggtagaagag ttacggaatg aagaaaaaaa aataaacaaa ggtttaaaaa    240

atttcaacaa aaagcgtact ttacatatat atttattaga caagaaaagc agattaaata    300

gatatacatt cgattaacga taagtaaaat gtaaaatcac aggattttcg tgtgtggtct    360

tctacacaga caagatgaaa caattcggca ttaatacctg agagcaggaa gagcaagata    420

aaaggtagta tttgttggcg atccccctag agtcttttac atcttcggaa aacaaaaact    480

atttttttctt taatttcttt ttttactttc tatttttaat ttatatattt atattaaaaa    540

atttaaatta taattatttt tatagcacgt gatgaaaagg acccaggtgg cacttttcgg    600

ggaaatgtgc gcggaacccc tatttgttta tttttctaaa tacattcaaa tatgtatccg    660

ctcatgagac aataaccctg ataaatgctt caataatatt gaaaaaggaa gagtatgagt    720

attcaacatt tccgtgtcgc ccttattccc ttttttgcgg cattttgcct tcctgttttt    780

gctcacccag aaacgctggt gaaagtaaaa gatgctgaag atcagttggg tgcacgagtg    840

ggttacatcg aactggatct caacagcggt aagatccttg agagttttcg ccccgaagaa    900

cgttttccaa tgatgagcac ttttaaagtt ctgctatgtg gcgcggtatt atcccgtatt    960

gacgccgggc aagagcaact cggtcgccgc atacactatt ctcagaatga cttggttgag   1020

tactcaccag tcacagaaaa gcatcttacg gatggcatga cagtaagaga attatgcagt   1080

gctgccataa ccatgagtga taacactgcg gccaacttac ttctgacaac gatcggagga   1140

ccgaaggagc taaccgcttt tttgcacaac atgggggatc atgtaactcg ccttgatcgt   1200

tgggaaccgg agctgaatga agccatacca aacgacgagc gtgacaccac gatgcctgta   1260

gcaatggcaa caacgttgcg caaactatta actggcgaac tacttactct agcttcccgg   1320

caacaattaa tagactggat ggaggcggat aaagttgcag gaccacttct gcgctcggcc   1380

cttccggctg gctggtttat tgctgataaa tctggagccg gtgagcgtgg gtctcgcggt   1440

atcattgcag cactggggcc agatggtaag ccctcccgta tcgtagttat ctacacgacg   1500

ggcagtcagg caactatgga tgaacgaaat agacagatcg ctgagatagg tgcctcactg   1560

attaagcatt ggtaactgtc agaccaagtt tactcatata tactttagat tgatttaaaa   1620

cttcattttt aatttaaaag gatctaggtg aagatccttt ttgataatct catgaccaaa   1680

atcccttaac gtgagttttc gttccactga gcgtcagacc ccgtagaaaa gatcaaagga   1740

tcttcttgag atcctttttt tctgcgcgta atctgctgct tgcaaacaaa aaaaccaccg   1800

ctaccagcgg tggtttgttt gccggatcaa gagctaccaa ctctttttcc gaaggtaact   1860

ggcttcagca gagcgcagat accaaatact gtccttctag tgtagccgta gttaggccac   1920
```

```
cacttcaaga actctgtagc accgcctaca tacctcgctc tgctaatcct gttaccagtg   1980
gctgctgcca gtggcgataa gtcgtgtctt accgggttgg actcaagacg atagttaccg   2040
gataaggcgc agcggtcggg ctgaacgggg ggttcgtgca cacagcccag cttggagcga   2100
acgacctaca ccgaactgag atacctacag cgtgagcatt gagaaagcgc cacgcttccc   2160
gaagggagaa aggcggacag gtatccggta agcggcaggg tcggaacagg agagcgcacg   2220
agggagcttc caggggggaa cgcctggtat ctttatagtc ctgtcgggtt tcgccacctc   2280
tgacttgagc gtcgattttt gtgatgctcg tcaggggggc cgagcctatg gaaaaacgcc   2340
agcaacgcgg cctttttacg gttcctggcc ttttgctggc cttttgctca catgttcttt   2400
cctgcgttat cccctgattc tgtggataac cgtattaccg cctttgagtg agctgatacc   2460
gctcgccgca gccgaacgac cgagcgcagc gagtcagtga gcgaggaagc ggaagagcgc   2520
ccaatacgca aaccgcctct ccccgcgcgt tggccgattc attaatgcag ctggcacgac   2580
aggtttcccg actggaaagc gggcagtgag cgcaacgcaa ttaatgtgag ttagctcact   2640
cattaggcac cccaggcttt acactttatg cttccggctc gtatgttgtg tggaattgtg   2700
agcggataac aatttcacac aggaaacagc tatgaccatg attacgccaa gctcgaaatt   2760
aaccctcact aaagggaaca aaagctggta ccgggcccga attctctcct tctcttaggt   2820
ggcagagcag gtggagggtc gaccatacta gtttcaaaaa ttcttacttt tttttggat    2880
ggacgcaaag aagtttaata atcatattac atggcattac caccatatac atatccatat   2940
acatatccat atctaatctt acttatatgt tgtggaaatg taaagagccc cattatctta   3000
gcctaaaaaa accttctctt tggaactttc agtaatacgc ttaactgctc attgctatat   3060
tgaagtacgg attagaagcc gccgagcggg tgacagccct ccgaaggaag actctcctcc   3120
gtgcgtcctc gtcttcaccg gtcgcgttcc tgaaacgcag atgtgcctcg cgccgcactg   3180
ctccgaacaa taaagattct acaatactag cttttatggt tatgaagagg aaaaattggc   3240
agtaacctgg ccccacaaac cttcaaatga acgaatcaaa ttaacaacca taggatgata   3300
atgcgattag tttttagcc ttatttctgg ggtaattaat cagcgaagcg atgatttttg    3360
atctattaac agatatataa atgcaaaaac tgcataacca ctttaactaa tactttcaac   3420
attttcggtt tgtattactt cttattcaaa tgtaataaaa gtatcaacaa aaaattgtta   3480
atatacctct atactttaac gtcaaggaga aaaaacccat ggacaagaag tactccattg   3540
ggctcgctat cggcacaaac agcgtcggtt gggccgtcat tacggacgag tacaaggtgc   3600
cgagcaaaaa attcaaagtt ctgggcaata ccgatcgcca cagcataaag aagaacctca   3660
ttggcgccct cctgttcgac tccggggaga cggccgaagc cacgcggctc aaaagaacag   3720
cacggcgcag atatacccgc agaaagaatc ggatctgcta cctgcaggag atctttagta   3780
atgagatggc taaggtggat gactctttct tccataggct ggaggagtcc tttttggtgg   3840
aggaggataa aaagcacgag cgccacccaa tctttggcaa tatcgtggac gaggtggcgt   3900
accatgaaaa gtacccaacc atatatcatc tgaggaagaa gcttgtagac agtactgata   3960
aggctgactt gcggttgatc tatctcgcgc tggcgcatat gatcaaattt cggggacact   4020
tcctcatcga gggggacctg aacccagaca acagcgatgt cgacaaactc tttatccaac   4080
tggttcagac ttacaatcag cttttcgaag agaacccgat caacgcatcc ggagttgacg   4140
ccaaagcaat cctgagcgct aggctgtcca aatcccggcg gctcgaaaac ctcatcgcac   4200
agctccctgg ggagaagaag aacggcctgt ttggtaatct tatcgccctg tcactcgggc   4260
tgacccccaa ctttaaatct aacttcgacc tggccgaaga tgccaagctt caactgagca   4320
```

```
aagacaccta cgatgatgat ctcgacaatc tgctggccca gatcggcgac cagtacgcag   4380
accttttttt ggcggcaaag aacctgtcag acgccattct gctgagtgat attctgcgag   4440
tgaacacgga gatcaccaaa gctccgctga gcgctagtat gatcaagcgc tatgatgagc   4500
accaccaaga cttgactttg ctgaaggccc ttgtcagaca gcaactgcct gagaagtaca   4560
aggaaatttt cttcgatcag tctaaaaatg gctacgccgg atacattgac ggcggagcaa   4620
gccaggagga attttacaaa tttattaagc ccatcttgga aaaaatggac ggcaccgagg   4680
agctgctggt aaagcttaac agagaagatc tgttgcgcaa acagcgcact ttcgacaatg   4740
gaagcatccc ccaccagatt cacctgggcg aactgcacgc tatcctcagg cggcaagagg   4800
atttctaccc ctttttgaaa gataacaggg aaaagattga gaaaatcctc acatttcgga   4860
taccctacta tgtaggcccc ctcgcccggg gaaattccag attcgcgtgg atgactcgca   4920
aatcagaaga gaccatcact ccctggaact tcgaggaagt cgtggataag ggggcctctg   4980
cccagtcctt catcgaaagg atgactaact ttgataaaaa tctgcctaac gaaaaggtgc   5040
ttcctaaaca ctctctgctg tacgagtact tcacagttta taacgagctc accaaggtca   5100
aatacgtcac agaagggatg agaaagccag cattcctgtc tggagagcag aagaaagcta   5160
tcgtggacct cctcttcaag acgaaccgga aagttaccgt gaaacagctc aaagaagact   5220
atttcaaaaa gattgaatgt ttcgactctg ttgaaatcag cggagtggag gatcgcttca   5280
acgcatccct gggaacgtat cacgatctcc tgaaaatcat taaagacaag gacttcctgg   5340
acaatgagga gaacgaggac attcttgagg acattgtcct cacccttacg ttgtttgaag   5400
atagggagat gattgaagaa cgcttgaaaa cttacgctca tctcttcgac gacaaagtca   5460
tgaaacagct caagaggcgc cgatatacag gatgggggcg gctgtcaaga aaactgatca   5520
atgggatccg agacaagcag agtggaaaga caatcctgga ttttcttaag tccgatggat   5580
ttgccaaccg gaacttcatg cagttgatcc atgatgactc tctcaccttt aaggaggaca   5640
tccagaaagc acaagtttct ggccaggggg acagtcttca cgagcacatc gctaatcttg   5700
caggtagccc agctatcaaa aagggaatac tgcagaccgt taaggtcgtg gatgaactcg   5760
tcaaagtaat gggaaggcat aagcccgaga atatcgttat cgagatggcc cgagagaacc   5820
aaactaccca gaagggacag aagaacagta gggaaaggat gaagaggatt gaagagggta   5880
taaaagaact ggggtcccaa atccttaagg aacacccagt tgaaaacacc cagcttcaga   5940
atgagaagct ctacctgtac tacctgcaga acggcaggga catgtacgtg gatcaggaac   6000
tggacatcaa tcggctctcc gactacgacg tggatsmtat cgtgccccag tcttttctca   6060
aagatgattc tattgataat aaagtgttga caagatccga taaaaataga gggaagagtg   6120
ataacgtccc ctcagaagaa gttgtcaaga aaatgaaaaa ttattggcgg cagctgctga   6180
acgccaaact gatcacacaa cggaagttcg ataatctgac taaggctgaa cgaggtggcc   6240
tgtctgagtt ggataaagcc ggcttcatca aaaggcagct tgttgagaca cgccagatca   6300
ccaagcacgt ggcccaaatt ctcgattcac gcatgaacac caagtacgat gaaaatgaca   6360
aactgattcg agaggtgaaa gttattactc tgaagtctaa gctggtctca gatttcagaa   6420
aggactttca gttttataag gtgagagaga tcaacaatta ccaccatgcg catgatgcct   6480
acctgaatgc agtggtaggc actgcactta tcaaaaaata tcccaagctt gaatctgaat   6540
ttgtttacgg agactataaa gtgtacgatg ttaggaaaat gatcgcaaag tctgagcagg   6600
aaataggcaa ggccaccgct aagtacttct tttacagcaa tattatgaat tttttcaaga   6660
```

-continued

```
ccgagattac actggccaat ggagagattc ggaagcgacc acttatcgaa acaaacggag   6720
aaacaggaga aatcgtgtgg gacaagggta gggatttcgc gacagtccgg aaggtcctgt   6780
ccatgccgca ggtgaacatc gttaaaaaga ccgaagtaca gaccggaggc ttctccaagg   6840
aaagtatcct cccgaaaagg aacagcgaca agctgatcgc acgcaaaaaa gattgggacc   6900
ccaagaaata cggcggattc gattctccta cagtcgctta cagtgtactg gttgtggcca   6960
aagtggagaa agggaagtct aaaaaactca aaagcgtcaa ggaactgctg ggcatcacaa   7020
tcatggagcg atcaagcttc gaaaaaaacc ccatcgactt tctcgaggcg aaaggatata   7080
aagaggtcaa aaaagacctc atcattaagc ttcccaagta ctctctcttt gagcttgaaa   7140
acggccggaa acgaatgctc gctagtgcgg gcgagctgca gaaaggtaac gagctggcac   7200
tgccctctaa atacgttaat ttcttgtatc tggccagcca ctatgaaaag ctcaaagggt   7260
ctcccgaaga taatgagcag aagcagctgt tcgtggaaca acacaaacac taccttgatg   7320
agatcatcga gcaaataagc gaattctcca aaagagtgat cctcgccgac gctaacctcg   7380
ataaggtgct ttctgcttac aataagcaca gggataagcc catcagggag caggcagaaa   7440
acattatcca cttgtttact ctgaccaact tgggcgcgcc tgcagccttc aagtacttcg   7500
acaccaccat agacagaaag cggtacacct ctacaaagga ggtcctggac gccacactga   7560
ttcatcagtc aattacgggg ctctatgaaa caagaatcga cctctctcag ctcggtggag   7620
acagcagggc tgaccccaag aagaagagga aggtgggtgg aggaggttct ggaggtggag   7680
gttctgcaga gtatgtgcgg gccctctttg actttaatgg gaatgatgaa gaagatcttc   7740
cctttaagaa aggagacatc ctgagaatcc gggataagcc tgaagagcag tggtggaatg   7800
cagaggacag cgaaggaaag agggggatga ttcttgtccc ttacgtggag aagtattccg   7860
gagactataa ggaccacgac ggagactaca aggatcatga tattgattac aaagacgatg   7920
acgataagtc taggatgacc gacgctgagt acgtgagaat ccatgagaag ttggacatct   7980
acacgtttaa gaaacagttt ttcaacaaca aaaaatccgt gtcgcataga tgctacgttc   8040
tctttgaatt aaaacgacgg ggtgaacgta gagcgtgttt ttggggctat gctgtgaata   8100
aaccacagag cgggacagaa cgtggcattc acgccgaaat ctttagcatt agaaaagtcg   8160
aagaatacct gcgcgacaac cccggacaat tcacgataaa ttggtactca tcctggagtc   8220
cttgtgcaga ttgcgctgaa aagatcttag aatggtataa ccaggagctg cgggggaacg   8280
gccacacttt gaaaatctgg gcttgcaaac tctattacga gaaaaatgcg aggaatcaaa   8340
ttgggctgtg gaacctcaga gataacgggg ttgggttgaa tgtaatggta agtgaacact   8400
accaatgttg caggaaaata ttcatccaat cgtcgcacaa tcaattgaat gagaatagat   8460
ggcttgagaa gactttgaag cgagctgaaa aacgacggag cgagttgtcc attatgattc   8520
aggtaaaaat actccacacc actaagagtc ctgctgtttc tagaggctcc ggataaggat   8580
cctaataagc gaatttctta tgatttatga tttttattat taaataagtt ataaaaaaaa   8640
taagtgtata caaattttaa agtgactctt aggttttaaa acgaaaattc ttattcttga   8700
gtaactcttt cctgtaggtc aggttgcttt ctcaggtata gcatgaggtc gctcttattg   8760
accacacctc taccggcatg ccgagcaaat gcctgcaaat cgctccccgg caaaaaaccc   8820
cctcaagacc cgtttagagg ccccaagggg ttatgctatg cattccgtta ttggtgaaac   8880
ccaggtgcct ggggtccagg tataatatct taggataaaa acgaagggag gttcttaggt   8940
tgggtttcct ctttgattaa cgctgccttc acatttcaag gtactgaact agttggtatc   9000
actgctggtg aagctgcaaa ccccagaaaa tccgttccaa gagccatcaa aaaagttgtt   9060
```

```
ttccgtatct taaccttcta cattggctct ctattattca ttggactttt agttccatac   9120
aatgacccta aactaacaca atctacttcc tacgtttcta cttctccctt tattattgct   9180
attgagaact ctggtacaaa ggttttgccg cggtggagct ccaattcgcc ctatagtgag   9240
tcgtattaca attcactggc cgtcgtttta caacgtcgtg actgggaaaa ccctggcgtt   9300
acccaactta atcgccttgc agcacatccc ccttcgcca gctggcgtaa tagcgaagag    9360
gcccgcaccg atcgcccttc ccaacagttg cgcagcctga atggcgaatg gcgcgacgcg   9420
ccctgtagcg gcgcattaag cgcggcgggt gtggtggtta cgcgcagcgt gaccgctaca   9480
cttgccagcg ccctagcgcc cgctcctttc gctttcttcc cttcctttct cgccacgttc   9540
gccggctttc cccgtcaagc tctaaatcgg gggctccctt tagggttccg atttagtgct   9600
ttacggcacc tcgaccccaa aaaacttgat tagggtgatg gttcacgtag tgggccatcg   9660
ccctgataga cggtttttcg ccctttgacg ttggagtcca cgttctttaa tagtggactc   9720
ttgttccaaa ctggaacaac actcaaccct atctcggtct attcttttga tttataaggg   9780
attttgccga tttcggccta ttggttaaaa aatgagctga tttaacaaaa atttaacgcg   9840
aattttaaca aaatattaac gtttacaatt tcctgatgcg gtattttctc cttacgcatc   9900
tgtgcggtat ttcacaccgc atatcgaccc tcgaggagaa cttctagtat atccacatac   9960
ctaatattat tgccttatta aaaatggaat cggaacaatt acatcaaaat ccacattctc  10020
ttcaaaatca attgtcctgt acttccttgt tcatgtgtgt tcaaaaacgt tatatttata  10080
ggataattat actctatttc tcaacaagta attggttgtt tggccgagcg gtctaaggcg  10140
cctgattcaa gaaatatctt gaccgcagtt aactgtggga atactcaggt atcgtaagat  10200
gcaagagttc gaatctctta gcaaccatta ttttttcct caacataacg agaacacaca   10260
ggggcgctat cgcacagaat caaattcgat gactggaaat tttttgttaa tttcagaggt  10320
cgcctgacgc atatacettt ttcaactgaa aaattgggag aaaaaggaaa ggtgagaggc  10380
cggaaccggc ttttcatata gaatagagaa gcgttcatga ctaaatgctt gcatcacaat  10440
acttgaagtt gacaatatta tttaaggacc tattgttttt tccaataggt ggttagcaat  10500
cgtcttactt tctaactttt cttacctttt acatttcagc aatatatata tatatttcaa  10560
ggatatacca ttctaatgtc tgcccctatg tctgccccta agaagatcgt cgttttgcca  10620
ggtgaccacg ttggtcaaga aatcacagcc gaagccatta aggttcttaa agctatttct  10680
gatgttcgtt ccaatgtcaa gttcgatttc gaaaatcatt taattggtgg tgctgctatc  10740
gatgctacag gtgtcccact tccagatgag gcgctggaag cctccaagaa ggttgatgcc  10800
gttttgttag gtgctgtggg tggtcctaaa tggggtaccg gtagtgttag acctgaacaa  10860
ggtttactaa aaatccgtaa agaacttcaa ttgtacgcca acttaagacc atgtaacttt  10920
gcatccgact ctcttttaga cttatctcca atcaagccac aatttgctaa aggtactgac  10980
ttcgttgttg tcagagaatt agtgggaggt atttactttg gtaagagaaa ggaagacgat  11040
ggtgatggtg tcgcttggga tagtgaacaa tacaccgttc cagaagtgca aagaatcaca  11100
agaatggccg ctttcatggc cctacaacat gagccaccat tgcctatttg gtccttggat  11160
aaagctaatg ttttggcctc ttcaagatta tggagaaaaa ctgtggagga aaccatcaag  11220
aacgaattcc ctacattgaa ggttcaacat caattgattg attctgccgc catgatccta  11280
gttaagaacc caacccacct aaatggtatt ataatcacca gcaacatgtt tggtgatatc  11340
atctccgatg aagcctccgt tatcccaggt tccttgggtt tgttgccatc tgcgtccttg  11400
```

```
gcctctttgc cagacaagaa caccgcattt ggtttgtacg aaccatgcca cggttctgct  11460

ccagatttgc caaagaataa ggttgaccct atcgccacta tcttgtctgc tgcaatgatg  11520

ttgaaattgt cattgaactt gcctgaagaa ggtaaggcca ttgaagatgc agttaaaaag  11580

gttttggatg caggtatcag aactggtgat ttaggtggtt ccaacagtac caccgaagtc  11640

ggtgatgctg tcgccgaaga agttaagaaa atccttgctt aaaaagattc tcttttttta  11700

tgatatttgt acataaactt tataaatgaa attcataata gaaacgacac gaaattacaa  11760

aatggaatat gttcataggg tagacgaaac tatatacgca atctacatac atttatcaag  11820

aaggagaaaa aggaggatag taaaggaata caggtaagca aattgatact aatggctcaa  11880

cgtgataagg aaaaagaatt gcactttaac attaatattg acaaggagga gggcaccaca  11940

caaaaagtta ggtgtaacag aaaatcatga aactacgatt cctaatttga tattggagga  12000

ttttctctaa aaaaaaaaaa atacaacaaa taaaaaacac tcaatgacct gaccatttga  12060

tggagtttaa gtcaatacct tcttgaacca tttcccataa tggtgaaagt tccctcaaga  12120

attttactct gtcagaaacg gccttacgac gtagtcgata tggtgcactc tcagtacaat  12180

ctgctctgat gccgcatagt taagccagcc ccgacacccg ccaacacccg ctgacgcgcc  12240

ctgacgggct tgtctgctcc cggcatccgc ttacagacaa gctgtgaccg tctccgggag  12300

ctgcatgtgt cagaggtttt caccgtcatc accgaaacgc gcga                   12344
```

<210> SEQ ID NO 5
<211> LENGTH: 6274
<212> TYPE: DNA
<213> ORGANISM: Artificial Sequence
<220> FEATURE:
<223> OTHER INFORMATION: Synthetic Sequence - Plasmid Vector 1059(Can1-7R)
<220> FEATURE:
<221> NAME/KEY: rep_origin
<222> LOCATION: (69)..(1411)
<223> OTHER INFORMATION: 2 micro ori
<220> FEATURE:
<221> NAME/KEY: promoter
<222> LOCATION: (1438)..(1542)
<223> OTHER INFORMATION: AmpR promoter
<220> FEATURE:
<221> NAME/KEY: gene
<222> LOCATION: (1543)..(2403)
<220> FEATURE:
<221> NAME/KEY: rep_origin
<222> LOCATION: (2574)..(3162)
<223> OTHER INFORMATION: ori
<220> FEATURE:
<221> NAME/KEY: promoter
<222> LOCATION: (3621)..(3889)
<223> OTHER INFORMATION: SNR52 promoter
<220> FEATURE:
<221> NAME/KEY: misc_feature
<222> LOCATION: (3890)..(3909)
<223> OTHER INFORMATION: Can1-7R
<220> FEATURE:
<221> NAME/KEY: misc_structure
<222> LOCATION: (3910)..(3992)
<223> OTHER INFORMATION: tracrRNA
<220> FEATURE:
<221> NAME/KEY: terminator
<222> LOCATION: (3995)..(4008)
<223> OTHER INFORMATION: Sup4 term
<220> FEATURE:
<221> NAME/KEY: terminator
<222> LOCATION: (4014)..(4261)
<223> OTHER INFORMATION: CYC1 terminator
<220> FEATURE:
<221> NAME/KEY: promoter
<222> LOCATION: (4280)..(4298)
<223> OTHER INFORMATION: T7 promoter

```
<220> FEATURE:
<221> NAME/KEY: rep_origin
<222> LOCATION: (4469)..(4924)
<223> OTHER INFORMATION: f1 ori
<220> FEATURE:
<221> NAME/KEY: gene
<222> LOCATION: (5055)..(5858)
<223> OTHER INFORMATION: URA3
<220> FEATURE:
<221> NAME/KEY: promoter
<222> LOCATION: (5859)..(6074)
<223> OTHER INFORMATION: URA3 promoter

<400> SEQUENCE: 5

gacgaaaggg cctcgtgata cgcctatttt tataggttaa tgtcatgata ataatggttt     60

cttagtatga tccaatatca aaggaaatga tagcattgaa ggatgagact aatccaattg    120

aggagtggca gcatatagaa cagctaaagg gtagtgctga aggaagcata cgataccccg    180

catggaatgg gataatatca caggaggtac tagactacct ttcatcctac ataaatagac    240

gcatataagt acgcatttaa gcataaacac gcactatgcc gttcttctca tgtatatata    300

tatacaggca acacgcagat ataggtgcga cgtgaacagt gagctgtatg tgcgcagctc    360

gcgttgcatt ttcggaagcg ctcgttttcg gaaacgcttt gaagttccta ttccgaagtt    420

cctattctct agaaagtata ggaacttcag agcgcttttg aaaaccaaaa gcgctctgaa    480

gacgcacttt caaaaaacca aaaacgcacc ggactgtaac gagctactaa aatattgcga    540

ataccgcttc cacaaacatt gctcaaaagt atctctttgc tatatatctc tgtgctatat    600

ccctatataa cctacccatc cacctttcgc tccttgaact tgcatctaaa ctcgacctct    660

acatttttta tgtttatctc tagtattact ctttagacaa aaaaattgta gtaagaacta    720

ttcatagagt gaatcgaaaa caatacgaaa atgtaaacat ttcctatacg tagtatatag    780

agacaaaata gaagaaaccg ttcataattt tctgaccaat gaagaatcat caacgctatc    840

actttctgtt cacaaagtat gcgcaatcca catcggtata gaatataatc ggggatgcct    900

ttatcttgaa aaaatgcacc cgcagcttcg ctagtaatca gtaaacgcgg gaagtggagt    960

caggcttttt ttatggaaga gaaaatagac accaaagtag ccttcttcta accttaacgg   1020

acctacagtg caaaaagtta tcaagagact gcattataga gcgcacaaag gagaaaaaaa   1080

gtaatctaag atgctttgtt agaaaaatag cgctctcggg atgcattttt gtagaacaaa   1140

aaagaagtat agattctttg ttggtaaaat agcgctctcg cgttgcattt ctgttctgta   1200

aaaatgcagc tcagattctt tgtttgaaaa attagcgctc tcgcgttgca tttttgtttt   1260

acaaaaatga agcacagatt cttcgttggt aaaatagcgc tttcgcgttg catttctgtt   1320

ctgtaaaaat gcagctcaga ttctttgttt gaaaaattag cgctctcgcg ttgcattttt   1380

gttctacaaa atgaagcaca gatgcttcgt tcaggtggca cttttcgggg aaatgtgcgc   1440

ggaaccccta tttgtttatt tttctaaata cattcaaata tgtatccgct catgagacaa   1500

taaccctgat aaatgcttca ataatattga aaaaggaaga gtatgagtat tcaacatttc   1560

cgtgtcgccc ttattccctt ttttgcggca ttttgccttc ctgtttttgc tcacccagaa   1620

acgctggtga aagtaaaaga tgctgaagat cagttgggtg cacgagtggg ttacatcgaa   1680

ctggatctca acagcggtaa gatccttgag agttttcgcc ccgaagaacg ttttccaatg   1740

atgagcactt ttaaagttct gctatgtggc gcggtattat cccgtattga cgccgggcaa   1800

gagcaactcg gtcgccgcat acactattct cagaatgact tggttgagta ctcaccagtc   1860

acagaaaagc atcttacgga tggcatgaca gtaagagaat tatgcagtgc tgccataacc   1920
```

-continued

```
atgagtgata acactgcggc caacttactt ctgacaacga tcggaggacc gaaggagcta   1980
accgcttttt tgcacaacat gggggatcat gtaactcgcc ttgatcgttg ggaaccggag   2040
ctgaatgaag ccataccaaa cgacgagcgt gacaccacga tgcctgtagc aatggcaaca   2100
acgttgcgca aactattaac tggcgaacta cttactctag cttcccggca acaattaata   2160
gactggatgg aggcggataa agttgcagga ccacttctgc gctcggccct tccggctggc   2220
tggtttattg ctgataaatc tggagccggt gagcgtgggt ctcgcggtat cattgcagca   2280
ctggggccag atggtaagcc ctcccgtatc gtagttatct acacgacggg gagtcaggca   2340
actatggatg aacgaaatag acagatcgct gagataggtg cctcactgat taagcattgg   2400
taactgtcag accaagttta ctcatatata ctttagattg atttaaaact tcatttttaa   2460
tttaaaagga tctaggtgaa gatccttttt gataatctca tgaccaaaat cccttaacgt   2520
gagttttcgt tccactgagc gtcagacccc gtagaaaaga tcaaaggatc ttcttgagat   2580
cctttttttc tgcgcgtaat ctgctgcttg caaacaaaaa aaccaccgct accagcggtg   2640
gtttgtttgc cggatcaaga gctaccaact ctttttccga aggtaactgg cttcagcaga   2700
gcgcagatac caaatactgt ccttctagtg tagccgtagt taggccacca cttcaagaac   2760
tctgtagcac cgcctacata cctcgctctg ctaatcctgt taccagtggc tgctgccagt   2820
ggcgataagt cgtgtcttac cgggttggac tcaagacgat agttaccgga taaggcgcag   2880
cggtcgggct gaacgggggg ttcgtgcaca cagcccagct tggagcgaac gacctacacc   2940
gaactgagat acctacagcg tgagctatga gaaagcgcca cgcttcccga agggagaaag   3000
gcggacaggt atccggtaag cggcagggtc ggaacaggag agcgcacgag ggagcttcca   3060
gggggaaacg cctggtatct ttatagtcct gtcgggtttc gccacctctg acttgagcgt   3120
cgatttttgt gatgctcgtc aggggggcgg agcctatgga aaaacgccag caacgcggcc   3180
tttttacggt tcctggcctt ttgctggcct tttgctcaca tgttctttcc tgcgttatcc   3240
cctgattctg tggataaccg tattaccgcc tttgagtgag ctgataccgc tcgccgcagc   3300
cgaacgaccg agcgcagcga gtcagtgagc gaggaagcgg aagagcgccc aatacgcaaa   3360
ccgcctctcc ccgcgcgttg gccgattcat taatgcagct ggcacgacag gtttcccgac   3420
tggaaagcgg gcagtgagcg caacgcaatt aatgtgagtt acctcactca ttaggcaccc   3480
caggctttac actttatgct tccggctcct atgttgtgtg gaattgtgag cggataacaa   3540
tttcacacag gaaacagcta tgaccatgat tacgccaagc gcgcaattaa ccctcactaa   3600
agggaacaaa agctggagct tctttgaaaa gataatgtat gattatgctt tcactcatat   3660
ttatacagaa acttgatgtt ttctttcgag tatatacaag gtgattacat gtacgtttga   3720
agtacaactc tagattttgt agtgccctct tgggctagcg gtaaaggtgc gcattttttc   3780
acaccctaca atgttctgtt caaaagattt tggtcaaacg ctgtagaagt gaaagttggt   3840
gcgcatgttt cggcgttcga aacttctccg cagtgaaaga taaatgatct tatccttaga   3900
tattataccg ttttagagct agaaatagca agttaaaata aggctagtcc gttatcaact   3960
tgaaaaagtg gcaccgagtc ggtggtgctt tttttgtttt ttatgtcttc gagtcatgta   4020
attagttatg tcacgcttac gttcacgccc tccccccaca tccgctctaa ccgaaaagga   4080
aggagttaga caacctgaag tctaggtccc tatttatttt tttatagtta tgttagtatt   4140
aagaacgtta tttatatttc aaatttttct tttttttctg tacagacgcg tgtacgcatg   4200
taacattata ctgaaaacct tgcttgagaa ggttttggga cgctcgaagg ctttaatttg   4260
cggccggtac ccaattcgcc ctatagtgag tcgtattacg cgcgctcact ggccgtcgtt   4320
```

```
ttacaacgtc gtgactggga aaaccctggc gttacccaac ttaatcgcct tgcagcacat   4380
ccccctttcg ccagctggcg taatagcgaa gaggcccgca ccgatcgccc ttcccaacag   4440
ttgcgcagcc tgaatggcga atggcgcgac gcgccctgta gcggcgcatt aagcgcggcg   4500
ggtgtggtgg ttacgcgcag cgtgaccgct acacttgcca gcgccctagc gcccgctcct   4560
ttcgctttct tcccttcctt tctcgccacg ttcgccggct ttccccgtca agctctaaat   4620
cgggggctcc ctttagggtt ccgatttagt gctttacggc acctcgaccc caaaaaactt   4680
gattagggtg atggttcacg tagtgggcca tcgccctgat agacggtttt tcgccctttg   4740
acgttggagt ccacgttctt taatagtgga ctcttgttcc aaactggaac aacactcaac   4800
cctatctcgg tctattcttt tgatttataa gggattttgc cgatttcggc ctattggtta   4860
aaaaatgagc tgatttaaca aaaatttaac gcgaatttta acaaaatatt aacgtttaca   4920
atttcctgat gcggtatttt ctccttacgc atctgtgcgg tatttcacac cgcatagggt   4980
aataactgat ataattaaat tgaagctcta atttgtgagt ttagtataca tgcatttact   5040
tataatacag tttttagtt ttgctggccg catcttctca aatatgcttc ccagcctgct   5100
tttctgtaac gttcaccctc taccttagca tcccttccct ttgcaaatag tcctcttcca   5160
acaataataa tgtcagatcc tgtagagacc acatcatcca cggttctata ctgttgaccc   5220
aatgcgtctc ccttgtcatc taaacccaca ccgggtgtca taatcaacca atcgtaacct   5280
tcatctcttc cacccatgtc tctttgagca ataaagccga taacaaaatc tttgtcgctc   5340
ttcgcaatgt caacagtacc cttagtatat tctccagtag atagggagcc cttgcatgac   5400
aattctgcta acatcaaaag gcctctaggt tcctttgtta cttcttctgc cgcctgcttc   5460
aaaccgctaa caatacctgg gcccaccaca ccgtgtgcat tcgtaatgtc tgcccattct   5520
gctattctgt atacacccgc agagtactgc aatttgactg tattaccaat gtcagcaaat   5580
tttctgtctt cgaagagtaa aaaattgtac ttggcggata atgcctttag cggcttaact   5640
gtgccctcca tggaaaaatc agtcaagata tccacatgtg tttttagtaa acaaattttg   5700
ggacctaatg cttcaactaa ctccagtaat tccttggtgg tacgaacatc caatgaagca   5760
cacaagtttg tttgcttttc gtgcatgata ttaaatagct tggcagcaac aggactagga   5820
tgagtagcag cacgttcctt atatgtagct ttcgacatga tttatcttcg tttcctgcag   5880
gtttttgttc tgtgcagttg ggttaagaat actgggcaat ttcatgtttc ttcaacacta   5940
catatgcgta tatataccaa tctaagtctg tgctccttcc ttcgttcttc cttctgttcg   6000
gagattaccg aatcaaaaaa atttcaagga aaccgaaatc aaaaaaaaga ataaaaaaaa   6060
aatgatgaat tgaattgaaa agctgtggta tggtgcactc tcagtacaat ctgctctgat   6120
gccgcatagt taagccagcc ccgacacccg ccaacacccg ctgacgcgcc ctgacgggct   6180
tgtctgctcc cggcatccgc ttacagacaa gctgtgaccg tctccgggag ctgcatgtgt   6240
cagaggtttt caccgtcatc accgaaacgc gcga                               6274
```

<210> SEQ ID NO 6
<211> LENGTH: 20
<212> TYPE: DNA
<213> ORGANISM: Saccharomyces cerevisiae

<400> SEQUENCE: 6

```
tccaataacg gaatccaact                                                 20
```

<210> SEQ ID NO 7

<211> LENGTH: 3648
<212> TYPE: DNA
<213> ORGANISM: Artificial Sequence
<220> FEATURE:
<223> OTHER INFORMATION: Synthetic Sequence - Plasmid Vector 1548
<220> FEATURE:
<221> NAME/KEY: promoter
<222> LOCATION: (1)..(8)
<223> OTHER INFORMATION: AmpR promoter
<220> FEATURE:
<221> NAME/KEY: misc_feature
<222> LOCATION: (97)..(182)
<223> OTHER INFORMATION: ade1 pro homology
<220> FEATURE:
<221> NAME/KEY: gene
<222> LOCATION: (288)..(1091)
<223> OTHER INFORMATION: URA3
<220> FEATURE:
<221> NAME/KEY: promoter
<222> LOCATION: (1092)..(1307)
<223> OTHER INFORMATION: URA3 promoter
<220> FEATURE:
<221> NAME/KEY: misc_feature
<222> LOCATION: (1359)..(1538)
<223> OTHER INFORMATION: URA3 switch homology
<220> FEATURE:
<221> NAME/KEY: misc_feature
<222> LOCATION: (1544)..(1633)
<223> OTHER INFORMATION: Ade ORF start homology
<220> FEATURE:
<221> NAME/KEY: rep_origin
<222> LOCATION: (1932)..(2520)
<223> OTHER INFORMATION: ori
<220> FEATURE:
<221> NAME/KEY: gene
<222> LOCATION: (2691)..(3551)
<223> OTHER INFORMATION: AmpR
<220> FEATURE:
<221> NAME/KEY: promoter
<222> LOCATION: (3552)..(3648)
<223> OTHER INFORMATION: AmpR promoter

<400> SEQUENCE: 7
gttccgcgca catttccccg aaaagtgcca cctgacgtct aagaaaccat tattatcatg 60
acattaacct ataaaaatag gcgtatcacg aggcccgggt tttatctttt gcagttggta 120
ctattaagaa caatcgaatc ataagcattg cttacaaaga atacacatac gaaatattaa 180
cgcatctgtg cggtatttca caccgcatag ggtaataact gatataatta aattgaagct 240
ctaatttgtg agtttagtat acatgcattt acttataata cagtttttta gttttgctgg 300
ccgcatcttc tcaaatatgc ttcccagcct gcttttctgt aacgttcacc ctctacctta 360
gcatcccttc cctttgcaaa tagtcctctt ccaacaataa taatgtcaga tcctgtagag 420
accacatcat ccacggttct atactgttga cccaatgcgt ctcccttgtc atctaaaccc 480
acaccgggtg tcataatcaa ccaatcgtaa ccttcatctc ttccacccat gtctctttga 540
gcaataaagc cgataacaaa atctttgtcg ctcttcgcaa tgtcaacagt acccttagta 600
tattctccag tagataggga gcccttgcat gacaattctg ctaacatcaa aaggcctcta 660
ggttcctttg ttacttcttc tgccgcctgc ttcaaaccgc taacaatacc tgggcccacc 720
acaccgtgtg cattcgtaat gtctgcccat tctgctattc tgtatacacc cgcagagtac 780
tgcaatttga ctgtattacc aatgtcagca aattttctgt cttcgaagag taaaaaattg 840
tacttggcgg ataatgcctt tagcggctta actgtgccct ccatggaaaa atcagtcaag 900
atatccacat gtgtttttag taaacaaatt ttgggaccta atgcttcaac taactccagt 960
aattccttgg tggtacgaac atccaatgaa gcacacaagt ttgtttgctt ttcgtgcatg 1020
atattaaata gcttggcagc aacaggacta ggatgagtag cagcacgttc cttatatgta 1080

```
gctttcgaca tgatttatct tcgtttcctg caggtttttg ttctgtgcag ttgggttaag   1140
aatactgggc aatttcatgt ttcttcaaca ctacatatgc gtatatatac caatctaagt   1200
ctgtgctcct tccttcgttc ttccttctgt tcggagatta ccgaatcaaa aaaatttcaa   1260
agaaaccgaa atcaaaaaaa agaataaaaa aaaaaatgatg aattgaattg aaaagctgtg   1320
gtatggtgca ctctcagtac aatctgctct gatgccgcac agttaagccg ctaaaggcat   1380
tatccgccaa gtacaatttt ttactcttcg aagacagaaa atttgctgac attggtaata   1440
cagtcaaatt gcagtactct gcgggtgtat acagaatagc agaatgggca gacattacga   1500
atgcacacgg tgtggtgggc ccaggtattg ttagcggtgg agggtcaatt acgaagactg   1560
aactggacgg tatattgcca ttggtggcca gaggtaaagt tagagacata tatgaggtag   1620
acgctggtac gttaactcac attaattgcg ttgcgctcac tgcccgcttt ccagtcggga   1680
aacctgtcgt gccagctgca ttaatgaatc ggccaacgcg cggggagagg cggtttgcgt   1740
attgggcgct cttccgcttc ctcgctcact gactcgctgc gctcggtcgt tcggctgcgg   1800
cgagcggtat cagctcactc aaaggcggta atacggttat ccacagaatc aggggataac   1860
gcaggaaaga acatgtgagc aaaaggccag caaaaggcca ggaaccgtaa aaaggccgcg   1920
ttgctggcgt ttttccatag gctccgcccc cctgacgagc atcacaaaaa tcgacgctca   1980
agtcagaggt ggcgaaaccc gacaggacta taaagatacc aggcgtttcc ccctggaagc   2040
tccctcgtgc gctctcctgt tccgaccctg ccgcttaccg gatacctgtc cgcctttctc   2100
ccttcgggaa gcgtggcgct ttctcatagc tcacgctgta ggtatctcag ttcggtgtag   2160
gtcgttcgct ccaagctggg ctgtgtgcac gaaccccccg ttcagcccga ccgctgcgcc   2220
ttatccggta actatcgtct tgagtccaac ccggtaagac acgacttatc gccactggca   2280
gcagccactg gtaacaggat tagcagagcg aggtatgtag gcggtgctac agagttcttg   2340
aagtggtggc ctaactacgg ctacactaga agaacagtat ttggtatctg cgctctgctg   2400
aagccagtta ccttcggaaa aagagttggt agctcttgat ccggcaaaca aaccaccgct   2460
ggtagcggtg gtttttttgt ttgcaagcag cagattacgc gcagaaaaaa aggatctcaa   2520
gaagatcctt tgatcttttc tacggggtct gacgctcagt ggaacgaaaa ctcacgttaa   2580
gggattttgg tcatgagatt atcaaaaagg atcttcacct agatcctttt aaattaaaaa   2640
tgaagtttta aatcaatcta aagtatatat gagtaaactt ggtctgacag ttaccaatgc   2700
ttaatcagtg aggcacctat ctcagcgatc tgtctatttc gttcatccat agttgcctga   2760
ctccccgtcg tgtagataac tacgatacgg gagggcttac catctggccc cagtgctgca   2820
atgataccgc gagacccacg ctcaccggct ccagatttat cagcaataaa ccagccagcc   2880
ggaagggccg agcgcagaag tggtcctgca actttatccg cctccatcca gtctattaat   2940
tgttgccggg aagctagagt aagtagttcg ccagttaata gtttgcgcaa cgttgttgcc   3000
attgctacag gcatcgtggt gtcacgctcg tcgtttggta tggcttcatt cagctccggt   3060
tcccaacgat caaggcgagt tacatgatcc cccatgttgt gcaaaaaagc ggttagctcc   3120
ttcggtcctc cgatcgttgt cagaagtaag ttggccgcag tgttatcact catggttatg   3180
gcagcactgc ataattctct tactgtcatg ccatccgtaa gatgcttttc tgtgactggt   3240
gagtactcaa ccaagtcatt ctgagaatag tgtatgcggc gaccgagttg ctcttgcccg   3300
gcgtcaatac gggataatac cgcgccacat agcagaactt taaaagtgct catcattgga   3360
aaacgttctt cggggcgaaa actctcaagg atcttaccgc tgttgagatc cagttcgatg   3420
```

taacccactc gtgcacccaa ctgatcttca gcatctttta ctttcaccag cgtttctggg 3480
tgagcaaaaa caggaaggca aaatgccgca aaaaagggaa taagggcgac acggaaatgt 3540
tgaatactca tactcttcct ttttcaatat tattgaagca tttatcaggg ttattgtctc 3600
atgagcggat acatatttga atgtatttag aaaaataaac aaataggg 3648

<210> SEQ ID NO 8
<211> LENGTH: 12060
<212> TYPE: DNA
<213> ORGANISM: Artificial Sequence
<220> FEATURE:
<223> OTHER INFORMATION: Synthetic Sequence - Plasmid Vector 1251
<220> FEATURE:
<221> NAME/KEY: misc_feature
<222> LOCATION: (70)..(573)
<223> OTHER INFORMATION: CEN/ARS
<220> FEATURE:
<221> NAME/KEY: rep_origin
<222> LOCATION: (1746)..(2334)
<223> OTHER INFORMATION: ori
<220> FEATURE:
<221> NAME/KEY: promoter
<222> LOCATION: (2852)..(3516)
<223> OTHER INFORMATION: GAL1 and GAL10 genes of S. cerevisiae promoter
<220> FEATURE:
<221> NAME/KEY: gene
<222> LOCATION: (3519)..(7655)
<223> OTHER INFORMATION: Cas9
<220> FEATURE:
<221> NAME/KEY: misc_feature
<222> LOCATION: (7635)..(7655)
<223> OTHER INFORMATION: NLS of SV40
<220> FEATURE:
<221> NAME/KEY: misc_feature
<222> LOCATION: (7686)..(7856)
<223> OTHER INFORMATION: dead SH3
<220> FEATURE:
<221> NAME/KEY: misc_feature
<222> LOCATION: (7863)..(7928)
<223> OTHER INFORMATION: three tandem FLAG
<220> FEATURE:
<221> NAME/KEY: gene
<222> LOCATION: (7935)..(8558)
<223> OTHER INFORMATION: PmCDA1
<220> FEATURE:
<221> NAME/KEY: terminator
<222> LOCATION: (8589)..(8776)
<223> OTHER INFORMATION: S. cerevisiae ADH1 terminator
<220> FEATURE:
<221> NAME/KEY: rep_origin
<222> LOCATION: (9132)..(9587)
<223> OTHER INFORMATION: f1 ori
<220> FEATURE:
<221> NAME/KEY: promoter
<222> LOCATION: (9887)..(10291)
<223> OTHER INFORMATION: S. cerevisiae LEU2 prom
<220> FEATURE:
<221> NAME/KEY: gene
<222> LOCATION: (10304)..(11398)
<223> OTHER INFORMATION: S. cerevisiae LEU2

<400> SEQUENCE: 8
gacgaaaggg cctcgtgata cgcctatttt tataggttaa tgtcatgata ataatggttt 60
cttaggacgg atcgcttgcc tgtaacttac acgcgcctcg tatcttttaa tgatggaata 120
atttgggaat ttactctgtg tttatttatt tttatgtttt gtatttggat tttagaaagt 180
aaataaagaa ggtagaagag ttacggaatg aagaaaaaaa aataaacaaa ggtttaaaaa 240
atttcaacaa aaagcgtact ttacatatat atttattaga caagaaaagc agattaaata 300
gatatacatt cgattaacga taagtaaaat gtaaaatcac aggattttcg tgtgtggtct 360
tctacacaga caagatgaaa caattcggca ttaatacctg agagcaggaa gagcaagata 420

```
aaaggtagta tttgttggcg atccccctag agtcttttac atcttcggaa aacaaaaact    480
atttttttctt taatttcttt ttttactttc tatttttaat ttatatattt atattaaaaa    540
atttaaatta taattatttt tatagcacgt gatgaaaagg acccaggtgg cacttttcgg    600
ggaaatgtgc gcggaacccc tatttgttta tttttctaaa tacattcaaa tatgtatccg    660
ctcatgagac aataaccctg ataaatgctt caataatatt gaaaaaggaa gagtatgagt    720
attcaacatt tccgtgtcgc ccttattccc ttttttgcgg cattttgcct tcctgttttt    780
gctcacccag aaacgctggt gaaagtaaaa gatgctgaag atcagttggg tgcacgagtg    840
ggttacatcg aactggatct caacagcggt aagatccttg agagttttcg ccccgaagaa    900
cgttttccaa tgatgagcac ttttaaagtt ctgctatgtg gcgcggtatt atcccgtatt    960
gacgccgggc aagagcaact cggtcgccgc atacactatt ctcagaatga cttggttgag   1020
tactcaccag tcacagaaaa gcatcttacg gatggcatga cagtaagaga attatgcagt   1080
gctgccataa ccatgagtga taacactgcg gccaacttac ttctgacaac gatcggagga   1140
ccgaaggagc taaccgcttt tttcacaac atgggggatc atgtaactcg ccttgatcgt   1200
tgggaaccgg agctgaatga agccatacca aacgacgagc gtgacaccac gatgcctgta   1260
gcaatggcaa caacgttgcg caaactatta actggcgaac tacttactct agcttcccgg   1320
caacaattaa tagactggat ggaggcggat aaagttgcag gaccacttct gcgctcggcc   1380
cttccggctg gctggtttat tgctgataaa tctggagccg gtgagcgtgg gtctcgcggt   1440
atcattgcag cactggggcc agatggtaag ccctcccgta tcgtagttat ctacacgacg   1500
ggcagtcagg caactatgga tgaacgaaat agacagatcg ctgagatagg tgcctcactg   1560
attaagcatt ggtaactgtc agaccaagtt tactcatata tactttagat tgatttaaaa   1620
cttcattttt aatttaaaag gatctaggtg aagatccttt ttgataatct catgaccaaa   1680
atcccttaac gtgagttttc gttccactga gcgtcagacc ccgtagaaaa gatcaaagga   1740
tcttcttgag atcctttttt tctgcgcgta atctgctgct tgcaaacaaa aaaaccaccg   1800
ctaccagcgg tggtttgttt gccggatcaa gagctaccaa ctctttttcc gaaggtaact   1860
ggcttcagca gagcgcagat accaaatact gtccttctag tgtagccgta gttaggccac   1920
cacttcaaga actctgtagc accgcctaca tacctcgctc tgctaatcct gttaccagtg   1980
gctgctgcca gtggcgataa gtcgtgtctt accgggttgg actcaagacg atagttaccg   2040
gataaggcgc agcggtcggg ctgaacgggg ggttcgtgca cacagcccag cttggagcga   2100
acgacctaca ccgaactgag atacctacag cgtgagcatt gagaaagcgc cacgcttccc   2160
gaagggagaa aggcggacag gtatccggta agcggcaggg tcggaacagg agagcgcacg   2220
agggagcttc cagggggaa cgcctggtat ctttatagtc ctgtcgggtt tcgccacctc   2280
tgacttgagc gtcgattttt gtgatgctcg tcaggggggc ggagcctatg gaaaaacgcc   2340
agcaacgcgg cctttttacg gttcctggcc ttttgctggc cttttgctca catgttcttt   2400
cctgcgttat cccctgattc tgtggataac cgtattaccg cctttgagtg agctgatacc   2460
gctcgccgca gccgaacgac cgagcgcagc gagtcagtga gcgaggaagc ggaagagcgc   2520
ccaatacgca aaccgcctct ccccgcgcgt tggccgattc attaatgcag ctggcacgac   2580
aggtttcccg actggaaagc gggcagtgag cgcaacgcaa ttaatgtgag ttagctcact   2640
cattaggcac cccaggcttt acactttatg cttccggctc gtatgttgtg tggaattgtg   2700
agcggataac aatttcacac aggaaacagc tatgaccatg attacgccaa gctcgaaatt   2760
```

```
aaccctcact aaagggaaca aaagctggta ccgggcccga attctctcct tctcttaggt   2820
ggcagagcag gtggagggtc gaccatacta gtttcaaaaa ttcttacttt tttttggat    2880
ggacgcaaag aagtttaata atcatattac atggcattac caccatatac atatccatat   2940
acatatccat atctaatctt acttatatgt tgtggaaatg taaagagccc cattatctta   3000
gcctaaaaaa accttctctt tggaactttc agtaatacgc ttaactgctc attgctatat   3060
tgaagtacgg attagaagcc gccgagcggg tgacagccct ccgaaggaag actctcctcc   3120
gtgcgtcctc gtcttcaccg gtcgcgttcc tgaaacgcag atgtgcctcg cgccgcactg   3180
ctccgaacaa taaagattct acaatactag cttttatggt tatgaagagg aaaaattggc   3240
agtaacctgg ccccacaaac cttcaaatga acgaatcaaa ttaacaacca taggatgata   3300
atgcgattag ttttttagcc ttatttctgg ggtaattaat cagcgaagcg atgatttttg   3360
atctattaac agatatataa atgcaaaaac tgcataacca ctttaactaa tactttcaac   3420
attttcggtt tgtattactt cttattcaaa tgtaataaaa gtatcaacaa aaaattgtta   3480
atatacctct atactttaac gtcaaggaga aaaaaaccat ggacaagaag tactccattg   3540
ggctcgctat cggcacaaac agcgtcggtt gggccgtcat tacggacgag tacaaggtgc   3600
cgagcaaaaa attcaaagtt ctgggcaata ccgatcgcca cagcataaag aagaacctca   3660
ttggcgccct cctgttcgac tccggggaga cggccgaagc cacgcggctc aaaagaacag   3720
cacggcgcag atatacccgc agaaagaatc ggatctgcta cctgcaggag atctttagta   3780
atgagatggc taaggtggat gactctttct tccataggct ggaggagtcc tttttggtgg   3840
aggaggataa aaagcacgag cgccacccaa tctttggcaa tatcgtggac gaggtggcgt   3900
accatgaaaa gtacccaacc atatatcatc tgaggaagaa gcttgtagac agtactgata   3960
aggctgactt gcggttgatc tatctcgcgc tggcgcatat gatcaaattt cggggacact   4020
tcctcatcga gggggacctg aacccagaca acagcgatgt cgacaaactc tttatccaac   4080
tggttcagac ttacaatcag cttttcgaag agaacccgat caacgcatcc ggagttgacg   4140
ccaaagcaat cctgagcgct aggctgtcca aatcccggcg gctcgaaaac ctcatcgcac   4200
agctccctgg ggagaagaag aacggcctgt ttggtaatct tatcgccctg tcactcgggc   4260
tgacccccaa ctttaaatct aacttcgacc tggccgaaga tgccaagctt caactgagca   4320
aagacaccta cgatgatgat ctcgacaatc tgctggccca gatcggcgac cagtacgcag   4380
acctttttt ggcggcaaag aacctgtcag acgccattct gctgagtgat attctgcgag    4440
tgaacacgga gatcaccaaa gctccgctga gcgctagtat gatcaagcgc tatgatgagc   4500
accaccaaga cttgactttg ctgaaggccc ttgtcagaca gcaactgcct gagaagtaca   4560
aggaaatttt cttcgatcag tctaaaaatg gctacgccgg atacattgac ggcggagcaa   4620
gccaggagga attttacaaa tttattaagc ccatcttgga aaaaatggac ggcaccgagg   4680
agctgctggt aaagcttaac agagaagatc tgttgcgcaa acagcgcact ttcgacaatg   4740
gaagcatccc ccaccagatt cacctgggcg aactgcacgc tatcctcagg cggcaagagg   4800
atttctaccc ctttttgaaa gataacaggg aaaagattga gaaaatcctc acatttcgga   4860
taccctacta tgtaggcccc ctcgcccggg gaaattccag attcgcgtgg atgactcgca   4920
aatcagaaga gaccatcact ccctggaact tcgaggaagt cgtggataag ggggcctctg   4980
cccagtcctt catcgaaagg atgactaact ttgataaaaa tctgcctaac gaaaaggtgc   5040
ttcctaaaca ctctctgctg tacgagtact tcacagttta taacgagctc accaaggtca   5100
aatacgtcac agaagggatg agaaagccag cattcctgtc tggagagcag aagaaagcta   5160
```

```
tcgtggacct cctcttcaag acgaaccgga aagttaccgt gaaacagctc aaagaagact   5220
atttcaaaaa gattgaatgt ttcgactctg ttgaaatcag cggagtggag gatcgcttca   5280
acgcatccct gggaacgtat cacgatctcc tgaaaatcat taaagacaag gacttcctgg   5340
acaatgagga gaacgaggac attcttgagg acattgtcct cacccttacg ttgtttgaag   5400
atagggagat gattgaagaa cgcttgaaaa cttacgctca tctcttcgac gacaaagtca   5460
tgaaacagct caagaggcgc cgatatacag gatgggggcg gctgtcaaga aaactgatca   5520
atgggatccg agacaagcag agtggaaaga caatcctgga ttttcttaag tccgatggat   5580
ttgccaaccg gaacttcatg cagttgatcc atgatgactc tctcaccttt aaggaggaca   5640
tccagaaagc acaagtttct ggccaggggg acagtcttca cgagcacatc gctaatcttg   5700
caggtagccc agctatcaaa aagggaatac tgcagaccgt taaggtcgtg gatgaactcg   5760
tcaaagtaat gggaaggcat aagcccgaga atatcgttat cgagatggcc cgagagaacc   5820
aaactaccca gaagggacag aagaacagta gggaaaggat gaagaggatt gaagagggta   5880
taaaagaact ggggtcccaa atccttaagg aacacccagt tgaaaacacc cagcttcaga   5940
atgagaagct ctacctgtac tacctgcaga acggcaggga catgtacgtg gatcaggaac   6000
tggacatcaa tcggctctcc gactacgacg tggatgctat cgtgccccag tcttttctca   6060
aagatgattc tattgataat aaagtgttga caagatccga taaaaataga gggaagagtg   6120
ataacgtccc ctcagaagaa gttgtcaaga aaatgaaaaa ttattggcgg cagctgctga   6180
acgccaaact gatcacacaa cggaagttcg ataatctgac taaggctgaa cgaggtggcc   6240
tgtctgagtt ggataaagcc ggcttcatca aaaggcagct tgttgagaca cgccagatca   6300
ccaagcacgt ggcccaaatt ctcgattcac gcatgaacac caagtacgat gaaaatgaca   6360
aactgattcg agaggtgaaa gttattactc tgaagtctaa gctggtctca gatttcagaa   6420
aggactttca gttttataag gtgagagaga tcaacaatta ccaccatgcg catgatgcct   6480
acctgaatgc agtggtaggc actgcactta tcaaaaaata tcccaagctt gaatctgaat   6540
ttgtttacgg agactataaa gtgtacgatg ttaggaaaat gatcgcaaag tctgagcagg   6600
aaataggcaa ggccaccgct aagtacttct tttacagcaa tattatgaat tttttcaaga   6660
ccgagattac actggccaat ggagagattc ggaagcgacc acttatcgaa acaaacggag   6720
aaacaggaga aatcgtgtgg gacaagggta gggatttcgc gacagtccgg aaggtcctgt   6780
ccatgccgca ggtgaacatc gttaaaaaga ccgaagtaca gaccggaggc ttctccaagg   6840
aaagtatcct cccgaaaagg aacagcgaca agctgatcgc acgcaaaaaa gattgggacc   6900
ccaagaaata cggcggattc gattctccta cagtcgctta cagtgtactg gttgtggcca   6960
aagtggagaa agggaagtct aaaaaactca aaagcgtcaa ggaactgctg ggcatcacaa   7020
tcatggagcg atcaagcttc gaaaaaaacc ccatcgactt tctcgaggcg aaaggatata   7080
aagaggtcaa aaaagacctc atcattaagc ttcccaagta ctctctcttt gagcttgaaa   7140
acggccggaa acgaatgctc gctagtgcgg gcgagctgca gaaaggtaac gagctggcac   7200
tgccctctaa atacgttaat ttcttgtatc tggccagcca ctatgaaaag ctcaaagggt   7260
ctcccgaaga taatgagcag aagcagctgt tcgtggaaca acacaaacac taccttgatg   7320
agatcatcga gcaaataagc gaattctcca aaagagtgat cctcgccgac gctaacctcg   7380
ataaggtgct ttctgcttac aataagcaca gggataagcc catcagggag caggcagaaa   7440
acattatcca cttgtttact ctgaccaact tgggcgcgcc tgcagccttc aagtacttcg   7500
```

```
acaccaccat agacagaaag cggtacacct ctacaaagga ggtcctggac gccacactga   7560
ttcatcagtc aattacgggg ctctatgaaa caagaatcga cctctctcag ctcggtggag   7620
acagcagggc tgaccccaag aagaagagga aggtgggtgg aggaggttct ggaggtggag   7680
gttctgcaga gtatgtgcgg gccctctttg actttaatgg gaatgatgaa gaagatcttc   7740
cctttaagaa aggagacatc ctgagaatcc gggataagcc tgaagagcag tggtggaatg   7800
cagaggacag cgaaggaaag agggggatga ttcttgtccc ttacgtggag aagtattccg   7860
gagactataa ggaccacgac ggagactaca aggatcatga tattgattac aaagacgatg   7920
acgataagtc taggatgacc gacgctgagt acgtgagaat ccatgagaag ttggacatct   7980
acacgtttaa gaaacagttt ttcaacaaca aaaaatccgt gtcgcataga tgctacgttc   8040
tctttgaatt aaaacgacgg ggtgaacgta gagcgtgttt ttggggctat gctgtgaata   8100
aaccacagag cgggacagaa cgtggcattc acgccgaaat ctttagcatt agaaaagtcg   8160
aagaatacct gcgcgacaac cccggacaat tcacgataaa ttggtactca tcctggagtc   8220
cttgtgcaga ttgcgctgaa aagatcttag aatggtataa ccaggagctg cgggggaacg   8280
gccacacttt gaaaatctgg gcttgcaaac tctattacga gaaaaatgcg aggaatcaaa   8340
ttgggctgtg gaacctcaga gataacgggg ttgggttgaa tgtaatggta agtgaacact   8400
accaatgttg caggaaaata ttcatccaat cgtcgcacaa tcaattgaat gagaatagat   8460
ggcttgagaa gactttgaag cgagctgaaa aacgacggag cgagttgtcc attatgattc   8520
aggtaaaaat actccacacc actaagagtc ctgctgtttc tagaggctcc ggataaggat   8580
cctaataagc gaatttctta tgatttatga tttttattat taaataagtt ataaaaaaaa   8640
taagtgtata caaattttaa agtgactctt aggttttaaa acgaaaattc ttattcttga   8700
gtaactcttt cctgtaggtc aggttgcttt ctcaggtata gcatgaggtc gctcttattg   8760
accacacctc taccggcatg ccgagcaaat gcctgcaaat cgctcccggg caaaaaaccc   8820
cctcaagacc cgtttagagg ccccaagggg ttatgctatg catactgata taattaaatt   8880
gaagctctaa tttgtgagtt tagtatacat gcataccaag cttccgcggt ggagctccaa   8940
ttcgccctat agtgagtcgt attacaattc actggccgtc gttttacaac gtcgtgactg   9000
ggaaaaccct ggcgttaccc aacttaatcg ccttgcagca catccccct tcgccagctg   9060
gcgtaatagc gaagaggccc gcaccgatcg cccttcccaa cagttgcgca gcctgaatgg   9120
cgaatggcgc gacgcgccct gtagcggcgc attaagcgcg gcgggtgtgg tggttacgcg   9180
cagcgtgacc gctacacttg ccagcgccct agcgcccgct cctttcgctt tcttcccttc   9240
ctttctcgcc acgttcgccg gctttccccg tcaagctcta aatcgggggc tccctttagg   9300
gttccgattt agtgctttac ggcacctcga ccccaaaaaa cttgattagg gtgatggttc   9360
acgtagtggg ccatcgccct gatagacggt ttttcgccct ttgacgttgg agtccacgtt   9420
ctttaatagt ggactcttgt tccaaactgg aacaacactc aaccctatct cggtctattc   9480
ttttgattta taagggattt tgccgatttc ggcctattgg ttaaaaaatg agctgattta   9540
acaaaaattt aacgcgaatt ttaacaaaat attaacgttt acaatttcct gatgcggtat   9600
tttctcctta cgcatctgtg cggtatttca caccgcatat cgaccctcga ggagaacttc   9660
tagtatatcc acatacctaa tattattgcc ttattaaaaa tggaatcgga acaattacat   9720
caaaatccac attctcttca aaatcaattg tcctgtactt ccttgttcat gtgtgttcaa   9780
aaacgttata tttataggat aattatactc tatttctcaa caagtaattg gttgtttggc   9840
cgagcggtct aaggcgcctg attcaagaaa tatcttgacc gcagttaact gtgggaatac   9900
```

```
tcaggtatcg taagatgcaa gagttcgaat ctcttagcaa ccattatttt tttcctcaac   9960
ataacgagaa cacacagggg cgctatcgca cagaatcaaa ttcgatgact ggaaattttt  10020
tgttaatttc agaggtcgcc tgacgcatat acctttttca actgaaaaat tgggagaaaa  10080
aggaaaggtg agaggccgga accggctttt catatagaat agagaagcgt tcatgactaa  10140
atgcttgcat cacaatactt gaagttgaca atattattta aggacctatt gtttttcca  10200
ataggtggtt agcaatcgtc ttactttcta acttttctta ccttttacat ttcagcaata  10260
tatatatata tttcaaggat ataccattct aatgtctgcc cctatgtctg ccccctaagaa  10320
gatcgtcgtt ttgccaggtg accacgttgg tcaagaaatc acagccgaag ccattaaggt  10380
tcttaaagct atttctgatg ttcgttccaa tgtcaagttc gatttcgaaa atcatttaat  10440
tggtggtgct gctatcgatg ctacaggtgt cccacttcca gatgaggcgc tggaagcctc  10500
caagaaggtt gatgccgttt tgttaggtgc tgtgggtggt cctaaatggg gtaccggtag  10560
tgttagacct gaacaaggtt tactaaaaat ccgtaaagaa cttcaattgt acgccaactt  10620
aagaccatgt aactttgcat ccgactctct tttagactta tctccaatca agccacaatt  10680
tgctaaaggt actgacttcg ttgttgtcag agaattagtg ggaggtattt actttggtaa  10740
gagaaaggaa gacgatggtg atggtgtcgc ttgggatagt gaacaataca ccgttccaga  10800
agtgcaaaga atcacaagaa tggccgcttt catggcccta caacatgagc caccattgcc  10860
tatttggtcc ttggataaag ctaatgtttt ggcctcttca agattatgga gaaaaactgt  10920
ggaggaaacc atcaagaacg aattccctac attgaaggtt caacatcaat tgattgattc  10980
tgccgccatg atcctagtta agaacccaac ccacctaaat ggtattataa tcaccagcaa  11040
catgtttggt gatatcatct ccgatgaagc ctccgttatc ccaggttcct tgggtttgtt  11100
gccatctgcg tccttggcct ctttgccaga caagaacacc gcatttggtt tgtacgaacc  11160
atgccacggt tctgctccag atttgccaaa gaataaggtt gaccctatcg ccactatctt  11220
gtctgctgca atgatgttga aattgtcatt gaacttgcct gaagaaggta aggccattga  11280
agatgcagtt aaaaaggttt tggatgcagg tatcagaact ggtgatttag gtggttccaa  11340
cagtaccacc gaagtcggtg atgctgtcgc cgaagaagtt aagaaaatcc ttgcttaaaa  11400
agattctctt tttttatgat atttgtacat aaactttata aatgaaattc ataatagaaa  11460
cgacacgaaa ttacaaaatg gaatatgttc atagggtaga cgaaactata tacgcaatct  11520
acatacattt atcaagaagg agaaaaagga ggatagtaaa ggaatacagg taagcaaatt  11580
gatactaatg gctcaacgtg ataaggaaaa agaattgcac tttaacatta atattgacaa  11640
ggaggagggc accacacaaa aagttaggtg taacagaaaa tcatgaaact acgattccta  11700
atttgatatt ggaggatttt ctctaaaaaa aaaaaaatac aacaaataaa aaacactcaa  11760
tgacctgacc atttgatgga gtttaagtca ataccttctt gaaccatttc ccataatggt  11820
gaaagttccc tcaagaattt tactctgtca gaaacggcct tacgacgtag tcgatatggt  11880
gcactctcag tacaatctgc tctgatgccg catagttaag ccagccccga cacccgccaa  11940
cacccgctga cgcgccctga cgggcttgtc tgctcccggc atccgcttac agacaagctg  12000
tgaccgtctc cgggagctgc atgtgtcaga ggttttcacc gtcatcaccg aaacgcgcga  12060
```

<210> SEQ ID NO 9
<211> LENGTH: 20
<212> TYPE: DNA
<213> ORGANISM: Saccharomyces cerevisiae

<400> SEQUENCE: 9
cctttagcgg cttaactgtg 20

<210> SEQ ID NO 10
<211> LENGTH: 20
<212> TYPE: DNA
<213> ORGANISM: Saccharomyces cerevisiae

<400> SEQUENCE: 10
ggcccaggta ttgttagcgg 20

<210> SEQ ID NO 11
<211> LENGTH: 20
<212> TYPE: DNA
<213> ORGANISM: Saccharomyces cerevisiae

<400> SEQUENCE: 11
ttggcggata atgcctttag 20

<210> SEQ ID NO 12
<211> LENGTH: 20
<212> TYPE: DNA
<213> ORGANISM: Saccharomyces cerevisiae

<400> SEQUENCE: 12
tgcagttggg ttaagaatac 20

<210> SEQ ID NO 13
<211> LENGTH: 20
<212> TYPE: DNA
<213> ORGANISM: Saccharomyces cerevisiae

<400> SEQUENCE: 13
gctaacatca aaaggcctct 20

<210> SEQ ID NO 14
<211> LENGTH: 20
<212> TYPE: DNA
<213> ORGANISM: Saccharomyces cerevisiae

<400> SEQUENCE: 14
ttggcggata atgcctttag 20

<210> SEQ ID NO 15
<211> LENGTH: 7250
<212> TYPE: DNA
<213> ORGANISM: Artificial Sequence
<220> FEATURE:
<223> OTHER INFORMATION: Synthetic Sequence - Plasmid Vector 1xgRNA Can cross
<220> FEATURE:
<221> NAME/KEY: gene
<222> LOCATION: (133)..(993)
<223> OTHER INFORMATION: AmpR
<220> FEATURE:
<221> NAME/KEY: promoter
<222> LOCATION: (994)..(1098)
<223> OTHER INFORMATION: AmpR promoter
<220> FEATURE:
<221> NAME/KEY: rep_origin
<222> LOCATION: (1125)..(2467)
<223> OTHER INFORMATION: 2 micro ori
<220> FEATURE:
<221> NAME/KEY: misc_feature
<222> LOCATION: (2521)..(2994)
<223> OTHER INFORMATION: Can1_Left arm
<220> FEATURE:

<221> NAME/KEY: promoter
<222> LOCATION: (3231)..(3446)
<223> OTHER INFORMATION: URA3 promoter
<220> FEATURE:
<221> NAME/KEY: gene
<222> LOCATION: (3447)..(4250)
<223> OTHER INFORMATION: URA3
<220> FEATURE:
<221> NAME/KEY: rep_origin
<222> LOCATION: (4381)..(4836)
<223> OTHER INFORMATION: f1 ori
<220> FEATURE:
<221> NAME/KEY: misc_feature
<222> LOCATION: (5054)..(5507)
<223> OTHER INFORMATION: Can1_Right Arm
<220> FEATURE:
<221> NAME/KEY: terminator
<222> LOCATION: (5519)..(5766)
<223> OTHER INFORMATION: CYC1 terminator
<220> FEATURE:
<221> NAME/KEY: terminator
<222> LOCATION: (5772)..(5785)
<223> OTHER INFORMATION: Sup4 term
<220> FEATURE:
<221> NAME/KEY: misc_structure
<222> LOCATION: (5788)..(5870)
<223> OTHER INFORMATION: tracrRNA
<220> FEATURE:
<221> NAME/KEY: misc_feature
<222> LOCATION: (5871)..(5890)
<223> OTHER INFORMATION: target1R
<220> FEATURE:
<221> NAME/KEY: promoter
<222> LOCATION: (5891)..(6159)
<223> OTHER INFORMATION: SNR52 promoter
<220> FEATURE:
<221> NAME/KEY: misc_feature
<222> LOCATION: (6222)..(6238)
<223> OTHER INFORMATION: M13 rev
<220> FEATURE:
<221> NAME/KEY: misc_feature
<222> LOCATION: (6246)..(6262)
<223> OTHER INFORMATION: lac operator
<220> FEATURE:
<221> NAME/KEY: promoter
<222> LOCATION: (6270)..(6300)
<223> OTHER INFORMATION: lac promoter
<220> FEATURE:
<221> NAME/KEY: rep_origin
<222> LOCATION: (6624)..(7212)
<223> OTHER INFORMATION: ori

<400> SEQUENCE: 15
gtggaacgaa aactcacgtt aagggatttt ggtcatgaga ttatcaaaaa ggatcttcac 60
ctagatcctt ttaaattaaa aatgaagttt taaatcaatc taaagtatat atgagtaaac 120
ttggtctgac agttaccaat gcttaatcag tgaggcacct atctcagcga tctgtctatt 180
tcgttcatcc atagttgcct gactccccgt cgtgtagata actacgatac gggagggctt 240
accatctggc cccagtgctg caatgatacc gcgagaccca cgctcaccgg ctccagattt 300
atcagcaata aaccagccag ccggaagggc cgagcgcaga agtggtcctg caactttatc 360
cgcctccatc cagtctatta attgttgccg ggaagctaga gtaagtagtt cgccagttaa 420
tagtttgcgc aacgttgttg ccattgctac aggcatcgtg gtgtcacgct cgtcgtttgg 480
tatggcttca ttcagctccg gttcccaacg atcaaggcga gttacatgat cccccatgtt 540
gtgcaaaaaa gcggttagct ccttcggtcc tccgatcgtt gtcagaagta agttggccgc 600
agtgttatca ctcatggtta tggcagcact gcataattct cttactgtca tgccatccgt 660
aagatgcttt tctgtgactg gtgagtactc aaccaagtca ttctgagaat agtgtatgcg 720
gcgaccgagt tgctcttgcc cggcgtcaat acgggataat accgcgccac atagcagaac 780

```
tttaaaagtg ctcatcattg gaaaacgttc ttcggggcga aaactctcaa ggatcttacc    840
gctgttgaga tccagttcga tgtaacccac tcgtgcaccc aactgatctt cagcatcttt    900
tactttcacc agcgtttctg ggtgagcaaa aacaggaagg caaaatgccg caaaaaaggg    960
aataagggcg acacggaaat gttgaatact catactcttc ctttttcaat attattgaag   1020
catttatcag ggttattgtc tcatgagcgg atacatattt gaatgtattt agaaaaataa   1080
acaaataggg gttccgcgca catttccccg aaaagtgcca cctgaacgaa gcatctgtgc   1140
ttcattttgt agaacaaaaa tgcaacgcga gagcgctaat ttttcaaaca aagaatctga   1200
gctgcatttt tacagaacag aaatgcaacg cgaaagcgct atttaccaa cgaagaatct    1260
gtgcttcatt tttgtaaaac aaaaatgcaa cgcgagagcg ctaatttttc aaacaaagaa   1320
tctgagctgc atttttacag aacagaaatg caacgcgaga gcgctatttt accaacaaag   1380
aatctatact tctttttgt tctacaaaaa tgcatcccga gagcgctatt tttctaacaa    1440
agcatcttag attacttttt ttctcctttg tgcgctctat aatgcagtct cttgataact   1500
ttttgcactg taggtccgtt aaggttagaa gaaggctact tggtgtctta ttttctcttc   1560
cataaaaaaa gcctgactcc acttcccgcg tttactgatt actagcgaag ctgcgggtgc   1620
attttttcaa gataaaggca tccccgatta tattctatac cgatgtggat tgcgcatact   1680
ttgtgaacag aaagtgatag cgttgatgat tcttcattgg tcagaaaatt atgaacggtt   1740
tcttctattt tgtctctata tactacgtat aggaaatgtt tacattttcg tattgttttc   1800
gattcactct atgaatagtt cttactacaa tttttttgtc taaagagtaa tactagagat   1860
aaacataaaa aatgtagagg tcgagtttag atgcaagttc aaggagcgaa aggtggatgg   1920
gtaggttata tagggatata gcacagagat atatagcaaa gagatacttt tgagcaatgt   1980
ttgtggaagc ggtattcgca atattttagt agctcgttac agtccggtgc gtttttggtt   2040
ttttgaaagt gcgtcttcag agcgcttttg gttttcaaaa gcgctctgaa gttcctatac   2100
tttctagaga ataggaactt cggaatagga acttcaaagc gtttccgaaa acgagcgctt   2160
ccgaaaatgc aacgcgagct gcgcacatac agctcactgt tcacgtcgca cctatatctg   2220
cgtgttgcct gtatatatat atacatgaga agaacggcat agtgcgtgtt tatgcttaaa   2280
tgcgtactta tatgcgtcta tttatgtagg atgaaaggta gtctagtacc tcctgtgata   2340
ttatcccatt ccatgcgggg tatcgtatgc ttccttcagc actacccttt agctgttcta   2400
tatgctgcca ctcctcaatt ggattagtct catccttcaa tgctatcatt tcctttgata   2460
ttggatcata ctaagaaacc attattatca tgacattaac ctataaaaat aggcgcatgc   2520
ttattagcct tgatagtgct gaaaaaaaga aaaaaaacaa aaaaaagaaa taaaataacg   2580
gcaaacagca aaggccacag aaccgtattc atgttacttc tgcaatatca atcacttact   2640
ggcaagtgcg tataaattaa acctatttct ttatcatcat atttacttat atctttaaca   2700
gattccaaac cctaaagtgt ccgaattttc aatagggcga acttgaagaa taaccaaggt   2760
caataatata tcttttagta taaccctgaa atttgcccta tagaaatcta gggtttctgt   2820
gtggtttccg ggtgagtcat acggcttttt tgaatttctt tttttgcagt tgtctctatc   2880
aatgaaaatt tcgaggaaga cgataaggtt aagataagta gataagagaa tgatacgaga   2940
taaagcacaa attagcagaa agaagagtgg ttgcgaacag agtaaaccga atcagacgtc   3000
agacctaggt catgccgagg ccctttcgtc tcgcgcgttt cggtgatgac ggtgaaaacc   3060
tctgacacat gcagctcccg gagacggtca cagcttgtct gtaagcggat gccgggagca   3120
```

-continued

```
gacaagcccg tcagggcgcg tcagcgggtg ttggcgggtg tcggggctgg cttaactatg   3180
cggcatcaga gcagattgta ctgagagtgc accataccac agcttttcaa ttcaattcat   3240
catttttttt ttattctttt ttttgatttc ggtttccttg aaattttttt gattcggtaa   3300
tctccgaaca gaaggaagaa cgaaggaagg agcacagact tagattggta tatatacgca   3360
tatgtagtgt tgaagaaaca tgaaattgcc cagtattctt aacccaactg cacagaacaa   3420
aaacctgcag gaaacgaaga taaatcatgt cgaaagctac atataaggaa cgtgctgcta   3480
ctcatcctag tcctgttgct gccaagctat ttaatatcat gcacgaaaag caaacaaact   3540
tgtgtgcttc attggatgtt cgtaccacca aggaattact ggagttagtt gaagcattag   3600
gtcccaaaat ttgtttacta aaaacacatg tggatatctt gactgatttt tccatggagg   3660
gcacagttaa gccgctaaag gcattatccg ccaagtacaa tttttactc ttcgaagaca   3720
gaaaatttgc tgacattggt aatacagtca aattgcagta ctctgcgggt gtatacagaa   3780
tagcagaatg ggcagacatt acgaatgcac acggtgtggt gggcccaggt attgttagcg   3840
gtttgaagca ggcggcagaa gaagtaacaa aggaacctag aggccttttg atgttagcag   3900
aattgtcatg caagggctcc ctatctactg gagaatatac taagggtact gttgacattg   3960
cgaagagcga caaagatttt gttatcggct ttattgctca aagagacatg ggtggaagag   4020
atgaaggtta cgattggttg attatgacac ccggtgtggg tttagatgac aagggagacg   4080
cattgggtca acagtataga accgtggatg atgtggtctc tacaggatct gacattatta   4140
ttgttggaag aggactattt gcaaagggaa gggatgctaa ggtagagggt gaacgttaca   4200
gaaaagcagg ctgggaagca tatttgagaa gatgcggcca gcaaaactaa aaaactgtat   4260
tataagtaaa tgcatgtata ctaaactcac aaattagagc ttcaatttaa ttatatcagt   4320
tattacccta tgcggtgtga aataccgcac agatgcgtaa ggagaaaata ccgcatcagg   4380
aaattgtaaa cgttaatatt ttgttaaaat tcgcgttaaa tttttgttaa atcagctcat   4440
tttttaacca ataggccgaa atcggcaaaa tcccttataa atcaaaagaa tagaccgaga   4500
tagggttgag tgttgttcca gtttggaaca agagtccact attaaagaac gtggactcca   4560
acgtcaaagg gcgaaaaacc gtctatcagg gcgatggccc actacgtgaa ccatcaccct   4620
aatcaagttt tttggggtcg aggtgccgta aagcactaaa tcggaaccct aaagggagcc   4680
cccgatttag agcttgacgg ggaaagccgg cgaacgtggc gagaaaggaa gggaagaaag   4740
cgaaaggagc gggcgctagg gcgctggcaa gtgtagcggt cacgctgcgc gtaaccacca   4800
cacccgccgc gcttaatgcg ccgctacagg gcgcgtcgcg ccattcgcca ttcaggctgc   4860
gcaactgttg ggaagggcga tcggtgcggg cctcttcgct attacgccag ctggcgaaag   4920
ggggatgtgc tgcaaggcga ttaagttggg taacgccagg gttttcccag tcacgacgtt   4980
gtaaaacgac ggccagtgag cgcgcgtaat acgactcact atagggcgaa ttgggtactc   5040
ctaggttaat taagataatg tctgagttag gtgagtattc taaattagaa aacaaagagc   5100
ttagaacgga gtttgaattg acaaattttc cttttccagg cacaactgat aacgactccg   5160
atgacggaag ccaagggcag aactctttga atatcattac tcctgacatg gatgatactc   5220
tggttaatga tgtacttcga gaaaacgata aaaagtctag tatgagaatg gcttttatga   5280
atctagcaaa ctctattctt ggtgccggaa taattactca gccgttcgcg atcaaaaatg   5340
ctggtatatt aggcgggcta ttatcatacg tagccctcgg atttatagtt gattggacgt   5400
taagacttat tgtcattaac ttgactcttg ctggcaagag aacataccag ggtacggtcg   5460
aacatgtaat gggtaaaaaa gggaaattgc tgattctatt tacaaactgg taccggccgc   5520
```

```
aaattaaagc cttcgagcgt cccaaaacct tctcaagcaa ggttttcagt ataatgttac   5580

atgcgtacac gcgtctgtac agaaaaaaaa gaaaaatttg aaatataaat aacgttctta   5640

atactaacat aactataaaa aaataaatag ggacctagac ttcaggttgt ctaactcctt   5700

ccttttcggt tagagcggat gtgggggggag ggcgtgaacg taagcgtgac ataactaatt   5760

acatgactcg aagacataaa aaacaaaaaa agcaccaccg actcggtgcc actttttcaa   5820

gttgataacg gactagcctt attttaactt gctatttcta gctctaaaac gaaaagggga   5880

tcctattgac gatcatttat ctttcactgc ggagaagttt cgaacgccga aacatgcgca   5940

ccaactttca cttctacagc gtttgaccaa aatcttttga acagaacatt gtagggtgtg   6000

aaaaaatgcg cacctttacc gctagcccaa gagggcacta caaaatctag agttgtactt   6060

caaacgtaca tgtaatcacc ttgtatatac tcgaaagaaa acatcaagtt tctgtataaa   6120

tatgagtgaa agcataatca tacattatct tttcaaagaa gctccagctt ttgttccctt   6180

tagtgatcac gtccggattg cggccgcttg gcgtaatcat ggtcatagct gtttcctgtg   6240

tgaaattgtt atccgctcac aattccacac aacatacgag ccggaagcat aaagtgtaaa   6300

gcctggggtg cctaatgagt gagctaactc acattaattg cgttgcgctc actgcccgct   6360

ttccagtcgg gaaacctgtc gtgccagctg cattaatgaa tcggccaacg cgcggggaga   6420

ggcggtttgc gtattgggcg ctcttccgct tcctcgctca ctgactcgct gcgctcggtc   6480

gttcggctgc ggcgagcggt atcagctcac tcaaaggcgg taatacggtt atccacagaa   6540

tcaggggata acgcaggaaa gaacatgtga gcaaaaggcc agcaaaaggc caggaaccgt   6600

aaaaaggccg cgttgctggc gtttttccat aggctccgcc cccctgacga gcatcacaaa   6660

aatcgacgct caagtcagag gtggcgaaac ccgacaggac tataaagata ccaggcgttt   6720

ccccctggaa gctccctcgt gcgctctcct gttccgaccc tgccgcttac cggatacctg   6780

tccgcctttc tcccttcggg aagcgtggcg ctttctcata gctcacgctg taggtatctc   6840

agttcggtgt aggtcgttcg ctccaagctg ggctgtgtgc acgaaccccc cgttcagccc   6900

gaccgctgcg ccttatccgg taactatcgt cttgagtcca acccggtaag acacgactta   6960

tcgccactgg cagcagccac tggtaacagg attagcagag cgaggtatgt aggcggtgct   7020

acagagttct tgaagtggtg gcctaactac ggctacacta gaaggacagt atttggtatc   7080

tgcgctctgc tgaagccagt taccttcgga aaaagagttg gtagctcttg atccggcaaa   7140

caaaccaccg ctggtagcgg tggttttttt gtttgcaagc agcagattac gcgcagaaaa   7200

aaaggatctc aagaagatcc tttgatcttt tctacggggt ctgacgctca              7250
```

```
<210> SEQ ID NO 16
<211> LENGTH: 7672
<212> TYPE: DNA
<213> ORGANISM: Artificial Sequence
<220> FEATURE:
<223> OTHER INFORMATION: Synthetic Sequence - Plasmid  Vector 2xgRNA Can
      cross
<220> FEATURE:
<221> NAME/KEY: gene
<222> LOCATION: (133)..(993)
<223> OTHER INFORMATION: AmpR
<220> FEATURE:
<221> NAME/KEY: promoter
<222> LOCATION: (994)..(1098)
<223> OTHER INFORMATION: AmpR promoter
<220> FEATURE:
<221> NAME/KEY: rep_origin
<222> LOCATION: (1125)..(2467)
<223> OTHER INFORMATION: 2 micro ori
```

```
<220> FEATURE:
<221> NAME/KEY: terminator
<222> LOCATION: (2539)..(2552)
<223> OTHER INFORMATION: Sup4 term
<220> FEATURE:
<221> NAME/KEY: misc_structure
<222> LOCATION: (2555)..(2637)
<223> OTHER INFORMATION: tracrRNA
<220> FEATURE:
<221> NAME/KEY: misc_feature
<222> LOCATION: (2638)..(2657)
<223> OTHER INFORMATION: target1R
<220> FEATURE:
<221> NAME/KEY: promoter
<222> LOCATION: (2658)..(2926)
<223> OTHER INFORMATION: SNR52 promoter
<220> FEATURE:
<221> NAME/KEY: misc_feature
<222> LOCATION: (2943)..(3416)
<223> OTHER INFORMATION: Can1_Left arm
<220> FEATURE:
<221> NAME/KEY: promoter
<222> LOCATION: (3653)..(3868)
<223> OTHER INFORMATION: URA3 promoter
<220> FEATURE:
<221> NAME/KEY: gene
<222> LOCATION: (3869)..(4672)
<223> OTHER INFORMATION: URA3
<220> FEATURE:
<221> NAME/KEY: rep_origin
<222> LOCATION: (4803)..(5258)
<223> OTHER INFORMATION: f1 ori
<220> FEATURE:
<221> NAME/KEY: misc_feature
<222> LOCATION: (5476)..(5929)
<223> OTHER INFORMATION: Can1_Right Arm
<220> FEATURE:
<221> NAME/KEY: terminator
<222> LOCATION: (5941)..(6188)
<223> OTHER INFORMATION: CYC1 terminator
<220> FEATURE:
<221> NAME/KEY: terminator
<222> LOCATION: (6194)..(6207)
<223> OTHER INFORMATION: Sup4 term
<220> FEATURE:
<221> NAME/KEY: misc_structure
<222> LOCATION: (6210)..(6292)
<223> OTHER INFORMATION: tracrRNA
<220> FEATURE:
<221> NAME/KEY: misc_feature
<222> LOCATION: (6293)..(6312)
<223> OTHER INFORMATION: target2R
<220> FEATURE:
<221> NAME/KEY: promoter
<222> LOCATION: (6313)..(6581)
<223> OTHER INFORMATION: SNR52 promoter
<220> FEATURE:
<221> NAME/KEY: rep_origin
<222> LOCATION: (7046)..(7634)
<223> OTHER INFORMATION: ori

<400> SEQUENCE: 16

gtggaacgaa aactcacgtt aagggatttt ggtcatgaga ttatcaaaaa ggatcttcac     60

ctagatcctt ttaaattaaa aatgaagttt taaatcaatc taaagtatat atgagtaaac    120

ttggtctgac agttaccaat gcttaatcag tgaggcacct atctcagcga tctgtctatt    180

tcgttcatcc atagttgcct gactccccgt cgtgtagata actacgatac gggagggctt    240

accatctggc cccagtgctg caatgatacc gcgagaccca cgctcaccgg ctccagattt    300

atcagcaata aaccagccag ccggaagggc cgagcgcaga agtggtcctg caactttatc    360

cgcctccatc cagtctatta attgttgccg ggaagctaga gtaagtagtt cgccagttaa    420

tagtttgcgc aacgttgttg ccattgctac aggcatcgtg gtgtcacgct cgtcgtttgg    480
```

```
tatggcttca ttcagctccg gttcccaacg atcaaggcga gttacatgat cccccatgtt    540
gtgcaaaaaa gcggttagct ccttcggtcc tccgatcgtt gtcagaagta agttggccgc    600
agtgttatca ctcatggtta tggcagcact gcataattct cttactgtca tgccatccgt    660
aagatgcttt tctgtgactg gtgagtactc aaccaagtca ttctgagaat agtgtatgcg    720
gcgaccgagt tgctcttgcc cggcgtcaat acgggataat accgcgccac atagcagaac    780
tttaaaagtg ctcatcattg gaaaacgttc ttcggggcga aaactctcaa ggatcttacc    840
gctgttgaga tccagttcga tgtaacccac tcgtgcaccc aactgatctt cagcatcttt    900
tactttcacc agcgtttctg ggtgagcaaa aacaggaagg caaaatgccg caaaaaaggg    960
aataagggcg acacggaaat gttgaatact catactcttc ctttttcaat attattgaag   1020
catttatcag ggttattgtc tcatgagcgg atacatattt gaatgtattt agaaaaataa   1080
acaaataggg gttccgcgca catttccccg aaaagtgcca cctgaacgaa gcatctgtgc   1140
ttcattttgt agaacaaaaa tgcaacgcga gagcgctaat ttttcaaaca aagaatctga   1200
gctgcatttt tacagaacag aaatgcaacg cgaaagcgct attttaccaa cgaagaatct   1260
gtgcttcatt tttgtaaaac aaaaatgcaa cgcgagagcg ctaatttttc aaacaaagaa   1320
tctgagctgc atttttacag aacagaaatg caacgcgaga gcgctatttt accaacaaag   1380
aatctatact tcttttttgt tctacaaaaa tgcatcccga gagcgctatt tttctaacaa   1440
agcatcttag attacttttt ttctcctttg tgcgctctat aatgcagtct cttgataact   1500
ttttgcactg taggtccgtt aaggttagaa gaaggctact ttggtgtcta ttttctcttc   1560
cataaaaaaa gcctgactcc acttcccgcg tttactgatt actagcgaag ctgcgggtgc   1620
atttttcaa gataaaggca tccccgatta tattctatac cgatgtggat tgcgcatact   1680
ttgtgaacag aaagtgatag cgttgatgat tcttcattgg tcagaaaatt atgaacggtt   1740
tcttctattt tgtctctata tactacgtat aggaaatgtt tacattttcg tattgttttc   1800
gattcactct atgaatagtt cttactacaa tttttttgtc taaagagtaa tactagagat   1860
aaacataaaa aatgtagagg tcgagtttag atgcaagttc aaggagcgaa aggtggatgg   1920
gtaggttata tagggatata gcacagagat atatagcaaa gagatacttt tgagcaatgt   1980
ttgtggaagc ggtattcgca atattttagt agctcgttac agtccggtgc gtttttggtt   2040
ttttgaaagt gcgtcttcag agcgcttttg gttttcaaaa gcgctctgaa gttcctatac   2100
tttctagaga ataggaactt cggaatagga acttcaaagc gtttccgaaa acgagcgctt   2160
ccgaaaatgc aacgcgagct gcgcacatac agctcactgt tcacgtcgca cctatatctg   2220
cgtgttgcct gtatatatat atacatgaga agaacggcat agtgcgtgtt tatgcttaaa   2280
tgcgtactta tatgcgtcta tttatgtagg atgaaaggta gtctagtacc tcctgtgata   2340
ttatcccatt ccatgcgggg tatcgtatgc ttccttcagc actacccttt agctgttcta   2400
tatgctgcca ctcctcaatt ggattagtct catccttcaa tgctatcatt tcctttgata   2460
ttggatcata ctaagaaacc attattatca tgacattaac ctataaaaat aggcgcatgt   2520
cgactacccg ggaactcgag acataaaaaa caaaaaaagc accaccgact cggtgccact   2580
ttttcaagtt gataacggac tagccttatt ttaacttgct atttctagct ctaaaacgaa   2640
aaggggatcc tattgacgat catttatctt tcactgcgga gaagtttcga acgccgaaac   2700
atgcgcacca actttcactt ctacagcgtt tgaccaaaat cttttgaaca gaacattgta   2760
gggtgtgaaa aaatgcgcac ctttaccgct agcccaagag ggcactacaa aatctagagt   2820
tgtacttcaa acgtacatgt aatcaccttg tatatactcg aaagaaaaca tcaagtttct   2880
```

```
gtataaatat gagtgaaagc ataatcatac attatctttt caaagaattc accggtgcat   2940
gcttattagc cttgatagtg ctgaaaaaaa gaaaaaaaac aaaaaaaaga aataaaataa   3000
cggcaaacag caaaggccac agaaccgtat tcatgttact tctgcaatat caatcactta   3060
ctggcaagtg cgtataaatt aaacctattt ctttatcatc atatttactt atatctttaa   3120
cagattccaa accctaaagt gtccgaattt tcaatagggc gaacttgaag aataaccaag   3180
gtcaataata tatcttttag tataaccctg aaatttgccc tatagaaatc tagggtttct   3240
gtgtggtttc cgggtgagtc atacggcttt tttgaatttc tttttttgca gttgtctcta   3300
tcaatgaaaa tttcgaggaa gacgataagg ttaagataag tagataagag aatgatacga   3360
gataaagcac aaattagcag aaagaagagt ggttgcgaac agagtaaacc gaatcagacg   3420
tcagacctag gtcatgccga ggccctttcg tctcgcgcgt ttcggtgatg acggtgaaaa   3480
cctctgacac atgcagctcc cggagacggt cacagcttgt ctgtaagcgg atgccgggag   3540
cagacaagcc cgtcagggcg cgtcagcggg tgttggcggg tgtcggggct ggcttaacta   3600
tgcggcatca gagcagattg tactgagagt gcaccatacc acagcttttc aattcaattc   3660
atcatttttt ttttattctt ttttttgatt tcggtttcct tgaaattttt ttgattcggt   3720
aatctccgaa cagaaggaag aacgaaggaa ggagcacaga cttagattgg tatatatacg   3780
catatgtagt gttgaagaaa catgaaattg cccagtattc ttaacccaac tgcacagaac   3840
aaaaacctgc aggaaacgaa gataaatcat gtcgaaagct acatataagg aacgtgctgc   3900
tactcatcct agtcctgttg ctgccaagct atttaatatc atgcacgaaa agcaaacaaa   3960
cttgtgtgct tcattggatg ttcgtaccac caaggaatta ctggagttag ttgaagcatt   4020
aggtcccaaa atttgtttac taaaaacaca tgtggatatc ttgactgatt tttccatgga   4080
gggcacagtt aagccgctaa aggcattatc cgccaagtac aatttttac tcttcgaaga   4140
cagaaaattt gctgacattg gtaatacagt caaattgcag tactctgcgg gtgtatacag   4200
aatagcagaa tgggcagaca ttacgaatgc acacggtgtg gtgggcccag gtattgttag   4260
cggtttgaag caggcggcag aagaagtaac aaaggaacct agaggccttt tgatgttagc   4320
agaattgtca tgcaagggct ccctatctac tggagaatat actaagggta ctgttgacat   4380
tgcgaagagc gacaaagatt ttgttatcgg ctttattgct caaagagaca tgggtggaag   4440
agatgaaggt tacgattggt tgattatgac acccggtgtg ggtttagatg acaagggaga   4500
cgcattgggt caacagtata gaaccgtgga tgatgtggtc tctacaggat ctgacattat   4560
tattgttgga agaggactat ttgcaaaggg aagggatgct aaggtagagg gtgaacgtta   4620
cagaaaagca ggctgggaag catatttgag aagatgcggc cagcaaaact aaaaaactgt   4680
attataagta aatgcatgta tactaaactc acaaattaga gcttcaattt aattatatca   4740
gttattaccc tatgcggtgt gaaataccgc acagatgcgt aaggagaaaa taccgcatca   4800
ggaaattgta aacgttaata ttttgttaaa attcgcgtta aatttttgtt aaatcagctc   4860
atttttaac caataggccg aaatcggcaa aatcccttat aaatcaaaag aatagaccga   4920
gatagggttg agtgttgttc cagtttggaa caagagtcca ctattaaaga acgtggactc   4980
caacgtcaaa gggcgaaaaa ccgtctatca gggcgatggc ccactacgtg aaccatcacc   5040
ctaatcaagt tttttggggt cgaggtgccg taaagcacta aatcggaacc ctaaagggag   5100
cccccgattt agagcttgac ggggaaagcc ggcgaacgtg gcgagaaagg aagggaagaa   5160
agcgaaagga gcgggcgcta gggcgctggc aagtgtagcg gtcacgctgc gcgtaaccac   5220
```

```
cacacccgcc gcgcttaatg cgccgctaca gggcgcgtcg cgccattcgc cattcaggct   5280
gcgcaactgt tgggaagggc gatcggtgcg ggcctcttcg ctattacgcc agctggcgaa   5340
agggggatgt gctgcaaggc gattaagttg ggtaacgcca gggttttccc agtcacgacg   5400
ttgtaaaacg acggccagtg agcgcgcgta atacgactca ctatagggcg aattgggtac   5460
tcctaggtta attaagataa tgtctgagtt aggtgagtat tctaaattag aaaacaaaga   5520
gcttagaacg gagtttgaat tgacaaattt tccttttcca ggcacaactg ataacgactc   5580
cgatgacgga agccaagggc agaactcttt gaatatcatt actcctgaca tggatgatac   5640
tctggttaat gatgtacttc gagaaaacga taaaaagtct agtatgagaa tggcttttat   5700
gaatctagca aactctattc ttggtgccgg aataattact cagccgttcg cgatcaaaaa   5760
tgctggtata ttaggcgggc tattatcata cgtagccctc ggatttatag ttgattggac   5820
gttaagactt attgtcatta acttgactct tgctggcaag agaacatacc agggtacggt   5880
cgaacatgta atgggtaaaa aagggaaatt gctgattcta tttacaaact ggtaccggcc   5940
gcaaattaaa gccttcgagc gtcccaaaac cttctcaagc aaggttttca gtataatgtt   6000
acatgcgtac acgcgtctgt acagaaaaaa aagaaaaatt tgaaatataa ataacgttct   6060
taatactaac ataactataa aaaaataaat agggacctag acttcaggtt gtctaactcc   6120
ttcctttcg gttagagcgg atgtgggggg agggcgtgaa cgtaagcgtg acataactaa   6180
ttacatgact cgaagacata aaaaacaaaa aaagcaccac cgactcggtg ccactttttc   6240
aagttgataa cggactagcc ttattttaac ttgctatttc tagctctaaa acgaaaaggg   6300
gatcctattg acgatcattt atctttcact gcggagaagt ttcgaacgcc gaaacatgcg   6360
caccaacttt cacttctaca gcgtttgacc aaaatctttt gaacagaaca ttgtagggtg   6420
tgaaaaaatg cgcaccttta ccgctagccc aagagggcac tacaaaatct agagttgtac   6480
ttcaaacgta catgtaatca ccttgtatat actcgaaaga aaacatcaag tttctgtata   6540
aatatgagtg aaagcataat catacattat cttttcaaag aagctccagc ttttgttccc   6600
tttagtgatc acgtccggat tgcggccgct tggcgtaatc atggtcatag ctgtttcctg   6660
tgtgaaattg ttatccgctc acaattccac acaacatacg agccggaagc ataaagtgta   6720
aagcctgggg tgcctaatga gtgagctaac tcacattaat tgcgttgcgc tcactgcccg   6780
ctttccagtc gggaaacctg tcgtgccagc tgcattaatg aatcggccaa cgcgcgggga   6840
gaggcggttt gcgtattggg cgctcttccg cttcctcgct cactgactcg ctgcgctcgg   6900
tcgttcggct gcggcgagcg gtatcagctc actcaaaggc ggtaatacgg ttatccacag   6960
aatcagggga taacgcagga aagaacatgt gagcaaaagg ccagcaaaag gccaggaacc   7020
gtaaaaaggc cgcgttgctg gcgtttttcc ataggctccg cccccctgac gagcatcaca   7080
aaaatcgacg ctcaagtcag aggtggcgaa acccgacagg actataaaga taccaggcgt   7140
ttccccctgg aagctccctc gtgcgctctc ctgttccgac cctgccgctt accggatacc   7200
tgtccgcctt tctcccttcg ggaagcgtgg cgctttctca tagctcacgc tgtaggtatc   7260
tcagttcggt gtaggtcgtt cgctccaagc tgggctgtgt gcacgaaccc cccgttcagc   7320
ccgaccgctg cgccttatcc ggtaactatc gtcttgagtc caacccggta agacacgact   7380
tatcgccact ggcagcagcc actggtaaca ggattagcag agcgaggtat gtaggcggtg   7440
ctacagagtt cttgaagtgg tggcctaact acggctacac tagaaggaca gtatttggta   7500
tctgcgctct gctgaagcca gttaccttcg gaaaaagagt tggtagctct tgatccggca   7560
aacaaaccac cgctggtagc ggtggttttt ttgtttgcaa gcagcagatt acgcgcagaa   7620
```

aaaaaggatc tcaagaagat cctttgatct tttctacggg gtctgacgct ca 7672

<210> SEQ ID NO 17
<211> LENGTH: 20
<212> TYPE: DNA
<213> ORGANISM: Saccharomyces cerevisiae

<400> SEQUENCE: 17
cgaacagagt aaaccgaatc 20

<210> SEQ ID NO 18
<211> LENGTH: 20
<212> TYPE: DNA
<213> ORGANISM: Saccharomyces cerevisiae

<400> SEQUENCE: 18
agcactatca aggctaataa 20

<210> SEQ ID NO 19
<211> LENGTH: 20
<212> TYPE: DNA
<213> ORGANISM: Saccharomyces cerevisiae

<400> SEQUENCE: 19
gcgaacttga agaataacca 20

<210> SEQ ID NO 20
<211> LENGTH: 20
<212> TYPE: DNA
<213> ORGANISM: Saccharomyces cerevisiae

<400> SEQUENCE: 20
tcacctaact cagacattat 20

<210> SEQ ID NO 21
<211> LENGTH: 20
<212> TYPE: DNA
<213> ORGANISM: Saccharomyces cerevisiae

<400> SEQUENCE: 21
ttgctgattc tatttacaaa 20

<210> SEQ ID NO 22
<211> LENGTH: 20
<212> TYPE: DNA
<213> ORGANISM: Saccharomyces cerevisiae

<400> SEQUENCE: 22
gcaaactcta ttcttggtgc 20

<210> SEQ ID NO 23
<211> LENGTH: 20
<212> TYPE: DNA
<213> ORGANISM: Saccharomyces cerevisiae

<400> SEQUENCE: 23
accagagtat catccatgtc 20

<210> SEQ ID NO 24
<211> LENGTH: 20
<212> TYPE: DNA
<213> ORGANISM: Saccharomyces cerevisiae

<400> SEQUENCE: 24
aattcggaca ctttagggtt 20

<210> SEQ ID NO 25
<211> LENGTH: 20
<212> TYPE: DNA
<213> ORGANISM: Saccharomyces cerevisiae

<400> SEQUENCE: 25
agatattata cctggacccc 20

<210> SEQ ID NO 26
<211> LENGTH: 23
<212> TYPE: DNA
<213> ORGANISM: Saccharomyces cerevisiae

<400> SEQUENCE: 26
cccagttgga ttccgttatt gga 23

<210> SEQ ID NO 27
<211> LENGTH: 23
<212> TYPE: DNA
<213> ORGANISM: Saccharomyces cerevisiae

<400> SEQUENCE: 27
ccaggtataa tatctaagga taa 23

<210> SEQ ID NO 28
<211> LENGTH: 94
<212> TYPE: DNA
<213> ORGANISM: Artificial Sequence
<220> FEATURE:
<223> OTHER INFORMATION: Synthetic Sequence - Part of Plasmid Vector 1059(Can1-7R) or Plasmid Vector 1148(Can1-11R)

<400> SEQUENCE: 28
ggttatgcta tgcattccgt tattggtgaa acccaggtgc ctggggtcca ggtataatat 60
cttaggataa aaacgaaggg aggttcttag gttg 94

<210> SEQ ID NO 29
<211> LENGTH: 94
<212> TYPE: DNA
<213> ORGANISM: Saccharomyces cerevisiae

<400> SEQUENCE: 29
ccggcccagt tggattccgt tattggagaa acccaggtgc ctggggtcca ggtataatat 60
ctaaggataa aaacgaaggg aggttcttag gttg 94

<210> SEQ ID NO 30
<211> LENGTH: 23
<212> TYPE: DNA
<213> ORGANISM: Saccharomyces cerevisiae

<400> SEQUENCE: 30
ccaggtataa tatctaagga taa 23

<210> SEQ ID NO 31
<211> LENGTH: 23
<212> TYPE: DNA
<213> ORGANISM: Saccharomyces cerevisiae

<400> SEQUENCE: 31
ccgttattgg agaaacccag gtg 23

<210> SEQ ID NO 32
<211> LENGTH: 70
<212> TYPE: DNA
<213> ORGANISM: Artificial Sequence
<220> FEATURE:
<223> OTHER INFORMATION: Synthetic Sequence - donor DNA

<400> SEQUENCE: 32
gcgctaccgg actcagatct accggcccag ttggaatgta ggtggtgagc aagggcgagg 60
agctgttcac 70

<210> SEQ ID NO 33
<211> LENGTH: 70
<212> TYPE: DNA
<213> ORGANISM: Artificial Sequence
<220> FEATURE:
<223> OTHER INFORMATION: Synthetic Sequence - donor DNA

<400> SEQUENCE: 33
gcgctaccgg actcagatct accggcccag ttggaatgta gatggtgagc aagggcgagg 60
agctgttcac 70

<210> SEQ ID NO 34
<211> LENGTH: 70
<212> TYPE: DNA
<213> ORGANISM: Artificial Sequence
<220> FEATURE:
<223> OTHER INFORMATION: Synthetic Sequence - donor DNA

<400> SEQUENCE: 34
gcgctaccgg actcagatct acgggcccag ttggaatgta gatggtgagc aagggcgagg 60
agctgttcac 70

<210> SEQ ID NO 35
<211> LENGTH: 70
<212> TYPE: DNA
<213> ORGANISM: Artificial Sequence
<220> FEATURE:
<223> OTHER INFORMATION: Synthetic Sequence - donor DNA

<400> SEQUENCE: 35
gtgaacagct cctcgccctt gctcaccacc tacattccaa ctgggccggt agatctgagt 60
ccggtagcgc 70

<210> SEQ ID NO 36
<211> LENGTH: 70
<212> TYPE: DNA
<213> ORGANISM: Artificial Sequence
<220> FEATURE:
<223> OTHER INFORMATION: Synthetic Sequence - donor DNA

<400> SEQUENCE: 36
gtgaacagct cctcgccctt gctcaccatc tacattccaa ctgggccggt agatctgagt 60
ccggtagcgc 70

<210> SEQ ID NO 37
<211> LENGTH: 70
<212> TYPE: DNA
<213> ORGANISM: Artificial Sequence
<220> FEATURE:
<223> OTHER INFORMATION: Synthetic Sequence - donor DNA

<400> SEQUENCE: 37
gtgaacagct cctcgccctt gctcaccatc tacattccaa ctgggcccgt agatctgagt 60
ccggtagcgc 70

<210> SEQ ID NO 38
<211> LENGTH: 70
<212> TYPE: DNA
<213> ORGANISM: Artificial Sequence
<220> FEATURE:
<223> OTHER INFORMATION: Synthetic Sequence - donor DNA

<400> SEQUENCE: 38
ccgtcagatc cgctagcgct accggactca gatctaccgg cccagttgga atgtagatgg 60
tgagcaaggg 70

<210> SEQ ID NO 39
<211> LENGTH: 70
<212> TYPE: DNA
<213> ORGANISM: Artificial Sequence
<220> FEATURE:
<223> OTHER INFORMATION: Synthetic Sequence - donor DNA

<400> SEQUENCE: 39
gatctaccgg cccagttgga atgtagatgg tgagcaaggg cgaggagctg ttcaccgggg 60
tggtgcccat 70

<210> SEQ ID NO 40
<211> LENGTH: 50
<212> TYPE: DNA
<213> ORGANISM: Artificial Sequence
<220> FEATURE:
<223> OTHER INFORMATION: Synthetic Sequence - donor DNA

<400> SEQUENCE: 40
actcagatct accggcccag ttggaatgta gatggtgagc aagggcgagg 50

<210> SEQ ID NO 41
<211> LENGTH: 50
<212> TYPE: DNA
<213> ORGANISM: Artificial Sequence
<220> FEATURE:
<223> OTHER INFORMATION: Synthetic Sequence - donor DNA

<400> SEQUENCE: 41
cctcgccctt gctcaccatc tacattccaa ctgggccggt agatctgagt 50

<210> SEQ ID NO 42
<211> LENGTH: 6189
<212> TYPE: DNA
<213> ORGANISM: Artificial Sequence
<220> FEATURE:
<223> OTHER INFORMATION: Synthetic Sequence - Vector
SY4(H1_sgRNA,CMV_mEGFP)(Reporter plasmid)
<220> FEATURE:
<221> NAME/KEY: promoter
<222> LOCATION: (263)..(491)
<223> OTHER INFORMATION: H1 promoter
<220> FEATURE:
<221> NAME/KEY: misc_structure
<222> LOCATION: (512)..(587)
<223> OTHER INFORMATION: gRNA scaffold
<220> FEATURE:
<221> NAME/KEY: enhancer
<222> LOCATION: (602)..(981)
<223> OTHER INFORMATION: CMV enhancer
<220> FEATURE:
<221> NAME/KEY: promoter
<222> LOCATION: (982)..(1185)
<223> OTHER INFORMATION: CMV promoter
<220> FEATURE:
<221> NAME/KEY: misc_feature
<222> LOCATION: (1231)..(1250)
<223> OTHER INFORMATION: KI_target2
<220> FEATURE:
<221> NAME/KEY: misc_feature
<222> LOCATION: (1236)..(1255)
<223> OTHER INFORMATION: eGFP switch target
<220> FEATURE:
<221> NAME/KEY: misc_feature
<222> LOCATION: (1247)..(1249)
<223> OTHER INFORMATION: Start codon
<220> FEATURE:
<221> NAME/KEY: gene
<222> LOCATION: (1254)..(1969)
<223> OTHER INFORMATION: EGFP
<220> FEATURE:
<221> NAME/KEY: polyA_signal
<222> LOCATION: (2012)..(2236)
<223> OTHER INFORMATION: bGH poly(A)
<220> FEATURE:
<221> NAME/KEY: rep_origin
<222> LOCATION: (2282)..(2710)
<223> OTHER INFORMATION: f1 ori
<220> FEATURE:
<221> NAME/KEY: promoter
<222> LOCATION: (2724)..(3053)
<223> OTHER INFORMATION: SV40 promoter
<220> FEATURE:
<221> NAME/KEY: rep_origin
<222> LOCATION: (2904)..(3039)
<223> OTHER INFORMATION: SV40 ori
<220> FEATURE:
<221> NAME/KEY: gene
<222> LOCATION: (3070)..(3669)
<223> OTHER INFORMATION: PuroR
<220> FEATURE:
<221> NAME/KEY: misc_structure
<222> LOCATION: (3683)..(4271)
<223> OTHER INFORMATION: WPRE
<220> FEATURE:
<221> NAME/KEY: rep_origin
<222> LOCATION: (4468)..(5053)
<223> OTHER INFORMATION: ori
<220> FEATURE:
<221> NAME/KEY: gene
<222> LOCATION: (5224)..(6084)
<223> OTHER INFORMATION: AmpR
<220> FEATURE:
<221> NAME/KEY: promoter
<222> LOCATION: (6085)..(6189)
<223> OTHER INFORMATION: AmpR promoter

<400> SEQUENCE: 42
cacatttccc cgaaaagtgc cacctgacgt cgacggatcg ggagatctcc cgatccccta 60
tggtgcactc tcagtacaat ctgctctgat gccgcatagt taagccagta tctgctccct 120
gcttgtgtgt tggaggtcgc tgagtagtgc gcgagcaaaa tttaagctac aacaaggcaa 180
ggcttgaccg acaattgcat gaagaatctg cttagggtta ggcgttttgc gctgcttcgc 240
gatgtacggg ccagatatac gcaattcgaa cgctgacgtc atcaacccgc tccaaggaat 300
cgcgggccca gtgtcactag gcgggaacac ccagcgcgcg tgcgccctgg caggaagatg 360
gctgtgaggg acaggggagt ggcgccctgc aatatttgca tgtcgctatg tgttctggga 420
aatcaccata aacgtgaaat gtctttggat ttgggaatct tataagttct gtatgaggac 480
cacagatccc ccacctacat tccaactggg cgttttagag ctagaaatag caagttaaaa 540
taaggctagt ccgttatcaa cttgaaaaag tggcaccgag tcggtgcttt ttttacgcgt 600

```
tgacattgat tattgactag ttattaatag taatcaatta cggggtcatt agttcatagc    660
ccatatatgg agttccgcgt tacataactt acggtaaatg gcccgcctgg ctgaccgccc    720
aacgaccccc gcccattgac gtcaataatg acgtatgttc ccatagtaac gccaataggg    780
actttccatt gacgtcaatg ggtggagtat ttacggtaaa ctgcccactt ggcagtacat    840
caagtgtatc atatgccaag tacgccccct attgacgtca atgacggtaa atggcccgcc    900
tggcattatg cccagtacat gaccttatgg gactttccta cttggcagta catctacgta    960
ttagtcatcg ctattaccat ggtgatgcgg ttttggcagt acatcaatgg gcgtggatag   1020
cggtttgact cacggggatt tccaagtctc caccccattg acgtcaatgg gagtttgttt   1080
tggcaccaaa atcaacggga ctttccaaaa tgtcgtaaca actccgcccc attgacgcaa   1140
atgggcggta ggcgtgtacg gtgggaggtc tatataagca gagctggttt agtgaaccgt   1200
cagatccgct agcgctaccg gactcagatc taccggccca gttggaatgt aggtggtgag   1260
caagggcgag gagctgttca ccggggtggt gcccatcctg gtcgagctgg acggcgacgt   1320
aaacggccac aagttcagcg tgtccggcga gggcgagggc gatgccacct acggcaagct   1380
gaccctgaag ttcatctgca ccaccggcaa gctgcccgtg ccctggccca ccctcgtgac   1440
caccttcacc tacggcgtgc agtgcttcag ccgctacccc gaccacatga agcagcacga   1500
cttcttcaag tccgccatgc ccgaaggcta cgtccaggag cgcaccatct tcttcaagga   1560
cgacggcaac tacaagaccc gcgccgaggt gaagttcgag ggcgacaccc tggtgaaccg   1620
catcgagctg aagggcatcg acttcaagga ggacggcaac atcctggggc acaagctgga   1680
gtacaactac aacagccaca acgtctatat catggccgac aagcagaaga acggcatcaa   1740
ggtgaacttc aagatccgcc acaacatcga ggacggcagc gtgcagctcg ccgaccacta   1800
ccagcagaac acccccatcg gcgacggccc cgtgctgctg cccgacaacc actacctgag   1860
cacccagtcc gccctgagca aagaccccaa cgagaagcgc gatcacatgg tcctgctgga   1920
gttcgtgacc gccgccggga tcactcacgg catggacgag ctgtacaagg ctcgagctca   1980
agcttaagtt taaaccgctg atcagcctcg actgtgcctt ctagttgcca gccatctgtt   2040
gtttgcccct cccccgtgcc ttccttgacc ctggaaggtg ccactcccac tgtcctttcc   2100
taataaaatg aggaaattgc atcgcattgt ctgagtaggt gtcattctat tctggggggt   2160
ggggtggggc aggacagcaa gggggaggat tgggaagaca atagcaggca tgctggggat   2220
gcggtgggct ctatggcttc tgaggcggaa agaaccagct ggggctctag ggggtatccc   2280
cacgcgccct gtagcggcgc attaagcgcg gcgggtgtgg tggttacgcg cagcgtgacc   2340
gctacacttg ccagcgccct agcgcccgct cctttcgctt tcttcccttc ctttctcgcc   2400
acgttcgccg gctttccccg tcaagctcta aatcgggggc tccctttagg gttccgattt   2460
agtgctttac ggcacctcga ccccaaaaaa cttgattagg gtgatggttc acgtagtggg   2520
ccatcgccct gatagacggt ttttcgccct ttgacgttgg agtccacgtt ctttaatagt   2580
ggactcttgt tccaaactgg aacaacactc aaccctatct cggtctattc ttttgattta   2640
taagggattt tgccgatttc ggcctattgg ttaaaaaatg agctgattta acaaaaattt   2700
aacgcgaatt aattctgtgg aatgtgtgtc agttagggtg tggaaagtcc ccaggctccc   2760
cagcaggcag aagtatgcaa agcatgcatc tcaattagtc agcaaccagg tgtggaaagt   2820
ccccaggctc cccagcaggc agaagtatgc aaagcatgca tctcaattag tcagcaacca   2880
tagtcccgcc cctaactccg cccatcccgc ccctaactcc gcccagttcc gcccattctc   2940
cgccccatgg ctgactaatt ttttttattt atgcagaggc cgaggccgcc tctgcctctg   3000
```

```
agctattcca gaagtagtga ggaggctttt ttggaggcct aggcttttgc aaaaagctcc   3060
cggtctagaa tgaccgagta caagcccacg gtgcgcctcg ccacccgcga cgacgtcccc   3120
cgggccgtac gcaccctcgc cgccgcgttc gccgactacc ccgccacgcg ccacaccgtc   3180
gacccggacc gccacatcga gcgggtcacc gagctgcaag aactcttcct cacgcgcgtc   3240
gggctcgaca tcggcaaggt gtgggtcgcg gacgacggcg ccgcggtggc ggtctggacc   3300
acgccggaga gcgtcgaagc gggggcggtg ttcgccgaga tcggcccgcg catggccgag   3360
ttgagcggtt cccggctggc cgcgcagcaa cagatggaag gcctcctggc gccgcaccgg   3420
cccaaggagc ccgcgtggtt cctggccacc gtcggcgtct cgcccgacca ccagggcaag   3480
ggtctgggca gcgccgtcgt gctccccgga gtggaggcgg ccgagcgcgc cggggtgccc   3540
gccttcctgg agacctccgc gccccgcaac ctccccttct acgagcggct cggcttcacc   3600
gtcaccgccg acgtcgaggt gcccgaagga ccgcgcacct ggtgcatgac ccgcaagccc   3660
ggtgcctaga cgcgtctgga acaatcaacc tctggattac aaaatttgtg aaagattgac   3720
tggtattctt aactatgttg ctccttttac gctatgtgga tacgctgctt taatgccttt   3780
gtatcatgct attgcttccc gtatggcttt cattttctcc tccttgtata aatcctggtt   3840
gctgtctctt tatgaggagt tgtggcccgt tgtcaggcaa cgtggcgtgg tgtgcactgt   3900
gtttgctgac gcaaccccca ctggttgggg cattgccacc acctgtcagc tcctttccgg   3960
gactttcgct ttccccctcc ctattgccac ggcggaactc atcgccgcct gccttgcccg   4020
ctgctggaca ggggctcggc tgttgggcac tgacaattcc gtggtgttgt cggggaagct   4080
gacgtccttt ccatggctgc tcgcctgtgt tgccacctgg attctgcgcg ggacgtcctt   4140
ctgctacgtc ccttcggccc tcaatccagc ggaccttcct tcccgcggcc tgctgccggc   4200
tctgcggcct cttccgcgtc ttcgccttcg ccctcagacg agtcggatct ccctttgggc   4260
cgcctccccg cctggaatta attctgcggc cgcttcctcg ctcactgact cgctgcgctc   4320
ggtcgttcgg ctgcggcgag cggtatcagc tcactcaaag gcggtaatac ggttatccac   4380
agaatcaggg gataacgcag gaaagaacat gtgagcaaaa ggccagcaaa aggccaggaa   4440
ccgtaaaaag gccgcgttgc tggcgttttt ccataggctc cgcccccctg acgagcatca   4500
caaaaatcga cgctcaagtc agaggtggcg aaacccgaca ggactataaa gataccaggc   4560
gtttccccct ggaagctccc tcgtgcgctc tcctgttccg accctgccgc ttaccggata   4620
cctgtccgcc tttctccctt cgggaagcgt ggcgctttct catagctcac gctgtaggta   4680
tctcagttcg gtgtaggtcg ttcgctccaa gctgggctgt gtgcacgaac cccccgttca   4740
gcccgaccgc tgcgccttat ccggtaacta tcgtcttgag tccaacccgg taagacacga   4800
cttatcgcca ctggcagcag ccactggtaa caggattagc agagcgaggt atgtaggcgg   4860
tgctacagag ttcttgaagt ggtggcctaa ctacggctac actagaagaa cagtatttgg   4920
tatctgcgct ctgctgaagc cagttacctt cggaaaaaga gttggtagct cttgatccgg   4980
caaacaaacc accgctggta gcggtttttt tgtttgcaag cagcagatta cgcgcagaaa   5040
aaaaggatct caagaagatc ctttgatctt ttctacgggg tctgacgctc agtggaacga   5100
aaactcacgt taagggattt tggtcatgag attatcaaaa aggatcttca cctagatcct   5160
tttaaattaa aaatgaagtt ttaaatcaat ctaaagtata tatgagtaaa cttggtctga   5220
cagttaccaa tgcttaatca gtgaggcacc tatctcagcg atctgtctat ttcgttcatc   5280
catagttgcc tgactccccg tcgtgtagat aactacgata cgggagggct taccatctgg   5340
```

```
ccccagtgct gcaatgatac cgcgagaccc acgctcaccg gctccagatt tatcagcaat   5400

aaaccagcca gccggaaggg ccgagcgcag aagtggtcct gcaactttat ccgcctccat   5460

ccagtctatt aattgttgcc gggaagctag agtaagtagt tcgccagtta atagtttgcg   5520

caacgttgtt gccattgcta caggcatcgt ggtgtcacgc tcgtcgtttg gtatggcttc   5580

attcagctcc ggttcccaac gatcaaggcg agttacatga tcccccatgt tgtgcaaaaa   5640

agcggttagc tccttcggtc ctccgatcgt tgtcagaagt aagttggccg cagtgttatc   5700

actcatggtt atggcagcac tgcataattc tcttactgtc atgccatccg taagatgctt   5760

ttctgtgact ggtgagtact caaccaagtc attctgagaa tagtgtatgc ggcgaccgag   5820

ttgctcttgc ccggcgtcaa tacgggataa taccgcgcca catagcagaa ctttaaaagt   5880

gctcatcatt ggaaaacgtt cttcggggcg aaaactctca aggatcttac cgctgttgag   5940

atccagttcg atgtaaccca ctcgtgcacc caactgatct tcagcatctt ttactttcac   6000

cagcgtttct gggtgagcaa aaacaggaag gcaaaatgcc gcaaaaaagg gaataagggc   6060

gacacggaaa tgttgaatac tcatactctt cctttttcaa tattattgaa gcatttatca   6120

gggttattgt ctcatgagcg gatacatatt tgaatgtatt tagaaaaata aacaaatagg   6180

ggttccgcg                                                           6189
```

<210> SEQ ID NO 43
<211> LENGTH: 10648
<212> TYPE: DNA
<213> ORGANISM: Artificial Sequence
<220> FEATURE:
<223> OTHER INFORMATION: Synthetic Sequence - Vector SY45(CMV_Cas9-PmCDA1,EF1_iRFP) (Effector plasmid)
<220> FEATURE:
<221> NAME/KEY: enhancer
<222> LOCATION: (23)..(402)
<223> OTHER INFORMATION: CMV enhancer
<220> FEATURE:
<221> NAME/KEY: promoter
<222> LOCATION: (403)..(606)
<223> OTHER INFORMATION: CMV promoter
<220> FEATURE:
<221> NAME/KEY: promoter
<222> LOCATION: (651)..(669)
<223> OTHER INFORMATION: T7 promoter
<220> FEATURE:
<221> NAME/KEY: misc_feature
<222> LOCATION: (689)..(691)
<223> OTHER INFORMATION: Kozak sequence
<220> FEATURE:
<221> NAME/KEY: misc_signal
<222> LOCATION: (692)..(742)
<223> OTHER INFORMATION: NLS unit
<220> FEATURE:
<221> NAME/KEY: misc_signal
<222> LOCATION: (698)..(718)
<223> OTHER INFORMATION: SV40 NLS
<220> FEATURE:
<221> NAME/KEY: gene
<222> LOCATION: (743)..(4879)
<223> OTHER INFORMATION: Cas9
<220> FEATURE:
<221> NAME/KEY: misc_signal
<222> LOCATION: (4859)..(4879)
<223> OTHER INFORMATION: SV40 NLS
<220> FEATURE:
<221> NAME/KEY: misc_structure
<222> LOCATION: (4910)..(5080)
<223> OTHER INFORMATION: dead SH3 hs
<220> FEATURE:
<221> NAME/KEY: misc_signal
<222> LOCATION: (5087)..(5152)
<223> OTHER INFORMATION: 3xFLAG hs
<220> FEATURE:

```
<221> NAME/KEY: gene
<222> LOCATION: (5159)..(5782)
<223> OTHER INFORMATION: HsPmCDA1
<220> FEATURE:
<221> NAME/KEY: polyA_signal
<222> LOCATION: (5799)..(5920)
<223> OTHER INFORMATION: SV40 poly(A) signal
<220> FEATURE:
<221> NAME/KEY: rep_origin
<222> LOCATION: (6026)..(6614)
<223> OTHER INFORMATION: ori
<220> FEATURE:
<221> NAME/KEY: gene
<222> LOCATION: (6788)..(7645)
<223> OTHER INFORMATION: AmpR
<220> FEATURE:
<221> NAME/KEY: promoter
<222> LOCATION: (7646)..(7750)
<223> OTHER INFORMATION: AmpR promoter
<220> FEATURE:
<221> NAME/KEY: promoter
<222> LOCATION: (8145)..(9322)
<223> OTHER INFORMATION: EF-1alpha promoter
<220> FEATURE:
<221> NAME/KEY: Intron
<222> LOCATION: (8376)..(9313)
<223> OTHER INFORMATION: EF-1alpha intron A
<220> FEATURE:
<221> NAME/KEY: gene
<222> LOCATION: (9349)..(10284)
<223> OTHER INFORMATION: iRFP670
<220> FEATURE:
<221> NAME/KEY: misc_feature
<222> LOCATION: (9349)..(9352)
<223> OTHER INFORMATION: Kozak sequence
<220> FEATURE:
<221> NAME/KEY: polyA_signal
<222> LOCATION: (10314)..(10538)
<223> OTHER INFORMATION: bGH poly(A)

<400> SEQUENCE: 43

gggtaacgcc agggtacgcg ttgacattga ttattgacta gttattaata gtaatcaatt     60

acggggtcat tagttcatag cccatatatg gagttccgcg ttacataact tacggtaaat    120

ggcccgcctg gctgaccgcc caacgacccc cgcccattga cgtcaataat gacgtatgtt    180

cccatagtaa cgccaatagg gactttccat tgacgtcaat gggtggagta tttacggtaa    240

actgcccact tggcagtaca tcaagtgtat catatgccaa gtacgccccc tattgacgtc    300

aatgacggta aatggcccgc ctggcattat gcccagtaca tgaccttatg ggactttcct    360

acttggcagt acatctacgt attagtcatc gctattacca tggtgatgcg gttttggcag    420

tacatcaatg ggcgtggata gcggtttgac tcacggggat ttccaagtct ccaccccatt    480

gacgtcaatg ggagtttgtt ttggcaccaa aatcaacggg actttccaaa atgtcgtaac    540

aactccgccc cattgacgca aatgggcggt aggcgtgtac ggtgggaggt ctatataagc    600

agagctctct ggctaactag agaacccact gcttactggc ttatcgaaat taatacgact    660

cactataggg agacccaagc tggctagcga aatggcaccg aagaagaagc gtaaagtcgg    720

aatccacgga gttcctgcgg caatggacaa gaagtactcc attgggctcg atatcggcac    780

aaacagcgtc ggttgggccg tcattacgga cgagtacaag gtgccgagca aaaaattcaa    840

agttctgggc aataccgatc gccacagcat aaagaagaac ctcattggcg ccctcctgtt    900

cgactccggg gagacggccg aagccacgcg gctcaaaaga acagcacggc gcagatatac    960

ccgcagaaag aatcggatct gctacctgca ggagatcttt agtaatgaga tggctaaggt   1020

ggatgactct ttcttccata ggctggagga gtcctttttg gtggaggagg ataaaaagca   1080

cgagcgccac ccaatctttg gcaatatcgt ggacgaggtg gcgtaccatg aaaagtaccc   1140
```

```
aaccatatat catctgagga agaagcttgt agacagtact gataaggctg acttgcggtt   1200
gatctatctc gcgctggcgc atatgatcaa atttcgggga cacttcctca tcgaggggga   1260
cctgaaccca gacaacagcg atgtcgacaa actctttatc caactggttc agacttacaa   1320
tcagcttttc gaagagaacc cgatcaacgc atccggagtt gacgccaaag caatcctgag   1380
cgctaggctg tccaaatccc ggcggctcga aaacctcatc gcacagctcc ctggggagaa   1440
gaagaacggc ctgtttggta atcttatcgc cctgtcactc gggctgaccc ccaactttaa   1500
atctaacttc gacctggccg aagatgccaa gcttcaactg agcaaagaca cctacgatga   1560
tgatctcgac aatctgctgg cccagatcgg cgaccagtac gcagaccttt ttttggcggc   1620
aaagaacctg tcagacgcca ttctgctgag tgatattctg cgagtgaaca cggagatcac   1680
caaagctccg ctgagcgcta gtatgatcaa gcgctatgat gagcaccacc aagacttgac   1740
tttgctgaag gcccttgtca gacagcaact gcctgagaag tacaaggaaa ttttcttcga   1800
tcagtctaaa aatggctacg ccggatacat tgacggcgga gcaagccagg aggaatttta   1860
caaatttatt aagcccatct tggaaaaaat ggacggcacc gaggagctgc tggtaaagct   1920
taacagagaa gatctgttgc gcaaacagcg cactttcgac aatggaagca tcccccacca   1980
gattcacctg ggcgaactgc acgctatcct caggcggcaa gaggatttct accccttttt   2040
gaaagataac agggaaaaga ttgagaaaat cctcacattt cggataccct actatgtagg   2100
cccccctcgcc cggggaaatt ccagattcgc gtggatgact cgcaaatcag aagagaccat   2160
cactccctgg aacttcgagg aagtcgtgga taagggggcc tctgcccagt ccttcatcga   2220
aaggatgact aactttgata aaaatctgcc taacgaaaag gtgcttccta aacactctct   2280
gctgtacgag tacttcacag tttataacga gctcaccaag gtcaaatacg tcacagaagg   2340
gatgagaaag ccagcattcc tgtctggaga gcagaagaaa gctatcgtgg acctcctctt   2400
caagacgaac cggaaagtta ccgtgaaaca gctcaaagaa gactatttca aaaagattga   2460
atgtttcgac tctgttgaaa tcagcggagt ggaggatcgc ttcaacgcat ccctgggaac   2520
gtatcacgat ctcctgaaaa tcattaaaga caaggacttc ctggacaatg aggagaacga   2580
ggacattctt gaggacattg tcctcaccct tacgttgttt gaagataggg agatgattga   2640
agaacgcttg aaaacttacg ctcatctctt cgacgacaaa gtcatgaaac agctcaagag   2700
gcgccgatat acaggatggg ggcggctgtc aagaaaactg atcaatggga tccgagacaa   2760
gcagagtgga aagacaatcc tggattttct taagtccgat ggatttgcca accggaactt   2820
catgcagttg atccatgatg actctctcac ctttaaggag gacatccaga aagcacaagt   2880
ttctggccag ggggacagtc ttcacgagca catcgctaat cttgcaggta gcccagctat   2940
caaaaaggga atactgcaga ccgttaaggt cgtggatgaa ctcgtcaaag taatgggaag   3000
gcataagccc gagaatatcg ttatcgagat ggcccgagag aaccaaacta cccagaaggg   3060
acagaagaac agtagggaaa ggatgaagag gattgaagag ggtataaaag aactggggtc   3120
ccaaatcctt aaggaacacc cagttgaaaa cacccagctt cagaatgaga agctctacct   3180
gtactacctg cagaacggca gggacatgta cgtggatcag gaactggaca tcaatcggct   3240
ctccgactac gacgtggatc atatcgtgcc ccagtctttt ctcaaagatg attctattga   3300
taataaagtg ttgacaagat ccgataaaaa tagagggaag agtgataacg tcccctcaga   3360
agaagttgtc aagaaaatga aaaattattg gcggcagctg ctgaacgcca aactgatcac   3420
acaacggaag ttcgataatc tgactaaggc tgaacgaggt ggcctgtctg agttggataa   3480
```

```
agccggcttc atcaaaaggc agcttgttga gacacgccag atcaccaagc acgtggccca   3540
aattctcgat tcacgcatga acaccaagta cgatgaaaat gacaaactga ttcgagaggt   3600
gaaagttatt actctgaagt ctaagctggt ctcagatttc agaaaggact ttcagtttta   3660
taaggtgaga gagatcaaca attaccacca tgcgcatgat gcctacctga atgcagtggt   3720
aggcactgca cttatcaaaa aatatcccaa gcttgaatct gaatttgttt acggagacta   3780
taaagtgtac gatgttagga aaatgatcgc aaagtctgag caggaaatag gcaaggccac   3840
cgctaagtac ttcttttaca gcaatattat gaatttttc aagaccgaga ttacactggc   3900
caatggagag attcggaagc gaccacttat cgaaacaaac ggagaaacag gagaaatcgt   3960
gtgggacaag ggtagggatt tcgcgacagt ccggaaggtc ctgtccatgc cgcaggtgaa   4020
catcgttaaa aagaccgaag tacagaccgg aggcttctcc aaggaaagta tcctcccgaa   4080
aaggaacagc gacaagctga tcgcacgcaa aaaagattgg gaccccaaga aatacggcgg   4140
attcgattct cctacagtcg cttacagtgt actggttgtg gccaaagtgg agaaagggaa   4200
gtctaaaaaa ctcaaaagcg tcaaggaact gctgggcatc acaatcatgg agcgatcaag   4260
cttcgaaaaa aaccccatcg actttctcga ggcgaaagga tataaagagg tcaaaaaaga   4320
cctcatcatt aagcttccca agtactctct ctttgagctt gaaaacggcc ggaaacgaat   4380
gctcgctagt gcgggcgagc tgcagaaagg taacgagctg gcactgccct ctaaatacgt   4440
taatttcttg tatctggcca gccactatga aaagctcaaa gggtctcccg aagataatga   4500
gcagaagcag ctgttcgtgg aacaacacaa acactacctt gatgagatca tcgagcaaat   4560
aagcgaattc tccaaaagag tgatcctcgc cgacgctaac ctcgataagg tgctttctgc   4620
ttacaataag cacagggata agcccatcag ggagcaggca gaaaacatta tccacttgtt   4680
tactctgacc aacttgggcg cgcctgcagc cttcaagtac ttcgacacca ccatagacag   4740
aaagcggtac acctctacaa aggaggtcct ggacgccaca ctgattcatc agtcaattac   4800
ggggctctat gaaacaagaa tcgacctctc tcagctcggt ggagacagca gggctgaccc   4860
caagaagaag aggaaggtgg gtggaggagg taccggcggt ggaggctcag cagaatacgt   4920
acgagctctg tttgacttca atgggaatga cgaggaggat ctccccttta agaagggcga   4980
tattctccgc atcagagata agcccgaaga acaatggtgg aatgccgagg atagcgaagg   5040
gaaaaggggc atgattctgg tgccatatgt ggagaaatat tccggtgact acaaagacca   5100
tgatggggat tacaaagacc acgacatcga ctacaaagac gacgacgata aatcagggat   5160
gacagacgcc gagtacgtgc gcattcatga gaaactggat atttacacct tcaagaagca   5220
gttcttcaac aacaagaaat ctgtgtcaca ccgctgctac gtgctgtttg agttgaagcg   5280
aaggggcgaa agaagggctt gcttttgggg ctatgccgtc aacaagcccc aaagtggcac   5340
cgagagagga atacacgctg agatattcag tatccgaaag gtggaagagt atcttcggga   5400
taatcctggg cagtttacga tcaactggta ttccagctgg agtccttgcg ctgattgtgc   5460
cgagaaaatt ctggaatggt ataatcagga acttcgggga aacgggcaca cattgaaaat   5520
ctgggcctgc aagctgtact acgagaagaa tgcccggaac cagataggac tctggaatct   5580
gagggacaat ggtgtaggcc tgaacgtgat ggtttccgag cactatcagt gttgtcggaa   5640
gattttcatc caaagctctc ataaccagct caatgaaaac cgctggttgg agaaaacact   5700
gaaacgtgcg gagaagcgga gatccgagct gagcatcatg atccaggtca agattctgca   5760
taccactaag tctccagccg tttagcttcg cccaccccaa cttgtttatt gcagcttata   5820
atggttacaa ataaagcaat agcatcacaa atttcacaaa taaagcattt ttttcactgc   5880
```

```
attctagttg tggtttgtcc aaactcatca atgtatctta gcggccgcca ccgcggtgga   5940
gctccagctt ttgttccctt tagtgagggt taattgcgcg ccagcaaaag gccaggaacc   6000
gtaaaaaggc cgcgttgctg gcgtttttcc ataggctccg cccccctgac gagcatcaca   6060
aaaatcgacg ctcaagtcag aggtggcgaa acccgacagg actataaaga taccaggcgt   6120
ttccccctgg aagctccctc gtgcgctctc ctgttccgac cctgccgctt accggatacc   6180
tgtccgcctt tctcccttcg ggaagcgtgg cgctttctca tagctcacgc tgtaggtatc   6240
tcagttcggt gtaggtcgtt cgctccaagc tgggctgtgt gcacgaaccc cccgttcagc   6300
ccgaccgctg cgccttatcc ggtaactatc gtcttgagtc caacccggta agacacgact   6360
tatcgccact ggcagcagcc actggtaaca ggattagcag agcgaggtat gtaggcggtg   6420
ctacagagtt cttgaagtgg tggcctaact acggctacac tagaagaaca gtatttggta   6480
tctgcgctct gctgaagcca gttaccttcg gaaaaagagt tggtagctct tgatccggca   6540
aacaaaccac cgctggtagc ggtggttttt ttgtttgcaa gcagcagatt acgcgcagaa   6600
aaaaaggatc tcaagaagat cctttgatct tttctacggg gtctgacgct cagtggaacg   6660
aaaactcacg ttaagggatt ttggtcatga gattatcaaa aaggatcttc acctagatcc   6720
ttttaaatta aaaatgaagt tttaaatcaa tctaaagtat atatgagtaa acttggtctg   6780
acagttacca atgcttaatc agtgaggcac ctatctcagc gatctgtcta tttcgttcat   6840
ccatagttgc ctgactcccc gtcgtgtaga taactacgat acgggagggc ttaccatctg   6900
gccccagtgc tgcaatgata ccgcgagacc cacgctcacc ggctccagat ttatcagcaa   6960
taaaccagcc agccggaagg gccgagcgca gaagtggtcc tgcaacttta tccgcctcca   7020
tccagtctat taattgttgc cgggaagcta gagtaagtag ttcgccagtt aatagtttgc   7080
gcaacgttgt tgccattgct acaggcatcg tggtgtcacg ctcgtcgttt ggtatggctt   7140
cattcagctc cggttcccaa cgatcaaggc gagttacatg atcccccatg ttgtgcaaaa   7200
aagcggttag ctccttcggt cctccgatcg ttgtcagaag taagttggcc gcagtgttat   7260
cactcatggt tatggcagca ctgcataatt ctcttactgt catgccatcc gtaagatgct   7320
tttctgtgac tggtgagtac tcaaccaagt cattctgaga atagtgtatg cggcgaccga   7380
gttgctcttg cccggcgtca atacgggata ataccgcgcc acatagcaga actttaaaag   7440
tgctcatcat tggaaaacgt tcttcggggc gaaaactctc aaggatctta ccgctgttga   7500
gatccagttc gatgtaaccc actcgtgcac ccaactgatc ttcagcatct tttactttca   7560
ccagcgtttc tgggtgagca aaaacaggaa ggcaaaatgc cgcaaaaaag ggaataaggg   7620
cgacacggaa atgttgaata ctcatactct tcctttttca atattattga agcatttatc   7680
agggttattg tctcatgagc ggatacatat ttgaatgtat ttagaaaaat aaacaaatag   7740
gggttccgcg cacatttccc cgaaaagtgc cacctaaatt gtaagcgtta atattttgtt   7800
aaaattcgcg ttaaattttt gttaaatcag ctcatttttt aaccaatagg ccgaaatcgg   7860
caaaatccct tataaatcaa aagaatagac cgagataggg ttgagtgttg ttccagtttg   7920
gaacaagagt ccactattaa agaacgtgga ctccaacgtc aaagggcgaa aaaccgtcta   7980
tcagggcgat ggcccactac gtgaaccatc accctaatca agttttttgg ggtcgaggtg   8040
ccgtaaagca ctaaatcgga accctaaagg gagcccccga tttagagctt gacggggaaa   8100
gccgcagcta atggaccttc taggtcttga aaggagtggg aattggctcc ggtgcccgtc   8160
agtgggcaga gcgcacatcg cccacagtcc ccgagaagtt ggggggaggg gtcggcaatt   8220
```

```
gaaccggtgc ctagagaagg tggcgcgggg taaactggga aagtgatgtc gtgtactggc   8280
tccgcctttt tcccgagggt gggggagaac cgtatataag tgcagtagtc gccgtgaacg   8340
ttcttttttcg caacgggttt gccgccagaa cacaggtaag tgccgtgtgt ggttcccgcg   8400
ggcctggcct ctttacgggt tatggccctt gcgtgccttg aattacttcc actggctgca   8460
gtacgtgatt cttgatcccg agcttcgggt tggaagtggg tgggagagtt cgaggccttg   8520
cgcttaagga gccccttcgc ctcgtgcttg agttgaggcc tggcctgggc gctggggccg   8580
ccgcgtgcga atctggtggc accttcgcgc ctgtctcgct gctttcgata agtctctagc   8640
catttaaaat ttttgatgac ctgctgcgac gcttttttttc tggcaagata gtcttgtaaa   8700
tgcgggccaa gatctgcaca ctggtatttc ggtttttggg gccgcgggcg gcgacggggc   8760
ccgtgcgtcc cagcgcacat gttcggcgag gcggggcctg cgagcgcggc caccgagaat   8820
cggacggggg tagtctcaag ctggccggcc tgctctggtg cctggcctcg cgccgccgtg   8880
tatcgccccg ccctgggcgg caaggctggc ccggtcggca ccagttgcgt gagcggaaag   8940
atggccgctt cccggccctg ctgcagggag ctcaaaatgg aggacgcggc gctcgggaga   9000
gcgggcgggt gagtcaccca cacaaaggaa aagggccttt ccgtcctcag ccgtcgcttc   9060
atgtgactcc acggagtacc gggcgccgtc caggcacctc gattagttct cgagcttttg   9120
gagtacgtcg tctttaggtt ggggggaggg gttttatgcg atggagtttc cccacactga   9180
gtgggtggag actgaagtta ggccagcttg gcacttgatg taattctcct tggaatttgc   9240
cctttttgag tttggatctt ggttcattct caagcctcag acagtggttc aaagtttttt   9300
tcttccattt caggtgtcgt gaggaatttc gacccggatc cggccaccat ggcgcgtaag   9360
gtcgatctca cctcctgcga tcgcgagccg atccacatcc ccggcagcat tcagccgtgc   9420
ggctgcctgc tagcctgcga cgcgcaggcg gtgcggatca cgcgcattac ggaaaatgcc   9480
ggcgcgttct ttggacgcga aactccgcgg gtcggtgagc tactcgccga ttacttcggc   9540
gagaccgaag cccatgcgct gcgcaacgca ctggcgcagt cctccgatcc aaagcgaccg   9600
gcgctgatct tcggttggcg cgacggcctg accggccgca ccttcgacat ctcactgcat   9660
cgccatgacg gtacatcgat catcgagttc gagcctgcgg cggccgaaca ggccgacaat   9720
ccgctgcggc tgacgcggca gatcatcgcg cgcaccaaag aactgaagtc gctcgaagag   9780
atggccgcac gggtgccgcg ctatctgcag gcgatgctcg gctatcaccg cgtgatgttg   9840
taccgcttcg cggacgacgg ctccgggatg gtgatcggcg aggcgaagcg cagcgacctc   9900
gagagctttc tcggtcagca ctttccggcg tcgctggtcc cgcagcaggc gcggctactg   9960
tacttgaaga acgcgatccg cgtggtctcg gattcgcgcg gcatcagcag ccggatcgtg  10020
cccgagcacg acgcctccgg cgccgcgctc gatctgtcgt tcgcgcacct gcgcagcatc  10080
tcgccctgcc atctcgaatt tctgcggaac atgggcgtca gcgcctcgat gtcgctgtcg  10140
atcatcattg acggcacgct atggggattg atcatctgtc atcattacga gccgcgtgcc  10200
gtgccgatgg cgcagcgcgt cgcggccgaa atgttcgccg acttcttatc gctgcacttc  10260
accgccgccc accaccaacg ctaagcggcc gcgactctaa ccggtctcag aagccataga  10320
gcccaccgca tccccagcat gcctgctatt gtcttcccaa tcctcccccct tgctgtcctg  10380
ccccacccca ccccccagaa tagaatgaca cctactcaga caatgcgatg caatttcctc  10440
attttattag gaaaggacag tgggagtggc accttccagg gtcaaggaag gcacggggga  10500
ggggcaaaca acagatggct ggcaactaga aggcacagtc gaggctgatc attcaggctg  10560
cgcaactgtt gggaagggcg atcggtgcgg gcctcttcgc tattacgcca gctggcgaaa  10620
```

gggggatgtg ctgcaaggcg attaagtt 10648

<210> SEQ ID NO 44
<211> LENGTH: 10120
<212> TYPE: DNA
<213> ORGANISM: Artificial Sequence
<220> FEATURE:
<223> OTHER INFORMATION: Synthetic Sequence - Vector SY45(CMV_Cas9,EF1_iRFP) (Effector plasmid)
<220> FEATURE:
<221> NAME/KEY: promoter
<222> LOCATION: (76)..(1253)
<223> OTHER INFORMATION: EF-1alpha promoter
<220> FEATURE:
<221> NAME/KEY: Intron
<222> LOCATION: (307)..(1244)
<223> OTHER INFORMATION: EF-1alpha intron A
<220> FEATURE:
<221> NAME/KEY: gene
<222> LOCATION: (1280)..(2215)
<223> OTHER INFORMATION: iRFP670
<220> FEATURE:
<221> NAME/KEY: misc_feature
<222> LOCATION: (1280)..(1283)
<223> OTHER INFORMATION: Kozak sequence
<220> FEATURE:
<221> NAME/KEY: polyA_signal
<222> LOCATION: (2245)..(2469)
<223> OTHER INFORMATION: bGH poly(A)
<220> FEATURE:
<221> NAME/KEY: promoter
<222> LOCATION: (2677)..(2905)
<223> OTHER INFORMATION: H1 promoter
<220> FEATURE:
<221> NAME/KEY: misc_feature
<222> LOCATION: (2925)..(2925)
<223> OTHER INFORMATION: target1
<220> FEATURE:
<221> NAME/KEY: misc_structure
<222> LOCATION: (2926)..(3001)
<223> OTHER INFORMATION: gRNA scaffold
<220> FEATURE:
<221> NAME/KEY: enhancer
<222> LOCATION: (3016)..(3395)
<223> OTHER INFORMATION: CMV enhancer
<220> FEATURE:
<221> NAME/KEY: promoter
<222> LOCATION: (3396)..(3599)
<223> OTHER INFORMATION: CMV promoter
<220> FEATURE:
<221> NAME/KEY: misc_signal
<222> LOCATION: (3646)..(3696)
<223> OTHER INFORMATION: NLS unit
<220> FEATURE:
<221> NAME/KEY: misc_signal
<222> LOCATION: (3652)..(3672)
<223> OTHER INFORMATION: SV40 NLS
<220> FEATURE:
<221> NAME/KEY: gene
<222> LOCATION: (3697)..(7836)
<223> OTHER INFORMATION: Cas9
<220> FEATURE:
<221> NAME/KEY: misc_signal
<222> LOCATION: (7813)..(7833)
<223> OTHER INFORMATION: SV40 NLS
<220> FEATURE:
<221> NAME/KEY: polyA_signal
<222> LOCATION: (7850)..(7971)
<223> OTHER INFORMATION: SV40 poly(A) signal
<220> FEATURE:
<221> NAME/KEY: rep_origin
<222> LOCATION: (8077)..(8665)
<223> OTHER INFORMATION: ori
<220> FEATURE:
<221> NAME/KEY: gene
<222> LOCATION: (8839)..(9696)
<223> OTHER INFORMATION: AmpR
<220> FEATURE:
<221> NAME/KEY: promoter
<222> LOCATION: (9697)..(9801)
<223> OTHER INFORMATION: AmpR promoter

<400> SEQUENCE: 44

```
ggagcccccg atttagagct tgacggggaa agccgcagct aatggacctt ctaggtcttg     60
aaaggagtgg gaattggctc cggtgcccgt cagtgggcag agcgcacatc gcccacagtc    120
cccgagaagt tggggggagg ggtcggcaat tgaaccggtg cctagagaag gtggcgcggg    180
gtaaactggg aaagtgatgt cgtgtactgg ctccgccttt ttcccgaggg tgggggagaa    240
ccgtatataa gtgcagtagt cgccgtgaac gttctttttc gcaacgggtt tgccgccaga    300
acacaggtaa gtgccgtgtg tggttcccgc gggcctggcc tctttacggg ttatggccct    360
tgcgtgcctt gaattacttc cactggctgc agtacgtgat tcttgatccc gagcttcggg    420
ttggaagtgg gtgggagagt tcgaggcctt gcgcttaagg agccccttcg cctcgtgctt    480
gagttgaggc ctggcctggg cgctggggcc gccgcgtgcg aatctggtgg caccttcgcg    540
cctgtctcgc tgctttcgat aagtctctag ccatttaaaa tttttgatga cctgctgcga    600
cgcttttttt ctggcaagat agtcttgtaa atgcgggcca agatctgcac actggtattt    660
cggtttttgg ggccgcgggc ggcgacgggg cccgtgcgtc ccagcgcaca tgttcggcga    720
ggcggggcct gcgagcgcgg ccaccgagaa tcggacgggg gtagtctcaa gctggccggc    780
ctgctctggt gcctggcctc gcgccgccgt gtatcgcccc gccctgggcg gcaaggctgg    840
cccggtcggc accagttgcg tgagcggaaa gatggccgct tcccggccct gctgcaggga    900
gctcaaaatg gaggacgcgg cgctcgggag agcgggcggg tgagtcaccc acacaaagga    960
aaagggcctt tccgtcctca gccgtcgctt catgtgactc cacggagtac cgggcgccgt   1020
ccaggcacct cgattagttc tcgagctttt ggagtacgtc gtctttaggt tgggggggagg  1080
ggttttatgc gatggagttt ccccacactg agtgggtgga gactgaagtt aggccagctt   1140
ggcacttgat gtaattctcc ttggaatttg ccctttttga gtttggatct tggttcattc   1200
tcaagcctca gacagtggtt caaagttttt ttcttccatt tcaggtgtcg tgaggaattt   1260
cgacccggat ccggccacca tggcgcgtaa ggtcgatctc acctcctgcg atcgcgagcc   1320
gatccacatc cccggcagca ttcagccgtg cggctgcctg ctagcctgcg acgcgcaggc   1380
ggtgcggatc acgcgcatta cggaaaatgc cggcgcgttc tttggacgcg aaactccgcg   1440
ggtcggtgag ctactcgccg attacttcgg cgagaccgaa gcccatgcgc tgcgcaacgc   1500
actggcgcag tcctccgatc caaagcgacc ggcgctgatc ttcggttggc gcgacggcct   1560
gaccggccgc accttcgaca tctcactgca tcgccatgac ggtacatcga tcatcgagtt   1620
cgagcctgcg gcggccgaac aggccgacaa tccgctgcgg ctgacgcggc agatcatcgc   1680
gcgcaccaaa gaactgaagt cgctcgaaga gatggccgca cgggtgccgc gctatctgca   1740
ggcgatgctc ggctatcacc gcgtgatgtt gtaccgcttc gcggacgacg gctccgggat   1800
ggtgatcggc gaggcgaagc gcagcgacct cgagagcttt ctcggtcagc actttccggc   1860
gtcgctggtc ccgcagcagg cgcggctact gtacttgaag aacgcgatcc gcgtggtctc   1920
ggattcgcgc ggcatcagca gccggatcgt gcccgagcac gacgcctccg gcgccgcgct   1980
cgatctgtcg ttcgcgcacc tgcgcagcat ctcgccctgc catctcgaat ttctgcggaa   2040
catgggcgtc agcgcctcga tgtcgctgtc gatcatcatt gacggcacgc tatggggatt   2100
gatcatctgt catcattacg agccgcgtgc cgtgccgatg gcgcagcgcg tcgcggccga   2160
```

-continued

| | |
|---|---|
| aatgttcgcc gacttcttat cgctgcactt caccgccgcc caccaccaac gctaagcggc | 2220 |
| cgcgactcta accggtctca gaagccatag agcccaccgc atccccagca tgcctgctat | 2280 |
| tgtcttccca atcctccccc ttgctgtcct gccccacccc accccccaga atagaatgac | 2340 |
| acctactcag acaatgcgat gcaatttcct cattttatta ggaaaggaca gtgggagtgg | 2400 |
| caccttccag ggtcaaggaa ggcacggggg aggggcaaac aacagatggc tggcaactag | 2460 |
| aaggcacagt cgaggctgat cattcaggct gcgcaactgt tgggaagggc gatcggtgcg | 2520 |
| ggcctcttcg ctattacgcc agctggcgaa agggggatgt gctgcaaggc gattaagttg | 2580 |
| ggtaacgcca gggttttccc agtcacgacg ttgtaaaacg acggccagtg agcgcgcgta | 2640 |
| atacgactca ctatagggcg aattgggtac cgggccaatt cgaacgctga cgtcatcaac | 2700 |
| ccgctccaag gaatcgcggg cccagtgtca ctaggcggga acacccagcg cgcgtgcgcc | 2760 |
| ctggcaggaa gatggctgtg agggacaggg gagtggcgcc ctgcaatatt tgcatgtcgc | 2820 |
| tatgtgttct gggaaatcac cataaacgtg aaatgtcttt ggatttggga atcttataag | 2880 |
| ttctgtatga ggaccacaga tccccagaag agccggcgct cttcagtttt agagctagaa | 2940 |
| atagcaagtt aaaataaggc tagtccgtta tcaacttgaa aaagtggcac cgagtcggtg | 3000 |
| cttttttttac gcgttgacat tgattattga ctagttatta atagtaatca attacggggt | 3060 |
| cattagttca tagcccatat atggagttcc gcgttacata acttacggta aatggcccgc | 3120 |
| ctggctgacc gcccaacgac ccccgcccat tgacgtcaat aatgacgtat gttcccatag | 3180 |
| taacgccaat agggactttc cattgacgtc aatgggtgga gtatttacgg taaactgccc | 3240 |
| acttggcagt acatcaagtg tatcatatgc caagtacgcc ccctattgac gtcaatgacg | 3300 |
| gtaaatggcc cgcctggcat tatgcccagt acatgacctt atgggacttt cctacttggc | 3360 |
| agtacatcta cgtattagtc atcgctatta ccatggtgat gcggttttgg cagtacatca | 3420 |
| atgggcgtgg atagcggttt gactcacggg gatttccaag tctccacccc attgacgtca | 3480 |
| atgggagttt gttttggcac caaaatcaac gggactttcc aaaatgtcgt aacaactccg | 3540 |
| ccccattgac gcaaatgggc ggtaggcgtg tacggtggga ggtctatata agcagagctc | 3600 |
| tctggctaac tagagaaccc actgcttact ggcttatcgg ccaccatggc accgaagaag | 3660 |
| aagcgtaaag tcggaatcca cggagttcct gcggcaatgg acaagaagta ctccattggg | 3720 |
| ctcgatatcg gcacaaacag cgtcggttgg gccgtcatta cggacgagta caaggtgccg | 3780 |
| agcaaaaaat tcaaagttct gggcaatacc gatcgccaca gcataaagaa gaacctcatt | 3840 |
| ggcgccctcc tgttcgactc cggggagacg gccgaagcca cgcggctcaa aagaacagca | 3900 |
| cggcgcagat atacccgcag aaagaatcgg atctgctacc tgcaggagat ctttagtaat | 3960 |
| gagatggcta aggtggatga ctctttcttc cataggctgg aggagtcctt tttggtggag | 4020 |
| gaggataaaa agcacgagcg ccacccaatc tttggcaata tcgtggacga ggtggcgtac | 4080 |
| catgaaaagt acccaaccat atatcatctg aggaagaagc ttgtagacag tactgataag | 4140 |
| gctgacttgc ggttgatcta tctcgcgctg gcgcatatga tcaaatttcg gggacacttc | 4200 |
| ctcatcgagg gggacctgaa cccagacaac agcgatgtcg acaaactctt tatccaactg | 4260 |
| gttcagactt acaatcagct tttcgaagag aacccgatca acgcatccgg agttgacgcc | 4320 |
| aaagcaatcc tgagcgctag gctgtccaaa tcccggcggc tcgaaaacct catcgcacag | 4380 |
| ctccctgggg agaagaagaa cggcctgttt ggtaatctta tcgccctgtc actcgggctg | 4440 |
| acccccaact ttaaatctaa cttcgacctg gccgaagatg ccaagcttca actgagcaaa | 4500 |
| gacacctacg atgatgatct cgacaatctg ctggcccaga tcggcgacca gtacgcagac | 4560 |

```
cttttttgg cggcaaagaa cctgtcagac gccattctgc tgagtgatat tctgcgagtg   4620
aacacggaga tcaccaaagc tccgctgagc gctagtatga tcaagcgcta tgatgagcac   4680
caccaagact tgactttgct gaaggccctt gtcagacagc aactgcctga gaagtacaag   4740
gaaattttct tcgatcagtc taaaaatggc tacgccggat acattgacgg cggagcaagc   4800
caggaggaat tttacaaatt tattaagccc atcttggaaa aaatggacgg caccgaggag   4860
ctgctggtaa agcttaacag agaagatctg ttgcgcaaac agcgcacttt cgacaatgga   4920
agcatccccc accagattca cctgggcgaa ctgcacgcta tcctcaggcg gcaagaggat   4980
ttctacccct ttttgaaaga taacagggaa aagattgaga aaatcctcac atttcggata   5040
ccctactatg taggcccccct cgcccgggga aattccagat tcgcgtggat gactcgcaaa   5100
tcagaagaga ccatcactcc ctggaacttc gaggaagtcg tggataaggg ggcctctgcc   5160
cagtccttca tcgaaaggat gactaacttt gataaaaatc tgcctaacga aaaggtgctt   5220
cctaaacact ctctgctgta cgagtacttc acagtttata acgagctcac caaggtcaaa   5280
tacgtcacag aagggatgag aaagccagca ttcctgtctg gagagcagaa gaaagctatc   5340
gtggacctcc tcttcaagac gaaccggaaa gttaccgtga aacagctcaa agaagactat   5400
ttcaaaaaga ttgaatgttt cgactctgtt gaaatcagcg gagtggagga tcgcttcaac   5460
gcatccctgg gaacgtatca cgatctcctg aaaatcatta aagacaagga cttcctggac   5520
aatgaggaga acgaggacat tcttgaggac attgtcctca cccttacgtt gtttgaagat   5580
agggagatga ttgaagaacg cttgaaaact tacgctcatc tcttcgacga caaagtcatg   5640
aaacagctca agaggcgccg atatacagga tgggggcggc tgtcaagaaa actgatcaat   5700
gggatccgag acaagcagag tggaaagaca atcctggatt ttcttaagtc cgatggattt   5760
gccaaccgga acttcatgca gttgatccat gatgactctc tcacctttaa ggaggacatc   5820
cagaaagcac aagtttctgg ccagggggac agtcttcacg agcacatcgc taatcttgca   5880
ggtagcccag ctatcaaaaa gggaatactg cagaccgtta aggtcgtgga tgaactcgtc   5940
aaagtaatgg gaaggcataa gcccgagaat atcgttatcg agatggcccg agagaaccaa   6000
actacccaga agggacagaa gaacagtagg gaaaggatga agaggattga agagggtata   6060
aaagaactgg ggtcccaaat ccttaaggaa cacccagttg aaaacaccca gcttcagaat   6120
gagaagctct acctgtacta cctgcagaac ggcagggaca tgtacgtgga tcaggaactg   6180
gacatcaatc ggctctccga ctacgacgtg gatcatatcg tgccccagtc ttttctcaaa   6240
gatgattcta ttgataataa agtgttgaca agatccgata aaaatagagg gaagagtgat   6300
aacgtcccct cagaagaagt tgtcaagaaa atgaaaaatt attggcggca gctgctgaac   6360
gccaaactga tcacacaacg gaagttcgat aatctgacta aggctgaacg aggtggcctg   6420
tctgagttgg ataaagccgg cttcatcaaa aggcagcttg ttgagacacg ccagatcacc   6480
aagcacgtgg cccaaattct cgattcacgc atgaacacca agtacgatga aaatgacaaa   6540
ctgattcgag aggtgaaagt tattactctg aagtctaagc tggtctcaga tttcagaaag   6600
gactttcagt tttataaggt gagagagatc aacaattacc accatgcgca tgatgcctac   6660
ctgaatgcag tggtaggcac tgcacttatc aaaaaatatc ccaagcttga atctgaattt   6720
gtttacggag actataaagt gtacgatgtt aggaaaatga tcgcaaagtc tgagcaggaa   6780
ataggcaagg ccaccgctaa gtacttcttt tacagcaata ttatgaattt tttcaagacc   6840
gagattacac tggccaatgg agagattcgg aagcgaccac ttatcgaaac aaacggagaa   6900
```

```
acaggagaaa tcgtgtggga caagggtagg gatttcgcga cagtccggaa ggtcctgtcc   6960
atgccgcagg tgaacatcgt taaaaagacc gaagtacaga ccggaggctt ctccaaggaa   7020
agtatcctcc cgaaaaggaa cagcgacaag ctgatcgcac gcaaaaaaga ttgggacccc   7080
aagaaatacg gcggattcga ttctcctaca gtcgcttaca gtgtactggt tgtggccaaa   7140
gtggagaaag ggaagtctaa aaaactcaaa agcgtcaagg aactgctggg catcacaatc   7200
atggagcgat caagcttcga aaaaaacccc atcgactttc tcgaggcgaa aggatataaa   7260
gaggtcaaaa aagacctcat cattaagctt cccaagtact ctctctttga gcttgaaaac   7320
ggccggaaac gaatgctcgc tagtgcgggc gagctgcaga aaggtaacga gctggcactg   7380
ccctctaaat acgttaattt cttgtatctg gccagccact atgaaaagct caaagggtct   7440
cccgaagata atgagcagaa gcagctgttc gtggaacaac acaaacacta ccttgatgag   7500
atcatcgagc aaataagcga attctccaaa agagtgatcc tcgccgacgc taacctcgat   7560
aaggtgcttt ctgcttacaa taagcacagg gataagccca tcagggagca ggcagaaaac   7620
attatccact tgtttactct gaccaacttg ggcgcgcctg cagccttcaa gtacttcgac   7680
accaccatag acagaaagcg gtacacctct acaaaggagg tcctggacgc cacactgatt   7740
catcagtcaa ttacggggct ctatgaaaca agaatcgacc tctctcagct cggtggagac   7800
agcagggctg accccaagaa gaagaggaag gtgtagcttc gcccaccccca acttgtttat   7860
tgcagcttat aatggttaca aataaagcaa tagcatcaca aatttcacaa ataaagcatt   7920
tttttcactg cattctagtt gtggtttgtc caaactcatc aatgtatctt agcggccgcc   7980
accgcggtgg agctccagct tttgttccct ttagtgaggg ttaattgcgc gccagcaaaa   8040
ggccaggaac cgtaaaaagg ccgcgttgct ggcgtttttc cataggctcc gccccccctga   8100
cgagcatcac aaaaatcgac gctcaagtca gaggtggcga aacccgacag gactataaag   8160
ataccaggcg tttccccctg gaagctccct cgtgcgctct cctgttccga ccctgccgct   8220
taccggatac ctgtccgcct ttctcccttc gggaagcgtg gcgctttctc atagctcacg   8280
ctgtaggtat ctcagttcgg tgtaggtcgt tcgctccaag ctgggctgtg tgcacgaacc   8340
ccccgttcag cccgaccgct gcgccttatc cggtaactat cgtcttgagt ccaacccggt   8400
aagacacgac ttatcgccac tggcagcagc cactggtaac aggattagca gagcgaggta   8460
tgtaggcggt gctacagagt tcttgaagtg gtggcctaac tacggctaca ctagaagaac   8520
agtatttggt atctgcgctc tgctgaagcc agttaccttc ggaaaaagag ttggtagctc   8580
ttgatccggc aaacaaacca ccgctggtag cggtggtttt tttgtttgca agcagcagat   8640
tacgcgcaga aaaaaaggat ctcaagaaga tcctttgatc ttttctacgg ggtctgacgc   8700
tcagtggaac gaaaactcac gttaagggat tttggtcatg agattatcaa aaaggatctt   8760
cacctagatc cttttaaatt aaaaatgaag ttttaaatca atctaaagta tatatgagta   8820
aacttggtct gacagttacc aatgcttaat cagtgaggca cctatctcag cgatctgtct   8880
atttcgttca tccatagttg cctgactccc cgtcgtgtag ataactacga tacgggaggg   8940
cttaccatct ggccccagtg ctgcaatgat accgcgagac ccacgctcac cggctccaga   9000
tttatcagca ataaaccagc cagccggaag ggccgagcgc agaagtggtc ctgcaacttt   9060
atccgcctcc atccagtcta ttaattgttg ccgggaagct agagtaagta gttcgccagt   9120
taatagtttg cgcaacgttg ttgccattgc tacaggcatc gtggtgtcac gctcgtcgtt   9180
tggtatggct tcattcagct ccggttccca acgatcaagg cgagttacat gatcccccat   9240
gttgtgcaaa aaagcggtta gctccttcgg tcctccgatc gttgtcagaa gtaagttggc   9300
```

```
cgcagtgtta tcactcatgg ttatggcagc actgcataat tctcttactg tcatgccatc   9360

cgtaagatgc ttttctgtga ctggtgagta ctcaaccaag tcattctgag aatagtgtat   9420

gcggcgaccg agttgctctt gcccggcgtc aatacgggat aataccgcgc cacatagcag   9480

aactttaaaa gtgctcatca ttggaaaacg ttcttcgggg cgaaaactct caaggatctt   9540

accgctgttg agatccagtt cgatgtaacc cactcgtgca cccaactgat cttcagcatc   9600

ttttactttc accagcgttt ctgggtgagc aaaaacagga aggcaaaatg ccgcaaaaaa   9660

gggaataagg gcgacacgga aatgttgaat actcatactc ttcctttttc aatattattg   9720

aagcatttat cagggttatt gtctcatgag cggatacata tttgaatgta tttagaaaaa   9780

taaacaaata ggggttccgc gcacatttcc ccgaaaagtg ccacctaaat tgtaagcgtt   9840

aatattttgt taaaattcgc gttaaatttt tgttaaatca gctcattttt taaccaatag   9900

gccgaaatcg gcaaaatccc ttataaatca aaagaataga ccgagatagg gttgagtgtt   9960

gttccagttt ggaacaagag tccactatta aagaacgtgg actccaacgt caaagggcga  10020

aaaaccgtct atcagggcga tggcccacta cgtgaaccat caccctaatc aagttttttg  10080

gggtcgaggt gccgtaaagc actaaatcgg aaccctaaag                        10120
```

<210> SEQ ID NO 45
<211> LENGTH: 28
<212> TYPE: DNA
<213> ORGANISM: Artificial Sequence
<220> FEATURE:
<223> OTHER INFORMATION: Synthetic Sequence - eGFP switch target

<400> SEQUENCE: 45

```
taccggccca gttggaatgt aggtggtg                                        28
```

<210> SEQ ID NO 46
<211> LENGTH: 28
<212> TYPE: DNA
<213> ORGANISM: Artificial Sequence
<220> FEATURE:
<223> OTHER INFORMATION: Synthetic Sequence - eGFP switch target

<400> SEQUENCE: 46

```
taccggccca gttggaatgt agatggtg                                        28
```

<210> SEQ ID NO 47
<211> LENGTH: 20
<212> TYPE: DNA
<213> ORGANISM: Artificial Sequence
<220> FEATURE:
<223> OTHER INFORMATION: PCR Primer

<400> SEQUENCE: 47

```
ttctgcttgt cggccatgat                                                 20
```

<210> SEQ ID NO 48
<211> LENGTH: 22
<212> TYPE: DNA
<213> ORGANISM: Artificial Sequence
<220> FEATURE:
<223> OTHER INFORMATION: PCR Primer

<400> SEQUENCE: 48

```
aggcaaggct tgaccgacaa tt                                              22
```

METHOD FOR MODIFYING TARGET SITE IN DOUBLE-STRANDED DNA IN CELL

CROSS-REFERENCE TO RELATED APPLICATIONS

This patent application is the U.S. national phase of International Patent Application No. PCT/JP2019/012807, filed Mar. 26, 2019, which claims the benefit of Japanese Patent Application No. 2018-059073, filed on Mar. 26, 2018, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 118,987 bytes ASCII (Text) file named "748768Sequence-Listing.txt," created Feb. 28, 2020.

TECHNICAL FIELD

The present invention relates to a method for modifying a double-stranded DNA, which enables modification of a targeted site in a particular region of a double-stranded DNA, which a cell has, using homologous recombination, without cleaving double-stranded DNA (with no cleavage or single strand cleavage).

BACKGROUND ART

CRISPR (clustered regularly interspaced short palindromic repeats) and CRISPR-associated (Cas) protein are known to work as a bacterial adaptive immune system by cleaving target DNA in a manner dependent on a single guide RNA (sgRNA) and protospacer adjacent motif (PAM). Cas9 nuclease from *Streptococcus pyogenes* is widely used as a powerful genome editing tool in eukaryotes having a double-stranded DNA break (DSB) repair pathway (e.g., non-patent documents 1, 2). During the repair of DSB by the non-homologous end joining (NHEJ) pathway, a small insertion and/or deletion (indels) are/is introduced into the target DNA, and site-specific mutation or gene destruction occurs. Even though the efficiency depends on the host cell, homologous recombination repair (HDR) can be promoted by providing a donor DNA containing a homology arm to the target region for more accurate editing. However, since the above-mentioned conventional methods involve unexpected genome modifications during cleavage of double-stranded DNA, side effects such as strong cytotoxicity, chromosomal rearrangement and the like occur, and they have common problems of impaired reliability in gene therapy, extremely small number of surviving cells by nucleotide modification, and the like. While homologous recombination using Cas9 nickase (nCas9) has also been reported (non-patent documents 1, 2), the recombination induction efficiency is often very low as compared to that of Cas9 nuclease (non-patent document 3). To the knowledge of the present inventor, homologous recombination using Cas9 in which both nuclease activities are inactivated (dCas9) has not been reported.

Recently, deaminase-mediated target base editing has been demonstrated in which nucleotides are directly edited at the m target gene locus without using donor DNA containing a homology arm for the target region (e.g., patent document 1, non-patent documents 4-6). Since this technique utilizes DNA deamination instead of nuclease-mediated DNA cleavage, cell toxicity is low and pinpoint mutation can be introduced.

CITATION LIST

Patent Literature

Patent Literature 1: WO 2015/133554

Non-Patent Literature

Non-Patent Literature 1: Mali, P. et al., Science 339:823-827 (2013)

Non-Patent Literature 2: Cong, L. et al., Science 339:819-823 (2013)

Non-Patent Literature 3: Ran, F. A. et al., Nat Protoc, 8:2281-2308 (2013)

Non-Patent Literature 4: Komor, A. C. et al., Nature 61:5985-91 (2016)

Non-Patent Literature 5: Nishida, K. et al., Science 102: 553-563 (2016)

Non-Patent Literature 6: Ma, Y. et al., Nat. Methods 1-9 (2016) doi:10.1038/nmeth.4027

SUMMARY OF INVENTION

Technical Problem

However, since this technique uses deaminase, there are restrictions on the type of mutation that can be introduced or the site of mutation, and it was not possible to switch the direction and combination of genes or knock-in gene segments. Therefore, the problem of the present invention is the provision of a novel DNA modification technique using a nucleic acid base converting enzyme such as deaminase and the like, or DNA glycosylase, wherein the technique is not limited by the type of mutation that can be introduced or the site of mutation, can switch the direction and combination of genes, and can knock-in gene segments.

Solution to Problem

For dividing cells, a particularly serious mode of DNA damage is a disorder in which both strands of the DNA double strand are cleaved. As a mechanism for repairing this disorder, homologous recombination and non-homologous end-joining are known. On the other hand, in the case of damage to one strand of the DNA double strand, it is mainly repaired by base excision repair, which is a mechanism for repairing damage due to alkylation or deamination, or nucleotide excision repair (NER), which is a mechanism for repairing a relatively large-scale damage on some tens of base pairs that distorts the double strand. While the ratio and the like have not been verified, it is also known that repair of the complementary strand is induced even when one of the DNA double strands is damaged.

However, the degree of activity of complementary strand repair to the base excision repair has not been sufficiently verified, and DNA editing by homologous recombination using base excision repair has not been actively performed. To the knowledge of the present inventor, there is no report of such DNA editing. Under such circumstances, the present inventor conceived an idea that complementary strand repair can be induced by causing deamination or base excision of intracellular DNA by using a nucleic acid base converting enzyme, during which the DNA can be recombined using homologous recombination by contacting a donor DNA with the DNA. Based on this idea, the inventor conducted further studies. As a result, the inventor has found that homologous recombination of DNA is possible while suppressing cell toxicity by bringing a complex in which a nucleic acid sequence-recognizing module and a nucleic acid base converting enzyme are linked, and a donor DNA containing an insertion sequence into contact with a target DNA, and that, in a preferable embodiment, surprisingly, approximately 100% homologous recombination activity occurs in a targeted site. The present inventor has conducted further studies based on these findings and completed the present invention.

Specifically, the present invention provides the following.

[1] A method for modifying a targeted site of a double-stranded DNA of a cell, comprising a step of bringing a complex in which a nucleic acid sequence-recognizing module that specifically binds to a selected target nucleotide sequence in a double-stranded DNA and a nucleic acid base converting enzyme or DNA glycosylase are linked, and a donor DNA containing an insertion sequence into contact with said double-stranded DNA, to substitute the targeted site with the insertion sequence, or to insert the insertion sequence into said targeted site, without cleaving at least one strand of said double-stranded DNA in the targeted site.

[2] The method of [1], wherein the donor DNA comprises a sequence homologous to a region adjacent to the targeted site.

[3] The method of [1] or [2], wherein the nucleic acid sequence-recognizing module is selected from the group consisting of a CRISPR-Cas system in which at least one DNA cleavage ability of Cas effector protein is inactivated, a zinc finger motif, a TAL effector and a PPR motif.

[4] The method of any of [1] to [3], wherein the nucleic acid sequence-recognizing module is a CRISPR-Cas system in which only one of the two DNA cleavage abilities of the Cas effector protein is inactivated.

[5] The method of any of [1] to [3], wherein the nucleic acid sequence-recognizing module is a CRISPR-Cas system in which both DNA cleavage abilities of the Cas effector protein are inactivated.

[6] The method of any of [1] to [5], wherein the nucleic acid m base converting enzyme is a deaminase.

[7] The method of [6], wherein the deaminase is cytidine deaminase.

[8] The method of [7], wherein the cytidine deaminase is PmCDA1.

[9] The method of any of [1] to [8], wherein the double-stranded DNA is contacted with the complex by introducing a nucleic acid encoding the complex into the cell.

[10] The method of any of [1] to [9], wherein the cell is a prokaryotic cell or a eukaryotic cell.

[11] The method of [10], wherein the cell is a microbial cell.

[12] The method of [10], wherein the cell is a plant cell, an insect cell or an animal cell.

[13] The method of [12], wherein the animal cell is a vertebrate cell.

[14] The method of [13], wherein the vertebrate cell is a mammalian cell.

Advantageous Effects of Invention

According to the present invention, a novel DNA modification technique using a nucleic acid base converting enzyme such as deaminase and the like or DNA glycosylase, wherein the technique is not limited by the type of mutation that can be introduced or the site of mutation, can switch the direction and combination of genes, and can knock-in gene segments is provided. Since the DNA modification technique of the present invention can modify the targeted site without cleaving the double-stranded DNA, unexpected rearrangement and toxicity accompanying the cleavage are suppressed, and the targeted site can be modified much more efficiently compared to the conventional methods.

BRIEF DESCRIPTION OF DRAWINGS

FIG. 2 shows successful introduction of mutation into a targeted site by using dCas9-CDA or nCas9-CDA, and a donor DNA. vector 1525:pRS415_dCas9-CDA+CAN(mut); vector 1526: pRS415_nCas9-CDA+CAN(mut); vector 1059:pRS426_SNR52-Can7R-sgRNA; vector 1149: pRS426_SNR52-Can10R-sgRNA

FIG. 6 shows the results of a demonstration experiment of knock-in or knock-out using the method of FIG. 5.

DESCRIPTION OF EMBODIMENTS

Figure 1:
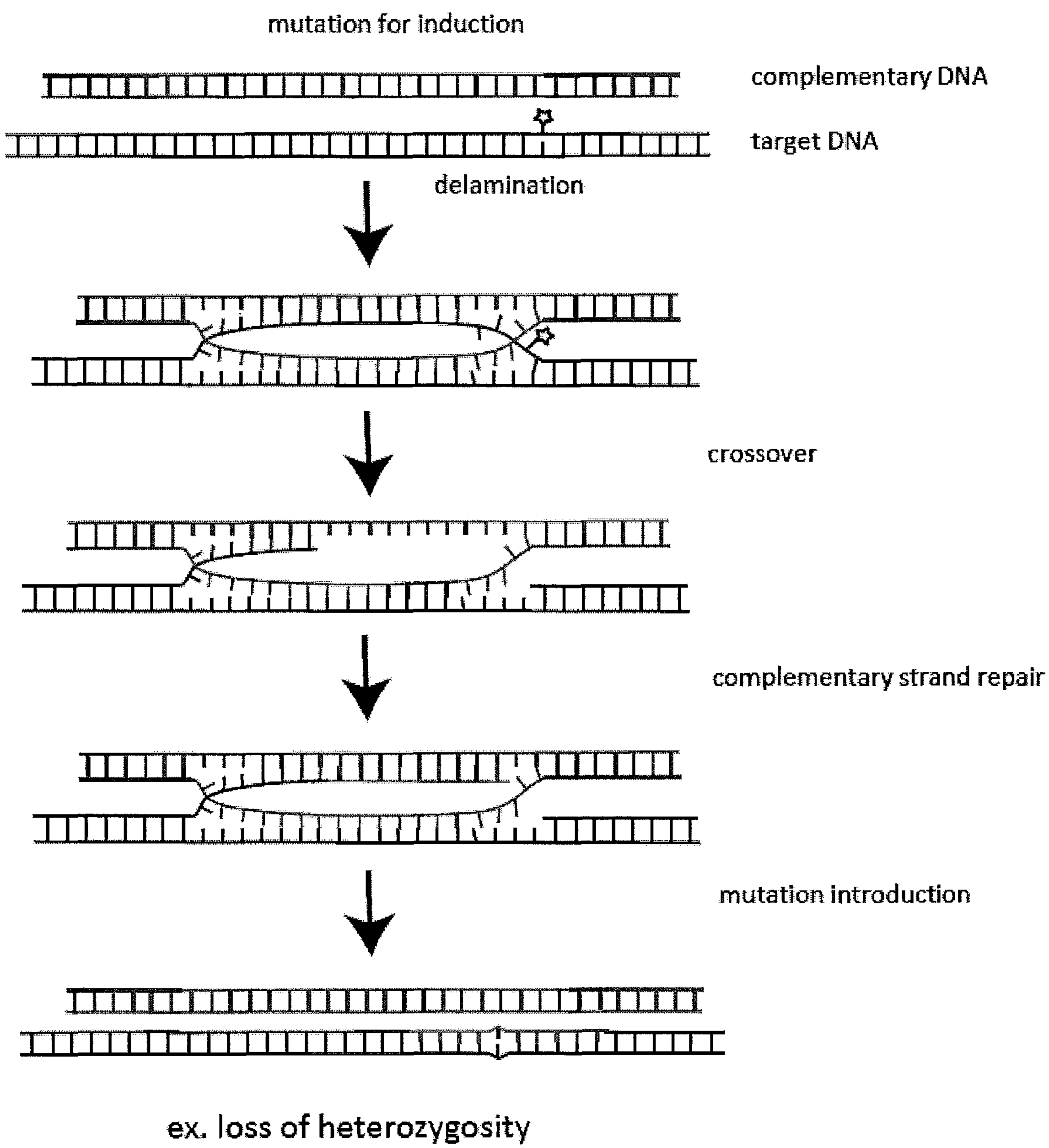
FIG. 1 shows a schematic drawing of the mechanism of genome modification by complementary strand modification. Introduction of a complex in which a nucleic acid sequence-recognizing module and a nucleic acid base converting enzyme or DNA glycosylase are linked, and a donor DNA for recombination into a cell enables highly efficient knock-in of an insertion sequence.
Figure 3:
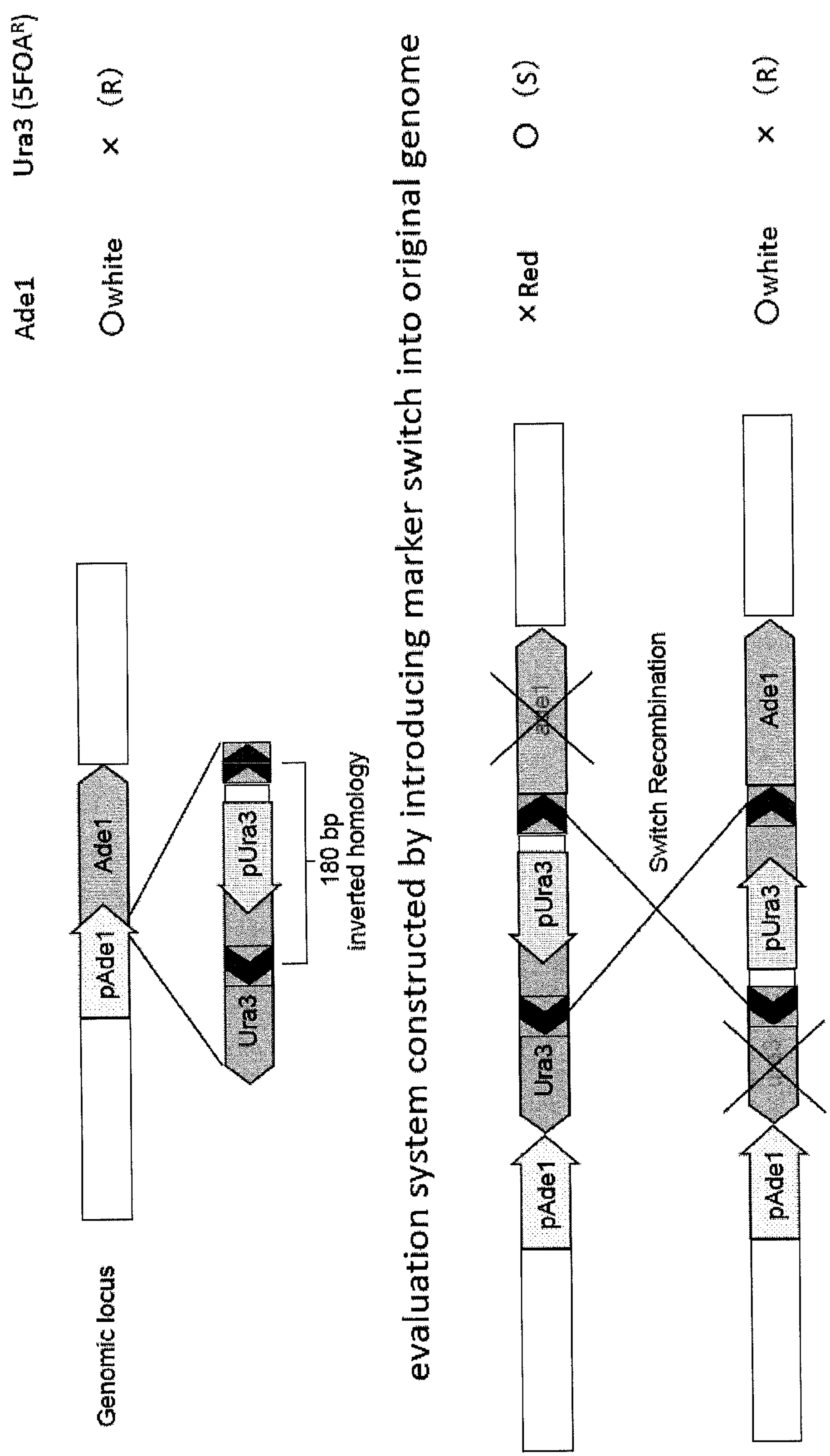
FIG. 3 shows a recombination evaluation system using a budding yeast (BY4741 strain) in which a marker switch has been previously introduced between Ade1 and the promoter region of Ade1. When the marker switch is reversed by recombination in the homologous region, the function of Ade1 is restored and the color of the colony changes from red to white.

The present invention provides a method for modifying a targeted site of a double-stranded DNA by substituting the targeted site in the double-stranded DNA with an insertion sequence contained in an exogenous donor DNA, or inserting the insertion sequence into the targeted site, without cleaving at least one of the strands of a double-stranded DNA (e.g., chromosome DNA, mitochondria DNA, chloroplast DNA; hereinafter these are to be also comprehensively referred to as "genomic DNA") (hereinafter sometimes to be abbreviated as "the method of the present invention"). The method is characterized by a step of bringing a complex of a nucleic acid sequence-recognizing module that specifically binds to the target nucleotide sequence in the double-stranded DNA, and a nucleic acid base converting enzyme or DNA glycosylase (hereinafter sometimes to be abbreviated as "nucleic acid base converting enzyme etc."), and a donor DNA containing an insertion sequence into contact with the double-stranded DNA.

In the present invention, the "modification" of a double-stranded DNA means that a nucleotide (e.g., dA, dC, dG or dT) or a nucleotide sequence on a DNA strand is replaced with another nucleotide or a nucleotide sequence, or that another nucleotide or a nucleotide sequence is inserted between certain nucleotides on a DNA strand. While the double-stranded DNA to be modified is not particularly limited, it is preferably a genomic DNA.

In the present invention, "donor DNA" means a DNA containing an exogenous insertion sequence, and the donor DNA generally contains two kinds of sequences homologous to the sequences (hereinafter sometimes to be referred to as "homology arm") of the two regions on the upstream side and the downstream side of the targeted site adjacent to the targeted site (hereinafter to be also referred to as "adjacent region"). When respective homology arms are distinguished, they may be referred to as "5' homology arm" and "3' homology arm". The "targeted site" of the double-stranded DNA means a region to be substituted by an insertion sequence contained in the donor DNA, or a region between nucleotides into which the insertion sequence is inserted, and the targeted site does not include the aforementioned adjacent sequence.

The sequence homologous to the region adjacent to the targeted site is not only a completely identical sequence but also a sequence having preferably not less than 80% (e.g., not less than 85%, not less than 90%, not less than 95%, not less than 96%, not less than 97%, not less than 98%, not less than 99%) identity with the completely identical sequence, as long as homologous recombination can occur in a cell.

The insertion sequence may contain, where necessary, a drug resistance gene (e.g., kanamycin resistance gene, ampicillin resistance gene, puromycin resistance gene and the like), a selection marker sequence such as a thymidine kinase gene, a diphtheria toxin gene and the like, a reporter gene sequence such as a green fluorescent protein (GFP), red fluorescent protein, β-glucuronidase (GUS), FLAG, and the like. Moreover, a LoxP sequence, a FRT sequence, or a transposon specific terminal insertion sequence (PiggyBac Terminal Repeat) may be provided before and after the gene so that these genes can be excised after cell sorting or the like is completed. Examples of preferred transposon include piggyBac, which is a transposon derived from the Lepidoptera insect, and the like (Kaji, K. et al., Nature, 458: 771-775 (2009), Woltjen et al., Nature, 458: 766-770 (2009), WO 2010/012077). Alternatively, as described in Oji A et al., Sci Rep, 6: 31666 (2016) and the like, an expression vector containing the above-mentioned drug resistance gene is co-transfected, and transient (about several days) drug selection may be performed. Whether the insertion sequence is inserted into the targeted site or substituted with the targeted site can be confirmed by decoding the sequence and screening for chromosomal DNA separated and extracted from cells by Southern hybridization or PCR method or the like. When the above-mentioned drug resistance gene or the like is present in the donor DNA, confirmation can also be performed using the expression thereof as an index.

The donor DNA may be linear (e.g., synthetic double-stranded DNA), circular (e.g., plasmid DNA), or. single-stranded DNA (e.g., single-stranded oligodeoxynucleotide) (ssODN)) or a double-stranded DNA. The donor DNA can be appropriately designed depending on the base length of the insertion sequence, homologous recombination activity of the host cell, and the like. For example, when the insertion sequence is 100 bases in length or shorter, ssODN or synthetic double-stranded DNA is generally used, and when it is longer than that, usually, synthetic double-stranded DNA or plasmid DNA is generally used. Also, the length of the donor DNA is not particularly limited, and can be appropriately designed depending on the length of the insertion sequence and the like. The length of the insertion sequence is not particularly limited, and it can be appropriately designed generally within the range of 1 to tens of thousands of bases (e.g., in the case of ssODN, not more than 100 bases in length (e.g., not more than 70 bases, not more than 50 bases)) according to the purposes. Also, the length of each homology arm is not particularly limited. When the donor DNA is ssODN, one with a length of 10 bases to 150 bases is generally used. When the donor DNA is synthetic double-stranded DNA, one with a length of 10 bases to 5000 bases is generally used, and when the donor DNA is plasmid DNA, one with a length of 100 bases to 5000 bases, preferably 500 bases to 1000 bases, is generally used. These donor DNAs can be designed by referring to known literatures (e.g., Ochiai H, Int J Mol Sci, 16:21128-21137 (2015), Hockemeyer D et al., Nat Biotefchnol, 27:851-857 (2009)).

In the present invention, the "nucleic acid sequence-recognizing module" means a molecule or molecule complex having an ability to specifically recognize and bind to a particular nucleotide sequence (i.e., target nucleotide sequence) on a DNA strand. Binding of the nucleic acid sequence-recognizing module to a target nucleotide sequence enables a nucleic acid base converting enzyme etc. linked to the module to specifically act on a site targeted by a nucleic acid base converting enzyme and the like of a double-stranded DNA (i.e., target nucleotide sequence and nucleotide in the vicinity thereof).

As shown in the below-mentioned Examples, it has been demonstrated that a targeted site can be modified by introducing a complex of a nucleic acid base converting enzyme and a nucleic acid sequence-recognizing module, and a donor DNA into a cell. While not wishing to be bound by any theory, the mechanism of targeted site modification by the method is assumed to be as follows. A base present in the site targeted by the nucleic acid base converting enzyme is converted to another base, the converted base is removed by DNA glycosylase, an abasic site (apurinic/apyrimidic (AP) site) resulting from the base excision reaction by the enzyme is treated by an enzyme at the downstream of the base excision repair (BER) pathway such as an AP endonuclease, DNA polymerase, DNA ligase and the like. On the other hand, the presence of abnormal nucleotide or mismatched structure without BER completion also activates the complementary strand repair pathway, causing homologous recombination between the targeted site and the region contained in the donor DNA, whereby the modification of the targeted site has occurred. Therefore, even when DNA glycosylase is used, it is assumed that the same modification occurs by causing base excision at a site targeted by the enzyme. Thus, not only nucleic acid base converting enzyme but also DNA glycosylase can be applied to the method of the present invention.

In the present invention, the "nucleic acid base converting enzyme" means an enzyme capable of converting a target nucleotide to other nucleotide by catalyzing a reaction for converting a substituent on a purine or pyrimidine ring on a DNA base to other group or atom, without cleaving the DNA strand.

In the present invention, "DNA glycosylase" means an enzyme that hydrolyzes N-glycosidic bond of DNA. DNA glycosylase originally plays a role of removing damaged base from DNA in BER. In the present invention, one capable of acting on normal bases in DNA (that is, dC, dT, dA or dG, or those that underwent epigenetic modification) is preferred. A mutated DNA glycosylase that does not originally react with normal base or has low reactivity, but has acquired reactivity with normal base due to mutation or has improved reactivity is also included in the DNA glycosylase of the present invention, and can be preferably used. A site without a base (apurinic/apyrimidic (AP) site) generated as a result of the base excision reaction by the enzyme is treated by an enzyme downstream of the BER pathway such as an AP endonuclease, DNA polymerase, DNA ligase and the like.

In addition, "sufficiently low reactivity with DNA having a double helix structure without distortion" means that a base excision reaction occurs in regions where DNA having a double helix structure without distortion is formed, only at a frequency that suppresses cytotoxicity to a level that does not affect cell viability. As used herein, the "DNA having a double helix structure without distortion" means that a strong double helix structure is formed (i.e., unrelaxed double-helical DNA (or to be also simply referred to as unrelaxed DNA)), and not only the state of single-stranded DNA in which the bases forming pairs are completely dissociated, but also the state of relaxed double-stranded DNA in which base pairs are formed but the double helix structure is unwound are not included. Examples of the DNA glycosylase with sufficiently low reactivity with DNA having a double helix structure without distortion include a DNA glycosylase inherently having sufficiently low reactivity with DNA having a double helix structure without distortion, a mutated DNA glycosylase into which a mutation that lowers reactivity with DNA having a double helix structure without distortion as compared to the wild-type has been introduced and the like. Furthermore, a DNA glycosylase divided into two segments which is a split enzyme designed such that each segment is bound to either of two divided nucleic acid sequence recognition modules to form two complexes, the nucleic acid sequence-recognizing module can specifically bind to a target nucleotide sequence when the both complexes are refolded, and the DNA glycosylase can catalyze a base excision reaction by the specific binding is also encompassed in the "DNA glycosylase with sufficiently low reactivity with DNA having a double helix structure without distortion" of the present invention.

In the present invention, the "nucleic acid-modifying enzyme complex" means a molecular complex comprising a complex comprising the above-mentioned nucleic acid sequence-recognizing module and nucleic acid base converting enzyme or DNA glycosylase are connected, and having a catalyst function of a nucleic acid base conversion reaction or a base excision reaction and imparted with a particular nucleotide sequence recognition ability. The "complex" here encompasses not only one constituted of multiple molecules, but also one having a nucleic acid sequence-recognizing module and a nucleic acid base converting enzyme etc. in a single molecule, like a fusion protein.

The nucleic acid base converting enzyme to be used in the present invention is not particularly limited as long as it can catalyze the above-mentioned reaction, and examples thereof include deaminase belonging to the nucleic acid/nucleotide deaminase superfamily, which catalyzes a deamination reaction that converts an amino group to a carbonyl group. Preferable examples thereof include cytidine deaminase capable of converting cytosine or 5-methylcytosine to uracil or thymine, respectively, adenosine deaminase capable of converting adenine to hypoxanthine, guanosine deaminase capable of converting guanine to xanthine and the like. As cytidine deaminase, more preferred is activation-induced cytidine deaminase (hereinafter to be also referred to as AID) which is an enzyme that introduces a mutation into an immunoglobulin gene in the acquired immunity of vertebrata or the like.

While the derivation of nucleic acid base converting enzyme is not particularly limited, for example, PmCDA1 (*Petromyzon marinus* cytosine deaminase 1) derived from *Petromyzon marinus*, or AID (Activation-induced cytidine deaminase; AICDA) derived from mammal (e.g., human, swine, bovine, horse, monkey etc.) can be used. For example, GenBank accession Nos. EF094822 and ABO15149 can be referred to for the base sequence and amino acid sequence of cDNA of PmCDA1, GenBank accession No. NM_020661 and NP_065712 can be referred to for the base sequence and amino acid sequence of cDNA of human AID. From the aspect of enzyme activity, PmCDA1 is preferred.

The DNA glycosylase to be used in the present invention is not particularly limited as long as it can catalyze a reaction to hydrolyze the N-glycosidic bond of DNA and eliminate the base. To enhance broad utility as a genome editing technique, preferred are those which can act on normal bases (i.e., dC, dT, dA or dG, or those obtained by epigenetic modification, for example, 5-methylcytosine etc.). Examples of such enzyme include an enzyme having CDG activity that catalyzes a reaction to remove cytosine, an enzyme that has TDG activity that catalyzes a reaction to remove thymine, an enzyme that has an activity to remove 5-methylcytosine (5-mCDG activity) and the like. Specifically, thymine DNA glycosylase, oxoguanine glycosylase, alkyladenine DNA glycosylase (e.g., yeast 3-methyladenine-DNA glycosylase (MAG1) etc.) and the like can be mentioned. The present inventor previously reported that use of a DNA glycosylase with sufficiently low reactivity with DNA having a double helix structure without distortion (unrelaxed DNA) as DNA glycosylase can reduce cytotoxicity and efficiently modify a target sequence (WO 2016/072399). Therefore, as DNA glycosylase, a DNA glycosylase with sufficiently low reactivity with DNA having a double helix structure without distortion is preferably used. Examples of such DNA glycosylase include a mutant of UNG having cytosine-DNA glycosylase (CDG) activity and/or thymine-DNA glycosylase (TDG) activity (uracil-DNA glycosylase), and UDG mutant from vaccinia virus, which are described in WO 2016/072399.

Specific examples of the aforementioned mutant of UNG include yeast UNG1 N222D/L304A double mutant, N222D/R308E double mutant, N222D/R308C double mutant, Y164A/L304A double mutant, Y164A/R308E double mutant, Y164A/R308C double mutant, Y164G/L304A double mutant, Y164G/R308E double mutant, Y164G/R308C double mutant, N222D/Y164A/L304A triple mutant, N222D/Y164A/R308E triple mutant, N222D/Y164A/R308C triple mutant, N222D/Y164G/L304A triple mutant, N222D/Y164G/R308E triple mutant, N222D/Y164G/R308C triple mutant and the like. When another UNG is used in place of the yeast UNG1, a mutant in which a similar mutation has been introduced into the amino acid corresponding to each mutant described above may be used. For example, as a mutation of *E. coli* UNG corresponding to Y164A or Y164G mutation of yeast UNG1, which is a mutation imparting TDG activity, Y66A or Y66G can be mentioned and, as a mutation of human UNG, Y147A or Y147G can be mentioned. As a mutation of *Escherichia coli* UNG corresponding to N222D mutation of yeast UNG1, which is a mutation imparting CDG activity, N123D can be mentioned and, as a mutation of human UNG, N204D can be mentioned. As a mutation of *Escherichia coli* UNG corresponding to L304A, R308E or R3080 mutation of yeast UNG1, which decreases reactivity with DNA having a double helix structure without distortion, L191A, R195E or R195C can be mentioned and, as a mutation of human UNG, L272A, R276E or R276C can be mentioned. As UDG mutant from vaccinia virus, N120D mutant (to which CDG activity is imparted), Y70G mutant (to which TDG activity is imparted), Y70A mutant (to which TDG activity is imparted), N120D/Y70G double mutant, N120D/Y70A double mutant and the like can be mentioned. Alternatively, it may be a DNA glycosylase divided into two segments which is a split enzyme designed such that each segment is bound to either of two divided nucleic acid sequence recognition modules to form two complexes, the nucleic acid sequence-recognizing module can specifically bind to a target nucleotide sequence when both complexes are refolded, and the DNA glycosylase can catalyze a base excision reaction by the specific binding. The split enzyme can be designed and produced by referring to the descriptions of, for example, WO 2016/072399, Nat Biotechnol. 33(2): 139-142 (2015), PNAS 112(10): 2984-2989 (2015).

While the derivation of UNG is not particularly limited, for example, ung from *Escherichia coli* (Varshney, U. et al. (1988) J. Biol. Chem., 263, 7776-7784), UNG1 or UNG2 derived from yeast, mammal (e.g., human, mouse, swine, bovine, horse, monkey etc.) or the like, or UDG derived from virus (e.g., Poxviridae (vaccinia virus etc.), Herpesviridae and the like) can be used.

A target nucleotide sequence in a double-stranded DNA to be recognized by the nucleic acid sequence-recognizing module in the nucleic acid-modifying enzyme complex of the present invention is not particularly limited as long as the module specifically binds to, and may be any sequence in the double-stranded DNA. The length of the target nucleotide sequence only needs to be sufficient for specific binding of the nucleic acid sequence-recognizing module. For example, when mutation is introduced into a particular site in the genomic DNA of a mammal, it is not less than 12 nucleotides, preferably not less than 15 nucleotides, more preferably not less than 17 nucleotides, according to the genome size thereof. While the upper limit of the length is not particularly limited, it is preferably not more than 25 nucleotides, more preferably not more than 22 nucleotides. As shown in the Examples below, high modification efficiency was demonstrated in any of the experimental systems in which the target nucleotide sequence is present in the targeted site, a sequence homologous to the homology arm, and a region containing a partial sequence homologous to the homology arm. Therefore, the target nucleotide sequence may be present at the targeted site, may be present in at least a part of the region of a sequence homologous to the homology arm, or may be present in a region near a sequence homologous to the homology arm.

As the nucleic acid sequence-recognizing module in the nucleic acid-modifying enzyme complex of the present invention, a CRISPR-Cas system wherein at least one DNA cleavage ability of the Cas effector protein (hereinafter to be also referred to as Cas nuclease) is inactivated (hereinafter to be also referred to as "CRISPR-mutant Cas"), zinc finger motif, TAL (transcription activator-like) effector and PPR (pentatricopeptide repeat) motif and the like, as well as a fragment which contains a DNA binding domain of a protein that specifically binds to DNA, such as restriction enzyme, transcription factor, RNA polymerase and the like, and does not have a DNA double strand cleavage ability and the like can be used, but the module is not limited thereto. Preferably, CRISPR-mutant Cas, zinc finger motif, TAL effector, PPR motif and the like can be mentioned. In the present specification, the aforementioned Cas effector protein in which at least one DNA cleavage ability is inactivated is also referred to as Cas effector protein mutant.

A zinc finger motif is constituted by linkage of 3-6 different Cys2His2 type zinc finger units (1 finger recognizes about 3 bases), and can recognize a target nucleotide sequence of 9-18 bases. A zinc finger motif can be produced by a known method such as Modular assembly method (Nat Biotechnol (2002) 20: 135-141), OPEN method (Mol Cell (2008) 31: 294-301), CoDA method (Nat Methods (2011) 8: 67-69), *Escherichia coli* one-hybrid method (Nat Biotechnol (2008) 26:695-701) and the like. JP-B-4968498 can be referred to as for the detail of the zinc finger motif production.

A TAL effector has a module repeat structure with about 34 amino acids as a unit, and the 12th and 13th amino acid residues (called RVD) of one module determine the binding stability and base specificity. Since each module is highly independent, TAL effector specific to a target nucleotide sequence can be produced by simply connecting the module. For TAL effector, a production method utilizing an open resource (REAL method (Curr Protoc Mol Biol (2012) Chapter 12: Unit 12.15), FLASH method (Nat Biotechnol (2012) 30: 460-465), and Golden Gate method (Nucleic Acids Res (2011) 39: e82) etc.) have been established, and a TAL effector for a target nucleotide sequence can be designed comparatively conveniently. National Publication of International Patent Application No. 2013-513389 can be referred to as for the detail of the production of a TAL effector.

PPR motif is constituted such that a particular nucleotide sequence is recognized by a continuation of PPR motifs each consisting of 35 amino acids and recognizing one nucleic acid base, and recognizes a target base only by 1, 4 and ii(−2) amino acids of each motif. Motif constitution has no dependency, and is free of interference of motifs on both sides. Therefore, like TAL effector, a PPR protein specific to the target nucleotide sequence can be produced by simply connecting PPR motifs. JP-A-2013-128413 can be referred to as for the detail of the production of a PPR motif.

When a fragment of restriction enzyme, transcription factor, RNA polymerase and the like is used, since the DNA binding domains of these proteins are well known, a fragment which contains the domain and does not have a DNA double strand cleavage ability, can be easily designed and constructed.

Any of the above-mentioned nucleic acid sequence-recognizing module can be provided as a fusion protein with the above-mentioned nucleic acid base converting enzyme etc., or a protein binding domain such as SH3 domain, PDZ domain, GK domain, GB domain and the like and a binding partner thereof may be fused with a nucleic acid sequence-recognizing module and a nucleic acid base converting enzyme etc., respectively, and provided as a protein complex via an interaction of the domain and a binding partner thereof. Alternatively, a nucleic acid sequence-recognizing module and a nucleic acid base converting enzyme etc. may be each fused with intein, and they can be linked by ligation after protein synthesis.

The nucleic acid-modifying enzyme complex of the present invention containing a complex (including fusion protein) wherein a nucleic acid sequence-recognizing module and a nucleic acid base converting enzyme are linked is desirably contacted with a double stranded DNA by introducing a nucleic acid encoding the complex into a cell having the double stranded DNA of interest (e.g., genomic DNA). In the present specification, a nucleic acid encoding a nucleic acid modification enzyme complex includes a base sequence encoding a nucleic acid sequence recognition module, and a base sequence encoding a nucleic acid base converting enzyme or DNA glycosylase. When the nucleic acid sequence recognition module is CRISPR-Cas system, it further contains a sequence encoding guide RNA.

Therefore, the nucleic acid sequence-recognizing module and the nucleic acid base converting enzyme etc. are preferably prepared as a nucleic acid encoding a fusion protein thereof, or in a form capable of forming a complex in a host cell after translation into a protein by utilizing a binding domain, intein and the like, or as a nucleic acid encoding each of them. The nucleic acid here may be a DNA or an RNA. When it is a DNA, it is preferably a double stranded DNA, and provided in the form of an expression vector disposed under regulation of a functional promoter in a host cell. When it is an RNA, it is preferably a single strand RNA.

Since the complex of the present invention wherein a nucleic acid sequence-recognizing module and a nucleic acid base converting enzyme etc. are linked does not accompany double-stranded DNA breaks (DSB), genome editing with low toxicity is possible, and the method of the present invention can be applied to a wide range of biological materials. Therefore, the cells to be introduced with nucleic acid encoding nucleic acid sequence-recognizing module and/or nucleic acid base converting enzyme etc. can encompass cells of any species, from bacterium of *Escherichia coli* and the like which are prokaryotes, cells of microorganism such as yeast and the like which are lower eukaryotes, to cells of higher eukaryotes such as vertebrata including mammals such as human and the like, insect, plant and the like.

A DNA encoding a nucleic acid sequence-recognizing module such as zinc finger motif, TAL effector, PPR motif and the like can be obtained by any method mentioned above for each module. A DNA encoding a sequence-recognizing module of restriction enzyme, transcription factor, RNA polymerase and the like can be cloned by, for example, synthesizing an oligoDNA primer m covering a region encoding a desired part of the protein (part containing DNA binding domain) based on the cDNA sequence information thereof, and amplifying by the RT-PCR method using, as a template, the total RNA or mRNA fraction prepared from the protein-producing cells.

A DNA encoding a nucleic acid base converting enzyme etc. (i.e., DNA encoding nucleic acid base converting enzyme or DNA encoding DNA glycosylase) can also be cloned similarly by synthesizing an oligoDNA primer based on the cDNA sequence information thereof, and amplifying by the RT-PCR method using, as a template, the total RNA or mRNA fraction prepared from the enzyme-producing cells. For example, a DNA encoding PmCDA1 of *Petromyzon marinus* can be cloned by designing suitable primers for the upstream and downstream of CDS based on the cDNA sequence (accession No. EF094822) registered in the NCBI database, and cloning from mRNA from *Petromyzon marinus* by the RT-PCR method. A DNA encoding human AID can be cloned by designing suitable primers for the upstream and downstream of CDS based on the cDNA sequence (accession No. AB040431) registered in the NCBI database, and cloning from, for example, mRNA from human lymph node by the RT-PCR method. Also, the donor DNA can be cloned in the same manner as described above based on the sequence information of the targeted site and the like.

The cloned DNA may be directly, or after digestion with a restriction enzyme when desired, or after addition of a suitable linker and/or a nuclear localization signal (each organelle transfer signal when the double-stranded DNA of interest is mitochondria or chloroplast DNA), ligated with a DNA encoding a nucleic acid sequence-recognizing module to prepare a DNA encoding a fusion protein. Alternatively, a DNA encoding a nucleic acid sequence-recognizing module, and a DNA encoding a nucleic acid base converting enzyme etc. may be each fused with a DNA encoding a binding domain or a binding partner thereof, or both DNAs may be fused with a DNA encoding a m separation intein, whereby the nucleic acid sequence-recognizing conversion module and the nucleic acid base converting enzyme etc. are translated in a host cell to form a complex. In these cases, a linker and/or a nuclear localization signal can be linked to a suitable position of one of or both DNAs when desired. The donor DNA may be prepared as a single DNA, or may be provided as a single DNA with a nucleic acid encoding a nucleic acid sequence recognition module and/or a nucleic acid base converting enzyme and the like.

A DNA encoding a nucleic acid sequence-recognizing module, a DNA encoding nucleic acid base converting enzyme etc., and a donor DNA can be obtained by chemically synthesizing the DNA strand, or by connecting synthesized partly overlapping oligoDNA short strands by utilizing the PCR method and the Gibson Assembly method to construct a DNA encoding the full length thereof. When the donor DNA is a single-stranded nucleic acid, as a method other than chemically synthesizing a DNA strand, for example, a plasmid DNA containing the DNA is digested with a restriction enzyme into a single strand, RNA is synthesized by RNA polymerase, after which cDNA is synthesized with reverse transcriptase and the RNA strand is differentiated with RNaseH. Alternatively, it can be prepared by digesting a plasmid containing a donor DNA with a nickase-type restriction enzyme, and separating and purifying same by electrophoresis. The advantage of constructing a full-length DNA by chemical synthesis or a combination of PCR method or Gibson Assembly method is that the codon to be used can be designed in CDS full-length according to the host into which the DNA is introduced. In the expression of a heterologous DNA, the protein expression level is expected to increase by converting the DNA sequence thereof to a codon highly frequently used in the host organism. As the data of codon use frequency in host to be used, for example, the genetic code use frequency database disclosed in the home page of Kazusa DNA Research Institute (www.kazusa.or.jp/codon/index.html) can be used, or documents showing the codon use frequency in each host may be referred to. By reference to the obtained data and the DNA sequence to be introduced, codons showing low use frequency in the host from among those used for the DNA sequence may be converted to a codon coding the same amino acid and showing high use frequency.

When a site other than the target nucleotide sequence and the PAM sequence is used as the targeted site, these sequences may remain even after modification, and a nucleic acid base conversion reaction or a base excision reaction may occur due to a nucleic acid modifying enzyme and the like. Therefore, it is preferable to design the donor DNA such that these sequences would be removed, or introduce a silent mutation into the target nucleotide sequence or the PAM sequence on the homology arm.

An expression vector containing a DNA encoding a nucleic acid sequence-recognizing module and/or a nucleic acid base converting enzyme etc. can be produced, for example, by linking the DNA to the downstream of a promoter in a suitable expression vector.

As the expression vector, plasmids from *Escherichia coli* (e.g., pBR322, pBR325, pUC12, pUC13); plasmids from *Bacillus subtilis* (e.g., pUB110, pTP5, pC194); plasmids from yeast (e.g., pSH19, pSH15); insect cell expression plasmids (e.g., pFast-Bac); animal cell expression plasmids (e.g., pA1-11, pXT1, pRc/CMV, pRc/RSV, pcDNAI/Neo); bacteriophages such as λphage and the like; insect virus vectors such as baculovirus and the like (e.g., BmNPV, AcNPV); animal virus vectors such as retrovirus, vaccinia virus, adenovirus and the like, and the like are used.

As the promoter, any promoter appropriate for a host used for gene expression can be used. In a conventional method involving DSB, since the survival rate of the host cell sometimes decreases markedly due to the toxicity, it is desirable to increase the number of cells by the start of the induction by using an inductive promoter. However, since sufficient cell proliferation can also be achieved by expressing the nucleic acid-modifying enzyme complex of the present invention, a constitutive promoter can also be used without limitation.

For example, when the host is an animal cell, SRα promoter, SV40 promoter, LTR promoter, CMV (cytomegalovirus) promoter, RSV (Rous sarcoma virus) promoter, MoMuLV (Moloney mouse leukemia virus) LTR, HSV-TK (simple herpes virus thymidine kinase) promoter and the like are used. Of these, CMV promoter, SRα promoter and the like are preferable.

When the host is *Escherichia coli*, trp promoter, lac promoter, recA promoter, $\lambda P_L$ promoter, lpp promoter, T7 promoter and the like are preferable.

When the host is genus *Bacillus*, SPO1 promoter, SPO2 promoter, penP promoter and the like are preferable.

When the host is a yeast, the Gal1/10 promoter, PHO5 promoter, PGK promoter, GAP promoter, ADH promoter and the like are preferable.

When the host is an insect cell, a polyhedrin promoter, P10 promoter and the like are preferable.

When the host is a plant cell, CaMV35S promoter, CaMV19S promoter, NOS promoter and the like are preferable.

As the expression vector, besides those mentioned above, one containing an enhancer, a splicing signal, a terminator, a polyA addition signal, a selection marker such as drug resistance gene, an auxotrophic complementary gene and the like, a replication origin and the like on demand can be used.

An RNA encoding a nucleic acid sequence-recognizing module and/or a nucleic acid base converting enzyme etc. can be prepared by, for example, transcription to mRNA in an in vitro transcription system known per se by using a vector encoding DNA encoding the above-mentioned nucleic acid sequence-recognizing module and/or a nucleic acid base converting enzyme etc. as a template.

A complex of a nucleic acid sequence-recognizing module and a nucleic acid base converting enzyme etc. can be intracellularly expressed by introducing an expression vector containing a DNA encoding a nucleic acid sequence-recognizing module and/or a nucleic acid base converting enzyme etc. into a host cell, and culturing the host cell.

As the host, genus *Escherichia*, genus *Bacillus*, yeast, insect cell, insect, animal cell and the like are used.

As the genus *Escherichia, Escherichia coli* K12●DH1 [Proc. Natl. Acad. Sci. USA, 60, 160 (1968)], *Escherichia coli* JM103 [Nucleic Acids Research, 9, 309 (1981)], *Escherichia coli* JA221 [Journal of Molecular Biology, 120, 517 (1978)], *Escherichia coli* HB101 [Journal of Molecular Biology, 41, 459 (1969)], *Escherichia coli* C600 [Genetics, 39, 440 (1954)] and the like are used.

As the genus *Bacillus, Bacillus subtilis* MI114 [Gene, 24, 255 (1983)], *Bacillus subtilis* 207-21 [Journal of Biochemistry, 95, 87 (1984)] and the like are used.

As the yeast, *Saccharomyces cerevisiae* AH22, AH22R$^-$, NA87-11A, DKD-5D, 20B-12, *Schizosaccharomyces pombe* NCYC1913, NCYC2036, *Pichia pastoris* KM71 and the like are used.

As the insect cell, when the virus is AcNPV, cells of established line from cabbage armyworm larva (*Spodoptera frugiperda* cell; Sf cell), MG1 cells from the mid-intestine of *Trichoplusia ni*, High Five™ cells from an egg of *Trichoplusia ni*, cells from *Mamestra brassicae*, cells from *Estigmena acrea* and the like are used. When the virus is BmNPV, cells of established line from *Bombyx mori* (*Bombyx mori* N cell; BmN cell) and the like are used as insect cells. As the Sf cell, for example, Sf9 cell (ATCC CRL1711), Sf21 cell [all above, In Vivo, 13, 213-217 (1977)] and the like are used.

As the insect, for example, larva of *Bombyx mori, Drosophila*, cricket and the like are used [Nature, 315, 592 (1985)].

As the animal cell, cell lines such as monkey COS-7 cell, monkey Vero cell, Chinese hamster ovary (CHO) cell, dhfr gene-deficient CHO cell, mouse L cell, mouse AtT-20 cell, mouse myeloma cell, rat GH3 cell, cell from human fetal kidney (e.g., HEK293 cell), cell from human liver cancer (e.g., HepG2), human FL cell and the like, pluripotent stem cells such as iPS cell, ES cell and the like of human and other mammals, and primary cultured cells prepared from various tissues are used. Furthermore, zebrafish embryo, *Xenopus* oocyte and the like can also be used.

As the plant cell, suspended cultured cells, callus, protoplast, leaf segment, root segment and the like prepared from various plants (e.g., grain such as rice, wheat, corn and the like, product crops such as tomato, cucumber, egg plant and the like, garden plants such as carnation, *Eustoma russellianum* and the like, experiment plants such as tobacco, *Arabidopsis thaliana* and the like, and the like) are used.

An expression vector can be introduced by a known method (e.g., lysozyme method, competent method, PEG method, $CaCl_2$ coprecipitation method, electroporation method, the microinjection method, the particle gun method, lipofection method, *Agrobacterium* method and the like) according to the kind of the host. Donor DNA can also be introduced into cells by a similar method. When introducing the expression vector and the donor DNA as different molecules, the introduction of the expression vector and the donor DNA may be performed simultaneously or at different timings.

*Escherichia coli* can be transformed according to the methods described in, for example, Proc. Natl. Acad. Sci. USA, 69, 2110 (1972), Gene, 17, 107 (1982) and the like.

The genus *Bacillus* can be introduced into a vector according to the methods described in, for example, Molecular & General Genetics, 168, 111 (1979) and the like.

A yeast can be introduced into a vector according to the methods described in, for example, Methods in Enzymology, 194, 182-187 (1991), Proc. Natl. Acad. Sci. USA, 75, 1929 (1978) and the like.

An insect cell and an insect can be introduced into a vector according to the methods described in, for example, Bio/Technology, 6, 47-55 (1988) and the like.

An animal cell can be introduced into a vector according to the methods described in, for example, Cell Engineering additional volume 8, New Cell Engineering Experiment Protocol, 263-267 (1995) (published by Shujunsha), and Virology, 52, 456 (1973).

A cell introduced with a vector and a donor DNA can be cultured according to a known method according to the kind of the host.

For example, when *Escherichia coli* or genus *Bacillus* is cultured, a liquid medium is a preferable medium to be used for the culture. The medium preferably contains a carbon source, a nitrogen source, an inorganic substance and the like necessary for the growth of a transformant. Examples of the carbon source include glucose, dextrin, soluble starch, sucrose and the like; examples of the nitrogen source include inorganic or organic substances such as ammonium salts, nitrate salts, corn steep liquor, peptone, casein, meat extract, soybean cake, potato extract and the like; and examples of the inorganic substance include calcium chloride, sodium dihydrogen phosphate, magnesium chloride and the like. The medium may contain yeast extract, vitamins, growth promoting factor and the like. The pH of the medium is preferably about 5 to about 8.

As a medium for culturing *Escherichia coli*, for example, M9 medium containing glucose, casamino acid [Journal of Experiments in Molecular Genetics, 431-433, Cold Spring Harbor Laboratory, New York 1972] is preferable. Where necessary, for example, agents such as 3β-indolylacrylic acid may be added to the medium to ensure an efficient function of a promoter. *Escherichia coli* is cultured at generally about 15 to about 43° C. Where necessary, aeration and stirring may be performed.

The genus *Bacillus* is cultured at generally about 30 to about 40° C. Where necessary, aeration and stirring may be performed.

Examples of the medium for culturing yeast include Burkholder minimum medium [Proc. Natl. Acad. Sci. USA, 77, 4505 (1980)], SD medium containing 0.5% casamino acid [Proc. Natl. Acad. Sci. USA, 81, 5330 (1984)] and the like. The pH of the medium is preferably about 5 to about 8. The culture is performed at generally about 20° C. to about 35° C. Where necessary, aeration and stirring may be performed.

As a medium for culturing insect cells or insects, for example, Grace's Insect Medium [Nature, 195, 788 (1962)] containing an additive such as inactivated 10% bovine serum and the like as appropriate and the like are used. The pH of the medium is preferably about 6.2 to about 6.4. The culture is performed at generally about 27° C. Where necessary, aeration and stirring may be performed.

As a medium for culturing animal cells, for example, minimum essential medium (MEM) containing about 5 to about 20% of fetal bovine serum [Science, 122, 501 (1952)], Dulbecco's modified Eagle medium (DMEM) [Virology, 8, 396 (1959)], RPMI 1640 medium [The Journal of the American Medical Association, 199, 519 (1967)], 199 medium [Proceeding of the Society for the Biological Medicine, 73, 1 (1950)] and the like are used. The pH of the medium is preferably about 6 to about 8. The culture is performed at generally about 30° C. to about 40° C. Where necessary, aeration and stirring may be performed.

As a medium for culturing plant cells, for example, MS medium, LS medium, B5 medium and the like are used. The pH of the medium is preferably about 5 to about 8. The culture is performed at generally about 20° C. to about 30° C. Where necessary, aeration and stirring may be performed.

As mentioned above, a complex of a nucleic acid sequence-recognizing module and a nucleic acid base converting enzyme etc., i.e., nucleic acid-modifying enzyme complex, can be expressed intracellularly.

An RNA encoding a nucleic acid sequence-recognizing module and/or a nucleic acid base converting enzyme etc. can be introduced into a host cell by microinjection method, lipofection method and the like. RNA introduction can be performed once or repeated multiple times (e.g., 2 to 5 times) at suitable intervals.

As for zinc finger motifs, production of many actually functionable zinc finger motifs is not easy, since production efficiency of a zinc finger that specifically binds to a target nucleotide sequence is not high and selection of a zinc finger having high binding specificity is complicated. While TAL effectors and PPR motifs have a high degree of freedom of target nucleic acid sequence recognition as compared to zinc finger motifs, a problem remains in the efficiency since a large protein needs to be designed and constructed every time according to the target nucleotide sequence.

In contrast, since the CRISPR-Cas system recognizes the double-stranded DNA sequence of interest with a guide RNA complementary to the target nucleotide sequence, any sequence can be targeted by simply synthesizing an oligoDNA capable of specifically hybridizing with the target nucleotide sequence.

Therefore, in a more preferable embodiment of the present invention, a CRISPR-Cas system wherein DNA cleavage ability of only one or both of the Cas effector proteins is inactivated (CRISPR-mutant Cas) is used as a nucleic acid sequence-recognizing module.

The nucleic acid sequence-recognizing module of the present invention using CRISPR-mutant Cas is provided as a complex of a CRISPR-RNA (crRNA) containing a sequence complementary to the target nucleotide sequence and, where necessary, trans-activating RNA (tracrRNA) necessary for recruiting mutant Cas effector protein (when tracrRNA is necessary, possibly provided as chimeric RNA with crRNA) and mutant Cas effector protein. An RNA molecule consisting of crRNA alone or a chimeric RNA of crRNA and tracrRNA that constitutes a nucleic acid sequence-recognizing module in combination with a mutant Cas effector protein is collectively referred to as a "guide RNA". The same also applies when a CRISPR/Cas system without introduction of mutation is used.

While the Cas effector protein to be used in the present invention is not particularly limited as long as it can form a complex with guide RNA and recognize and bind to the target nucleotide sequence in the gene of interest and a protospacer adjacent motif (PAM) adjacent thereto, it is preferably Cas9 (also referred to as Cas9 nuclease) or Cpf1 (also referred to as Cpf1 nuclease). Examples of Cas9 include, but are not limited to, Cas9 derived from *Streptococcus pyogenes* (SpCas9; PAM sequence NGG (N is A, G, T or C, hereinafter the same)), Cas9 derived from *Streptococcus thermophilus* (StCas9; PAM sequence NNAGAAW), Cas9 derived from *Neisseria meningitidis* (MmCas9; PAM sequence NNNNGATT) and the like. Preferred is SpCas9 with less restriction by PAM (substantially 2 bases, and can target theoretically any site in the genome). Examples of the Cpf1 include, but are not limited to, Cpf1 derived from *Francisella novicida* (FnCpf1; PAM sequence NTT), Cpf1 derived from *Acidaminococcus* sp. (AsCpf1; PAM sequence NTTT), Cpf1 derived from Lachnospiraceae bacterium (LbCpf1; PAM sequence NTTT) and the like. As a mutant Cas effector protein (sometimes to be abbreviated as mutant Cas) to be used in the present invention, any of Cas effector protein wherein the cleavage ability of the both strands of the double-stranded DNA is inactivated and one having nickase activity wherein at least one cleavage ability of one strand alone is inactivated can be used. For example, in the case of SpCas9, a D10A mutant in which the 10th Asp residue is converted to an Ala residue and lacking cleavage ability of a strand opposite to the strand forming a complementary strand with a guide RNA (thus having nickase activity for a strand forming complementary strand with guide RNA), or H840A mutant in which the 840th His residue is converted to an Ala residue and lacking cleavage ability of a strand forming a complementary strand to guide RNA (thus having nickase activity for a strand forming complementary strand with guide RNA, or a double mutant thereof (dCas9) can be used. In the case of FnCpf1, a mutant in which the 917th Asp residue is converted to an Ala residue (D917A) or the 1006th Glu residue is converted to an Ala residue (E1006A), and lacking cleavage ability of both strands can be used. As long as at least one of the strands of double-stranded DNA lacks cleavage ability, other mutant Cas can also be used similarly.

A DNA encoding Cas effector protein (including mutant Cas, hereinafter the same) can be cloned by a method similar to the above-mentioned method for a DNA encoding a base excision repair inhibitor, from a cell producing the enzyme. A mutant Cas can be obtained by introducing a mutation to convert an amino acid residue of the site important for the DNA cleavage activity (e.g., 10th Asp residue and 840th His residue for SpCas9, 917th Asp residue and 1006th Glu residue for FnCpf1 and the like, though not limited thereto) to other amino acids, into a DNA encoding cloned Cas, by a site specific mutation induction method known per se.

Alternatively, a DNA encoding Cas effector protein can also be constructed as a DNA with codon usage suitable for expression in a host cell to be used, by a method similar to those mentioned above for a DNA encoding a nucleic acid sequence-recognizing module and a DNA encoding a nucleic acid base converting enzyme, and in a combination of chemical synthesis or PCR method or Gibson Assembly method.

The obtained DNA encoding a Cas effector protein and/or nucleic acid modification enzyme and/or base excision repair inhibitor can be inserted into the downstream of a promoter of an expression vector similar to the one mentioned above, according to the target cell.

On the other hand, a DNA encoding guide RNA can be obtained by designing an oligoDNA sequence linking a coding sequence of crRNA sequence containing a nucleotide sequence complementary to the target nucleotide sequence (to be also referred to as "targeting sequence" in the present specification) (e.g., when FnCpf1 is recruited as Cas effector protein, crRNA containing SEQ ID NO: 1; AAUUUCUACUGUUGUAGAU at the 5'-side of the targeting sequence can be used, and the underlined sequences form base pairs to form a stem-loop structure), or a crRNA coding sequence and, where necessary, a known tracrRNA coding sequence (e.g., as tracrRNA coding sequence when Cas is recruited as Cas9 effector protein, gttttagagctagaaatagcaagttaaaataaggctagtccgttatcaacttgaaaaagtggc accgagtcggtgcttttttt; SEQ ID NO: 2, or gttttagagctagaaatagcaagttaaaataaggctagtccgttatcaacttgaaaaagtggc accgagtcggtggtgctttt; SEQ ID NO: 3) and chemically synthesizing using a DNA/RNA synthesizer.

The "targeted strand" here means a strand forming a hybrid with crRNA of the target nucleotide sequence, and the opposite strand, which becomes single-stranded after hybridization of the targeted strand and crRNA, is referred to as a "non-targeted strand". When the target nucleotide sequence is to be expressed by one of the strands (e.g., when PAM sequence is indicated, when positional relationship of target nucleotide sequence and PAM is shown etc.), it is represented by a sequence of the non-targeted strand.

While the length of the targeting sequence is not particularly limited as long as it can specifically bind to a target nucleotide sequence, for example, it is 15-30 nucleotides, preferably 18-25 nucleotides.

When Cas9 is used as a Cas effector protein, a targeting sequence can be designed, for example, using a guide RNA design website open to public (CRISPR Design Tool, CRISPRdirect etc.) by listing up 20 mer sequences having PAM (e.g., NGG in the case of SpCas9) adjacent to the 3'-side from the CDS sequences of the gene of interest, and selecting a sequence that causes an amino acid change in the protein encoded by the target gene when C within 7 nucleotides from the 5' end thereof toward 3' direction is converted to T. An appropriate sequence can be selected even when a targeting sequence with a length other than 20 mer is used. A candidate sequence having a small number of off-target sites in the host genome of interest can be used as a targeting sequence. When the guide RNA design software to be used does not have a function to search off-target sites in the genome of the host, for example, off-target sites can be searched by applying a Blast search against the genome of the host, for example, 8-12 nucleotides on the 3'-side of the candidate sequence (seed sequence with high discrimination ability of target nucleotide sequence).

While a DNA encoding guide RNA can also be inserted into an expression vector similar to the one mentioned above. As the promoter, pol III system promoter (e.g., SNR6, SNR52, SCR1, RPR1, U3, U6, H1 promoter etc.) and terminator (e.g., polyT m sequence ($T_6$ sequence etc.)) are preferably used.

A DNA encoding guide RNA (crRNA or crRNA-tracrRNA chimera) can be obtained by designing an oligoRNA sequence linking a sequence complementary to the target strand of the target nucleotide sequence and a known tracrRNA sequence (when Cas9 is recruited) or a direct repeat sequence of crRNA (when Cpf1 is recruited) and chemically synthesizing using a DNA/RNA synthesizer.

A DNA or RNA encoding mutant Cas and/or a nucleic acid base converting enzyme etc., guide RNA-tracrRNA or a DNA encoding same can be introduced into a host cell by a method similar to the above, according to the host.

Since conventional artificial nuclease accompanies double-stranded DNA breaks (DSB), inhibition of growth and cell death assumedly caused by disordered cleavage of chromosome (off-target cleavage) occurred by targeting a sequence in the genome. In the present invention, the targeted site is modified not by DNA cleavage but by utilizing a conversion reaction of the substituent on the DNA base (particularly deamination reaction), or a base excision reaction, and a repair mechanism thereafter. Therefore, drastic reduction of toxicity can be realized.

In the method of the present invention, it is also possible to modify the targeted site by using multiple target nucleotide sequences at different positions. Therefore, in one preferable embodiment of the present invention, two or more kinds of nucleic acid sequence-recognizing modules that specifically bind to different target nucleotide sequences can be used. In this case, each one of these nucleic acid sequence-recognizing modules and nucleic acid base converting enzyme etc. form a nucleic acid-modifying enzyme complex. Here, a common nucleic acid base converting enzyme etc. can be used. For example, when CRISPR-Cas system is used as a nucleic acid sequence-recognizing module, a common complex (including fusion protein) of a Cas effector protein and a nucleic acid base converting enzyme etc. is used, and two or more kinds of chimeric RNAs of two or more tracrRNA or each of two or more crRNAs that respectively form a complementary strand with a different target nucleotide sequence are produced and used as guide RNA (crRNA or crRNA-tracrRNA chimera). On the other hand, when zinc finger motif, TAL effector and the like are used as nucleic acid sequence-recognizing modules, for example, a nucleic acid base converting enzyme etc. can be fused with a nucleic acid sequence-recognizing module that specifically binds to a different target nucleotide.

To express the nucleic acid-modifying enzyme complex of the present invention in a host cell, as mentioned above, an expression vector containing a DNA encoding the nucleic acid-modifying enzyme complex is introduced into a host cell. For efficient introduction of mutation, it is desirable to maintain an expression of nucleic acid-modifying enzyme complex of a given level or above for not less than a given period. From such viewpoint, it is certain that the expression vector is incorporated into the host genome. Since continuous expression of the nucleic acid-modifying enzyme complex increases the risk of off-target cleavage, it is preferably removed immediately after achieving modification of the targeted site. Examples of the means for removing DNA incorporated into the host genome include a method using a Cre-loxP system or FLP-FRT system, a method using transposon and the like.

Alternatively, editing of host genome can be efficiently realized while avoiding the risk of off-target cleavage by causing a nucleic acid reaction in a desired stage, and transiently expressing the nucleic acid-modifying enzyme complex of the present invention in a host cell for a period necessary for stabilizing the modification of the targeted site. Those of ordinary skill in the art can appropriately determine a preferable expression induction period based on the culture conditions and the like to be used. The expression induction period of a nucleic acid encoding the nucleic acid-modifying enzyme complex of the present invention may be extended beyond the above-mentioned "period necessary for stabilizing the modification of the targeted site" as long as the host cell is free of side effects.

As a means for transiently expressing the nucleic acid-modifying enzyme complex of the present invention at a desired stage for a desired period, a method including producing a construct (expression vector) containing a nucleic acid (a DNA encoding a guide RNA and a DNA encoding a Cas effector protein and nucleic acid modifying enzyme etc. in the mutant CRISPR-Cas system) encoding the nucleic acid-modifying enzyme complex, in a form capable of controlling the expression period, introducing the construct into a host can be mentioned. The "form capable of controlling the expression period" is specifically, for example, a nucleic acid encoding the nucleic acid-modifying enzyme complex of the present invention placed under regulation of an inducible regulatory region. While the "inducible regulatory region" is not particularly limited, it is, for example, an operon of a temperature sensitive (ts) mutation repressor and an operator regulated thereby. Examples of the ts mutation repressor include, but are not limited to, ts mutation of cI repressor from λphage. In the case of λphage cI repressor (ts), it is linked to an operator to suppress expression of gene in the downstream at not more than 30° C. (e.g., 28° C.). At a high temperature of not less than 37° C. (e.g., 42° C.), it is dissociated from the operator to allow for induction of gene expression. Therefore, the period when the expression of the target gene is suppressed can be minimized by culturing a host cell introduced with a nucleic acid encoding nucleic acid-modifying enzyme complex generally at not more than 30° C., raising the temperature to not less than 37° C. at an appropriate stage, performing culture for a given period to carry out homologous recombination and, after introduction of mutation into the target gene, rapidly lowering the temperature to not more than 30° C. Thus, even when an essential gene for the host cell is targeted, it can be efficiently edited while suppressing the side effects.

When temperature sensitive mutation is utilized, for example, a temperature sensitive mutant of a protein necessary for autonomous replication of a vector is included in a vector containing a DNA encoding the nucleic acid-modifying enzyme complex of the present invention. As a result, autonomous replication becomes impossible rapidly after expression of the nucleic acid-modifying enzyme complex, and the vector naturally falls off during the cell division. Examples of the temperature sensitive mutant protein include, but are not limited to, a temperature sensitive mutant of Rep101 ori necessary for the replication of pSC101 ori. Rep101 ori (ts) acts on pSC101 ori to enable autonomous replication of plasmid at not more than 30° C. (e.g., 28° C.), but loses function at not less than 37° C. (e.g., 42° C.), and plasmid cannot replicate autonomously. Therefore, a combined use with cI repressor (ts) of the above-mentioned λphage simultaneously enables transient expression of the nucleic acid-modifying enzyme complex of the present invention, and removal of the plasmid.

In addition, a DNA encoding the nucleic acid-modifying enzyme complex of the present invention is introduced into a host cell under regulation of inducible promoter (e.g., lac promoter (induced by IPTG), cspA promoter (induced by cold shock), araBAD promoter (induced by arabinose) etc.), the inducing substance is added to the medium (or removed from the medium) at an appropriate stage to induce expression of the nucleic acid-modifying enzyme complex, culture is performed for a given period to carry out a nucleic acid modification reaction and, introduction of mutation into the target gene, transient expression of the nucleic acid-modifying enzyme complex can be realized.

The present invention is explained in the following by referring to Examples, which are not to be construed as limitative.

EXAMPLE

<Cell Line, Culture, Transformation, and Expression Induction of Budding Yeast>

Budding yeast *Saccharomyces cerevisiae* BY4741 strain (requiring leucine and uracil) was cultured in a standard YPDA medium or SD medium with a Dropout composition meeting the auxotrophicity. The culture was performed in static culture on an agar plate or in agitating culture in a liquid medium between 25° C. and 30° C. Transformation was performed by a lithium acetate method, and selection was made in SD medium showing appropriate auxotrophicity. For expression induction by galactose, after preculture overnight in an appropriate SD medium, culture in SR medium overnight with carbon source changed from 2% glucose to 2% raffinose, and further culture in SGal medium for 3 hr to about two nights with carbon source changed to 0.2% galactose were conducted for expression induction.

For the measurement of the number of surviving cells and Can1 mutation rate, a cell suspension was appropriately diluted, and applied to SD plate medium and SD-Arg+60 mg/l Canavanine plate medium or SD+300 mg/l Canavanine plate medium, and the number of colonies that emerge 3 days later was counted as the number of surviving cells. Using the number of surviving colonies in SD plate as the total number of cells, and the number of surviving colonies on Canavanine plate as the number of resistant mutant strains, the mutation rate was calculated and evaluated. The site of mutation was identified by amplifying DNA fragments containing the target gene region of each strain by a colony PCR method, followed by DNA sequencing and an alignment analysis based on the sequence of *Saccharomyces* Genome Database (www.yeastgenome.org/).

<Cell Line, Culture, Expression Induction of Animal Cell>

Cells from human fetal kidney (HEK293T cells) were cultured in a DME-glutamax medium (Thermo Fisher Scientific) added with 10 μg/mL puromycin (Life Technologies) and 10% fetal bovine serum (FBS) (Biosera, Nuaille, France) under 37° C., 5% $CO_2$ conditions. The cells were recovered using 5% trypsin. HEK293T cells preserved in a deep freezer were dissolved in a water bath at 37° C. and seeded in a 75 T-flask at $5\times10^6$ cells. After culturing for 1-3 days, the cells were recovered and seeded in each well of a 24 well plate at $0.5\times10^5$ cells/well. After culturing for 1-3 days, 60-80% confluent cells in each well were transfected with each 500 ng/well of the following plasmid (effector plasmid and reporter plasmid) (total 1 μg/well), 200 nM donor DNA, 1.5 μl FugeneHD (Promega). The donor DNA used in each Example is shown in Table 1. After transfection for 72 hr, the cells were recovered, and the fluorescence of iRFP and EGFP was detected using FACS. The recombinant efficiency (%) was calculated from the number of detected cells by the following formula.

TABLE 1

| | oligo sequence (5'-3') | SEQ ID NO: | name in Example 5 | name in Example 6 | name in Example 7 |
|---|---|---|---|---|---|
| Fw1 (70 b) | gcgCTACCGGACTCAGATCTACCggcccagttggaatgtaggTGGTGAGCAAGGGCGAGGaGCTGTTCAC | 32 | Fw1 | | |
| Fw2 (70 b) | gcgCTACCGGACTCAGATCTACCggcccagttggaatgtagaTGGTGAGCAAGGGCGAGGaGCTGTTCAC | 33 | Fw2 | | |
| Fw3 (70 b) | gcgCTACCGGACTCAGATCTACgggcccagttggaatgtagaTGGTGAGCAAGGGCGAGGaGCTGTTCAC | 34 | Fw3 | | Fw1 |
| Rv1 (70 b) | GTGAACAGCtCCTCGCCCTTGCTCACCAcctacattccaactgggccGGTAGATCTGAGTCCGGTAGcgc | 35 | | | |
| Rv2 (70 b) | GTGAACAGCtCCTCGCCCTTGCTCACCAtctacattccaactgggccGGTAGATCTGAGTCCGGTAGcgc | 36 | | | |
| Rv3 (70 b) | GTGAACAGCtCCTCGCCCTTGCTCACCAtctacattccaactgggcccGTAGATCTGAGTCCGGTAGcgc | 37 | | | |
| Fw70b shifted to left 15b | CCGTCAGATCCGCTAGCGCTACCGGACTCAGATCTACCggcccagttggaatgtagaTGGTGAGCAAGGG | 38 | | | Fw2 |
| Fw70b shifted to right 15b | GATCTACCggcccagttggaatgtagaTGGTGAGCAAGGGCGAGGaGCTGTTCACCGGGGTGGTGCCCAT | 39 | | | Fw3 |
| Fw50b center | ACTCAGATCTACCggcccagttggaatgtagaTGGTGAGCAAGGGCGAGG | 40 | | Fw | Fw4 |
| Rv50b center | CCTCGCCCTTGCTCACCAtctacattccaactgggccGGTAGATCTGAGT | 41 | | Rv | |

$$\text{homologous recombination rate (\%)} = \frac{iRFP \text{ and } GFP \text{ double positive cell number}}{iRFP \text{ positive cell number}} \times 100$$

<Nucleic Acid Manipulation>

DNA was processed or constructed by any of PCR method, restriction enzyme treatment, ligation, Gibson Assembly method, and artificial chemical synthesis. For plasmid, as a yeast-*Escherichia coli* shuttle vector, pRS415 for leucine selection and pRS426 for uracil selection were used as the backbone. Plasmid was amplified by *Escherichia coli* line XL-10 gold or DH5α, and introduced into yeast by the lithium acetate method.

<Construction of Budding Yeast Construct>

Sequences of homology arm, guide RNA, insertion sequence and the like were designed by referring to yeast genome database (www.yeastgenome.org/). Vector was constructed according to the method described in Nishida K. et al., Science 16:353(6305) (2016) doi: 10.1126/science.aaf8729. 1×gRNA vector corresponds to a vector in which the 5871st-5890th base sequence of the sequence shown in SEQ ID NO: 15 is substituted by a complementary sequence of L86 or M4 target nucleotide sequence. 2×gRNA vector corresponds to a vector in which the 2638th-2657th base sequence of the sequence shown in SEQ ID NO: 16 is substituted by a complementary sequence of a target nucleotide sequence of any of L86, L87, L88, L93 and R90, and the 6293rd-6312nd base sequence of SEQ ID NO: 16 is substituted by a complementary sequence of a target nucleotide sequence of any of L87, R89, R90, R91 and R92. The above-mentioned target nucleotides are as follows.

```
                                   (SEQ ID NO: 17)
L86:        CGAACAGAGTAAACCGAATC

                                   (SEQ ID NO: 18)
L87:        AGCACTATCAAGGCTAATAA

                                   (SEQ ID NO: 19)
L88:        GCGAACTTGAAGAATAACCA

                                   (SEQ ID NO: 20)
R89:        TCACCTAACTCAGACATTAT

                                   (SEQ ID NO: 21)
R90:        TTGCTGATTCTATTTACAAA

                                   (SEQ ID NO: 22)
R91:        GCAAACTCTATTCTTGGTGC

                                   (SEQ ID NO: 23)
R92:        ACCAGAGTATCATCCATGTC

                                   (SEQ ID NO: 24)
L93:        AATTCGGACACTTTAGGGTT

                                   (SEQ ID NO: 25)
M4:         AGATATTATACCTGGACCCC
```

<Construction of Animal Cell Construct>

The pcDNA3.1 vector backbone and the respective sequences of CMV, PmCDA1, Cas9, H1, sgRNA are derived from a paper by Nishida et al. 2016. Each mutation was introduced by the PCR method. EF1, iRFP and mEGFP segments were generated by artificial gene synthesis. The segments were inserted and substituted by Gibson assembly or ligation reaction.

The sequences of the produced vector SY4 (H1_sgRNA, CMV_mEGFP) (reporter plasmid), vector SY45 (CMV_Cas9-PmCDA1, EF1_iRFP) and vector SY45 (CMV_Cas9, EF1_iRFP) are respectively shown in SEQ ID NOs: 42-44. Vector SY45 (CMV_nCas9(D10A)-PmCDA1, EF1_iRFP) corresponds to one in which the 770th-772nd bases of sequence number 43 are substituted by gct. Vector SY45 (CMV_nCas9(H840A)-PmCDA1, EF1_iRFP) corresponds to one in which the 3260th-3262nd bases of sequence number 43 are substituted by gct. Vector SY45 (CMV_dCas9-PmCDA1, EF1_iRFP) corresponds to one in which the 770th-772nd bases of sequence number 43 are substituted by gct, and the 3260th-3262nd bases are substituted by gct. Vector SY45 (CMV_nCas9(D10A), EF1_iRFP) corresponds to one in which the 3724th-3726th bases of sequence number 44 are substituted by gct. Vector SY45 (CMV_nCas9(H840A), EF1_iRFP) corresponds to one in which the 6214th-6216th bases of sequence number 44 are substituted by gct. Vector SY45 (CMV_dCas9, EF1_iRFP) corresponds to one in which the 3724th-3726th bases of sequence number 44 are substituted by gct, and the 6214th-6216th bases are substituted by gct.

<Sequencing of DNA in Cell>

The iRFP-positive cells were separated by FACS, the genomic DNA and the introduced plasmid DNA were extracted, and the following samples were prepared and subjected to PCR under the following conditions to amplify the targeted site.

Sample Preparation:

| | |
|---|---|
| gDNA | 1 μL |
| primer | each 1 μL |
| rTaq 10x Buffer | 5 μL |
| 25 mM $MgCl_2$ | 3 μL |
| 2 mM dNTP | 5 μL |
| rTaq (TOYOBO) | 0.5 μL |
| $ddH_2O$ | 33.5 μL |
| total | 50 μL |

PCR conditions: maintained at 94° C. for 2 min, a cycle of 94° C. for 45 sec, 55° C. for 45 sec and 72° C. for 1 min 30 sec was performed 33 times, and finally maintained at 72° C. for 5 min.

As amplification primers, the following SY157 and SY182 were used. The size of the amplification product was 1554 bp.

```
                                   (SEQ ID NO: 47)
SY157:  TTCTGCTTGTCGGCCATGAT

                                   (SEQ ID NO: 48)
SY182:  AGGCAAGGCTTGACCGACAATT
```

The amplified product was cut out and purified using Fastgene. Then, TA cloning was performed with each purified product using pGEM-t easy vector, and *Escherichia coli* (JM109) was transformed with the vector. Then, 24 colonies were selected from each sample (with blue-white selection), and the plasmid DNA was purified by Mini prep (using Fastgene).

Then, the following sequencing mixture was prepared and outsourced to Genewiz to obtain sequence information.

| | |
|---|---|
| each sample | 2.5 μL |
| primer SY157 (10 pmol/μL) | 2.5 μL |
| $ddH_2O$ | 10 μL |
| total | 15 μL |

Finally, the obtained sequence information was aligned using Snapgene.

Example 1: Insertion of Insertion Sequence into Targeted Site Using dCas9-CDA or nCas9-CDA and Donor DNA The budding yeast strain BY4741 was subjected to double transformation with plasmid vector 1525 (in SEQ ID NO: 4, 6036th base is g, 6037th base is c) or 1526 (in SEQ ID NO: 4, 6036th base is c, 6037th base is a), and 1059 (SEQ ID NO: 5) or 1149 (corresponds to vector in which the 3890th-3909th base sequence of sequence SEQ ID NO: 5 is substituted by TCCAATAACGGAATCCAACT (SEQ ID NO: 6)), and the strain was selected using auxotrophic medium (SD-Leu-Ura). The cells were cultured overnight in S-Leu-Ura 2% raffinose medium. They were diluted 1/32 in S-Leu-Ura 2% raffinose+0.02% galactose medium and cultured overnight at 30° C. They were spotted at 10-fold dilution in SD-Ura-Leu and SD-Ura-Leu+Canavanine plate. Two days later, Canavanine resistant colonies were subjected to sequence analysis. As a result, insertion of the mutation into the targeted site was confirmed (FIG. 2).

Example 2: Construction of Recombinant Evaluation System

Plasmid vector 1548 (SEQ ID NO: 7) was treated with SmaI/HpaI to produce a DNA fragment, BY4741 strain was transformed with the fragment and selected in SD-Ura medium. Sequence analysis confirmed integration into the Ade1 region.

Figure 4:
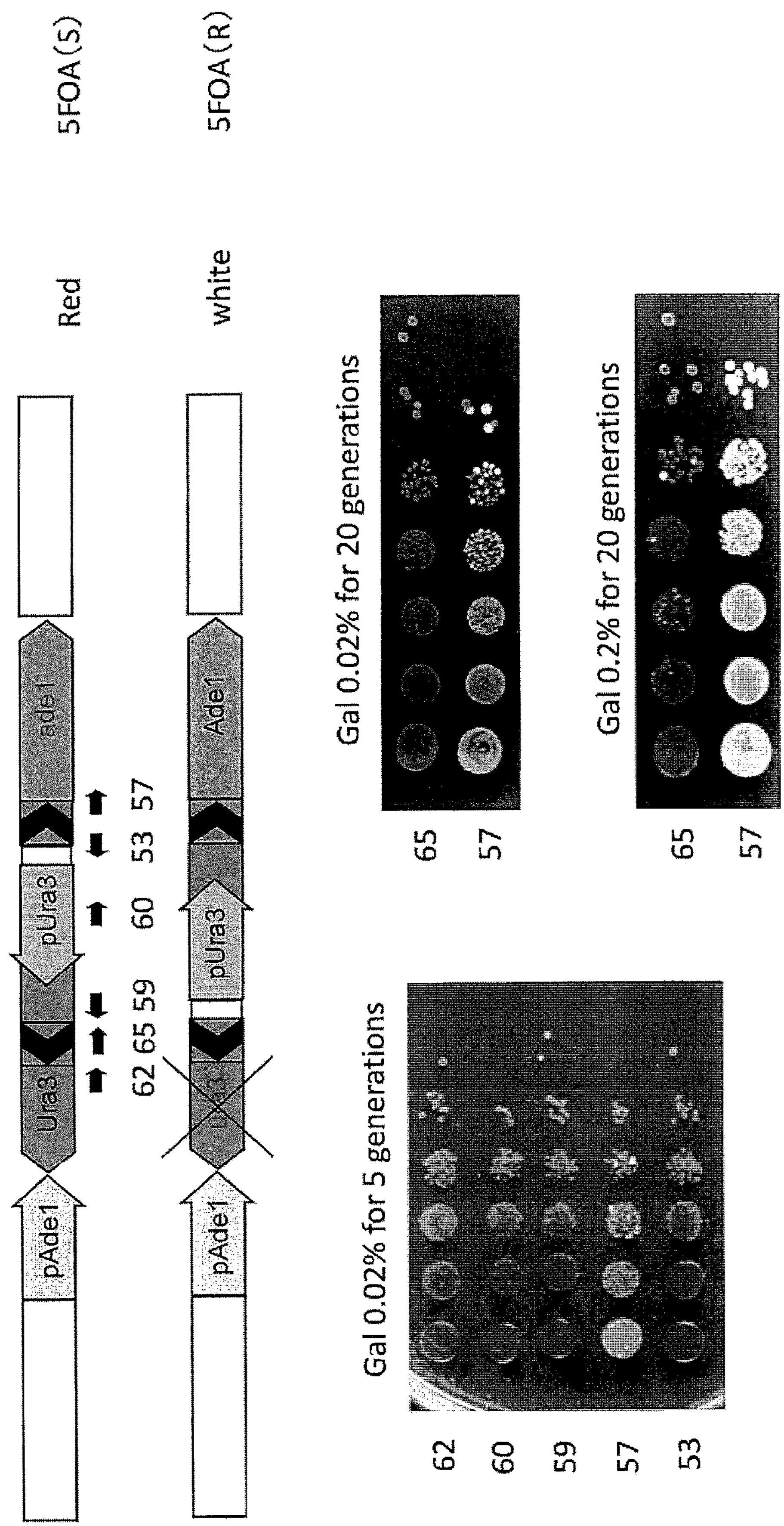
FIG. 4 shows the results of a demonstration experiment of a recombination reaction using the recombination evaluation system of FIG. 3. Plasmid vector (hereinafter sometimes to be abbreviated as "vector") 1553: nCas9-CDA_UraAde target 2 (target nucleotide sequence: cctttagcggcttaactgtg (SEQ ID NO: 9)); vector 1557: nCas9-CDA_UraAde target 6 (target nucleotide sequence: ggcccaggtattgttagcgg (SEQ ID NO: 10)), vector 1559: nCas9-CDA_UraAde target 8 (target nucleotide sequence: ttggcggataatgcctttag (SEQ ID NO: 11)); vector 1560: nCas9-CDA_UraAde target 9 (target nucleotide sequence: tgcagttgggttaagaatac (SEQ ID NO: 12)), vector 1562: nCas9-CDA_UraAde target 11 (target nucleotide sequence: gctaacatcaaaaggcctct (SEQ ID NO: 13)); vector 1565: dCas9-CDA_UraAde target 3 (target nucleotide sequence: ttggcggataatgcctttag (SEQ ID NO: 14)). The above-mentioned vectors (1553, 1557, 1559, 1560, 1562, 1565) correspond to vectors in which the nucleotide sequences at the 3890th to the 3909th position in the sequence of vector 1059 (SEQ ID NO: 5) have been substituted with the above-mentioned target nucleotide sequences. The last two digits of the vector number correspond to the numbers of the targeted sites in FIG. 4.
Figure 5:
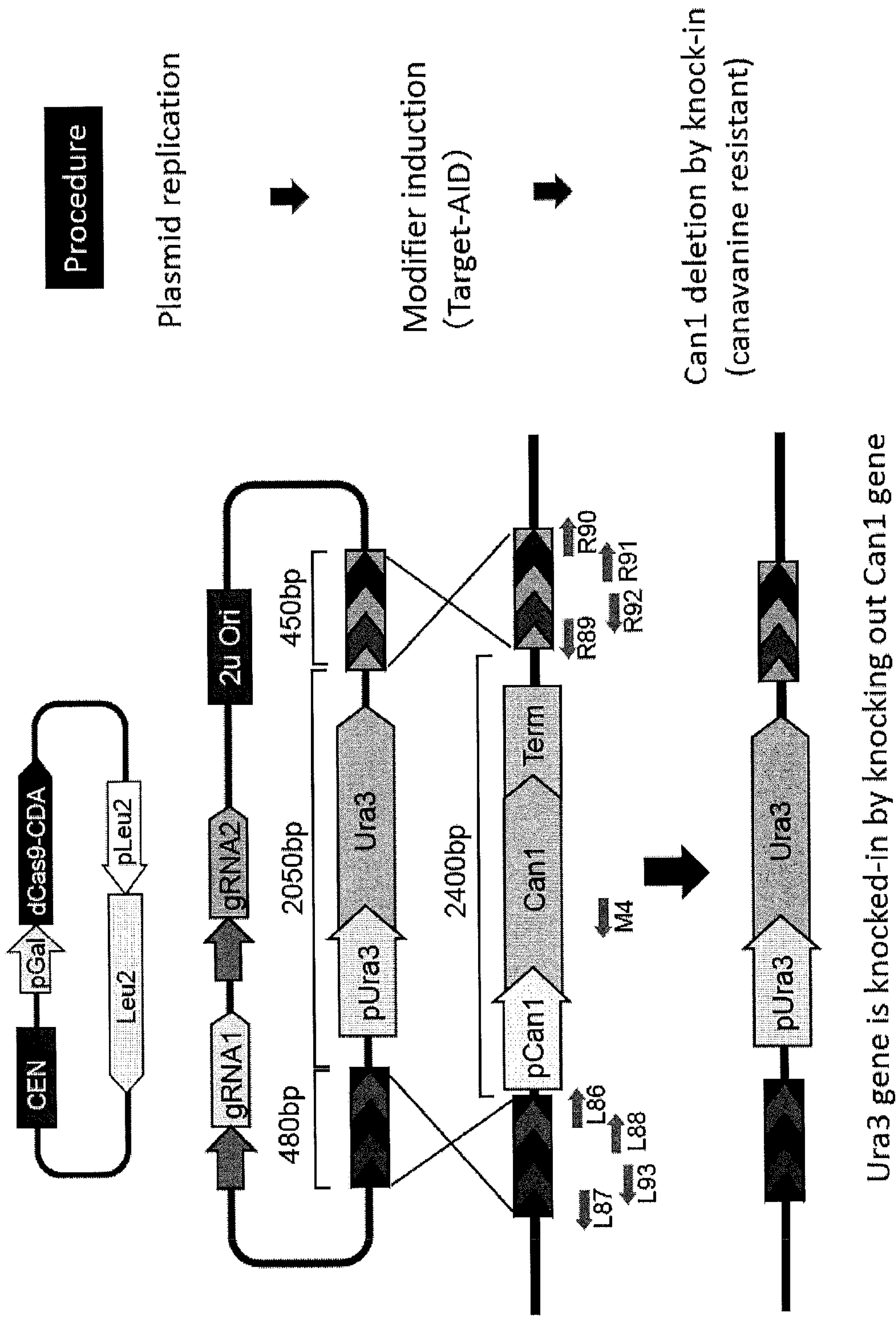
FIG. 5 shows a schematic diagram of a knock-in or knock-out method using the DNA modification method of the present invention.

Example 3: Demonstration Experiment of Recombination Reaction Using Recombinant Evaluation System Either of the above-mentioned plasmid vectors was transformed into a demonstration experiment strain and selected using SD-Leu-Ura medium. The cells were cultured overnight in S-Leu-Ura 2% raffinose medium. They were diluted 1/32 with S-Leu 2% raffinose+0.02% (or 0.2%) galactose medium, cultured overnight at 30° C. resulting in 5 generations. For generating 20 generations, 1/32 dilution was repeated 4 times in total. They were spotted on SD-Leu plate at 10-fold dilution, and two days later, the number and color of the colonies were evaluated. As a result, colonies with restored Adel function and white appearance were frequently appeared, indicating that homologous recombination was induced at the targeted site by the method of the present invention (FIG. 4).

Example 4: Demonstration Experiment of Knock-in or Knock-Out by the Present Invention The budding yeast strain BY4741 was double-transformed with the plasmid vector 1251 (SEQ ID NO: 8) and the 2×gRNA vector, and selected using an auxotrophic medium (SD-Leu-Ura). The cells were cultured overnight in S-Leu-Ura 2% raffinose medium. The cells were diluted 1/32 with S-Leu-Ura 2% raffinose+0.2% galactose medium and cultured overnight at 30° C. They were spotted at 10-fold dilution in SD-Ura-Leu and SD-Ura-Leu (+Canavanine) plates. Two days later, Canavanine resistance colony was subjected to sequence analysis. As a result, knock-in was realized with high efficiency by the method of the present invention (FIG. 6).

Example 5: Demonstration Experiment of Recombinant Reaction in Animal Cell

Figure 7:
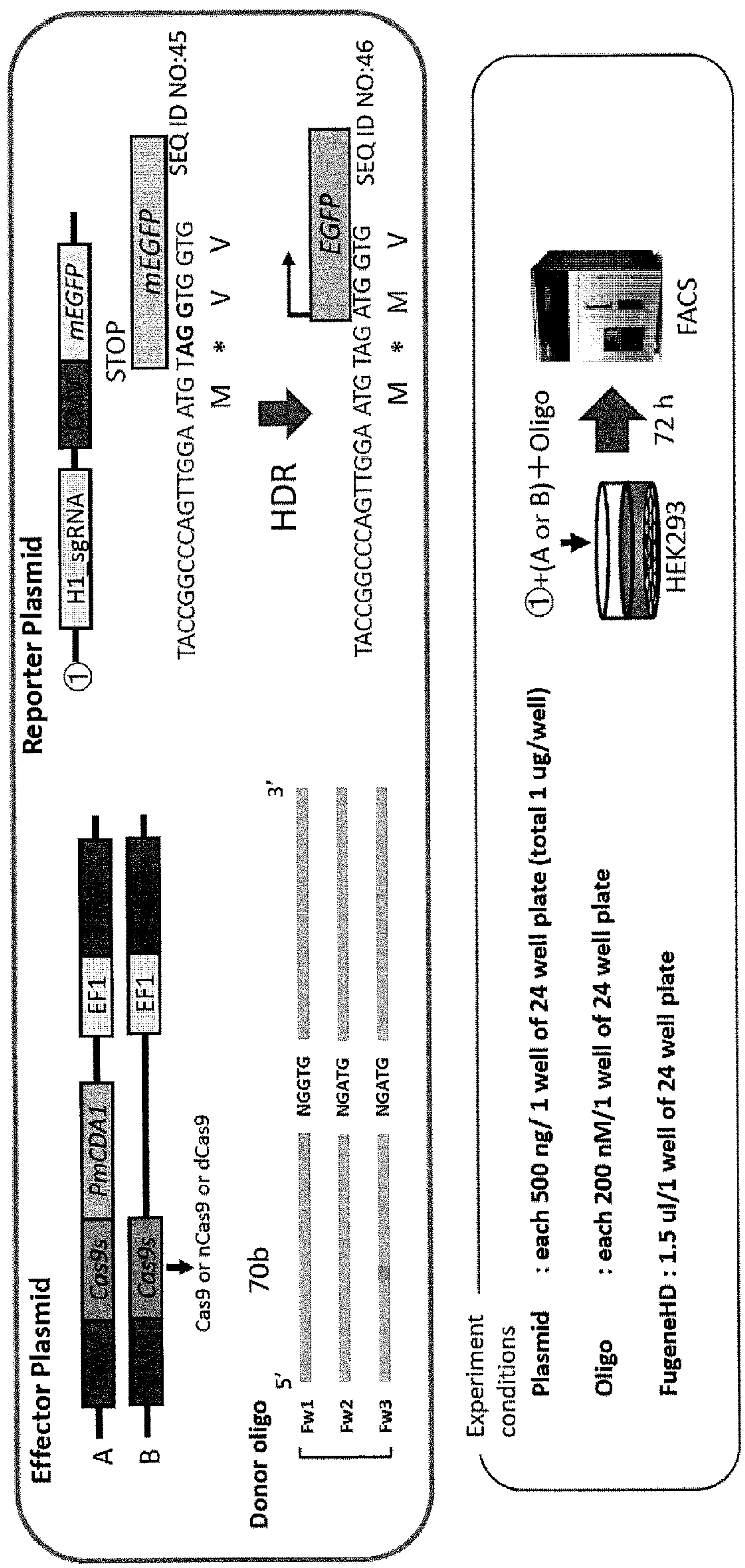
FIG. 7 shows a schematic diagram and experimental conditions of the evaluation system of recombination performed in Example 5 using animal cells.

Using a single-stranded oligo DNA (70 bases in length) (Table 1) as a donor DNA, whether or not a recombination reaction occurs in animal cells (HEK293T cells) was verified. A schematic drawing of the experiment is shown in FIG. 7. Vector SY4 (H1_sgRNA, CMV_mEGFP) was used as reporter plasmid and vector SY45 (CMV_Cas9-PmCDA1, EF1_iRFP), vector SY45 (CMV_nCas9(D10A)-PmCDA1, EF1_iRFP), vector SY45 (CMV_nCas9 (H840A)-PmCDA1, EF1_iRFP), vector SY45 (CMV_dCas9-PmCDA1, EF1_iRFP), vector SY45 (CMV_Cas9, EF1_iRFP), vector SY45 (CMV_nCas9 (D10A), EF1_iRFP), vector SY45 (CMV_nCas9(H840A), EF1_iRFP) or vector SY45 (CMV_dCas9, EF1_iRFP) was used as an effector plasmid. When Fw2 or Fw3 is used as a donor DNA and when homologous recombination is successfully performed, the initiation codon is generated in the sequence encoding EGFP, resulting in the expression of EGFP. Fw1 is a donor DNA designed to prevent occurrence of an initiation codon in a sequence encoding EGFP even when homologous recombination occurs, and was used as a negative control. Fw3 is a homologous aim of Fw2 in which one base is substituted (c→g), and was used to verify whether homologous recombination occurs even when the homology arm is not completely homologous to the adjacent region of the targeted site and whether mutations at a plurality of different locations can be introduced.

Figure 8:
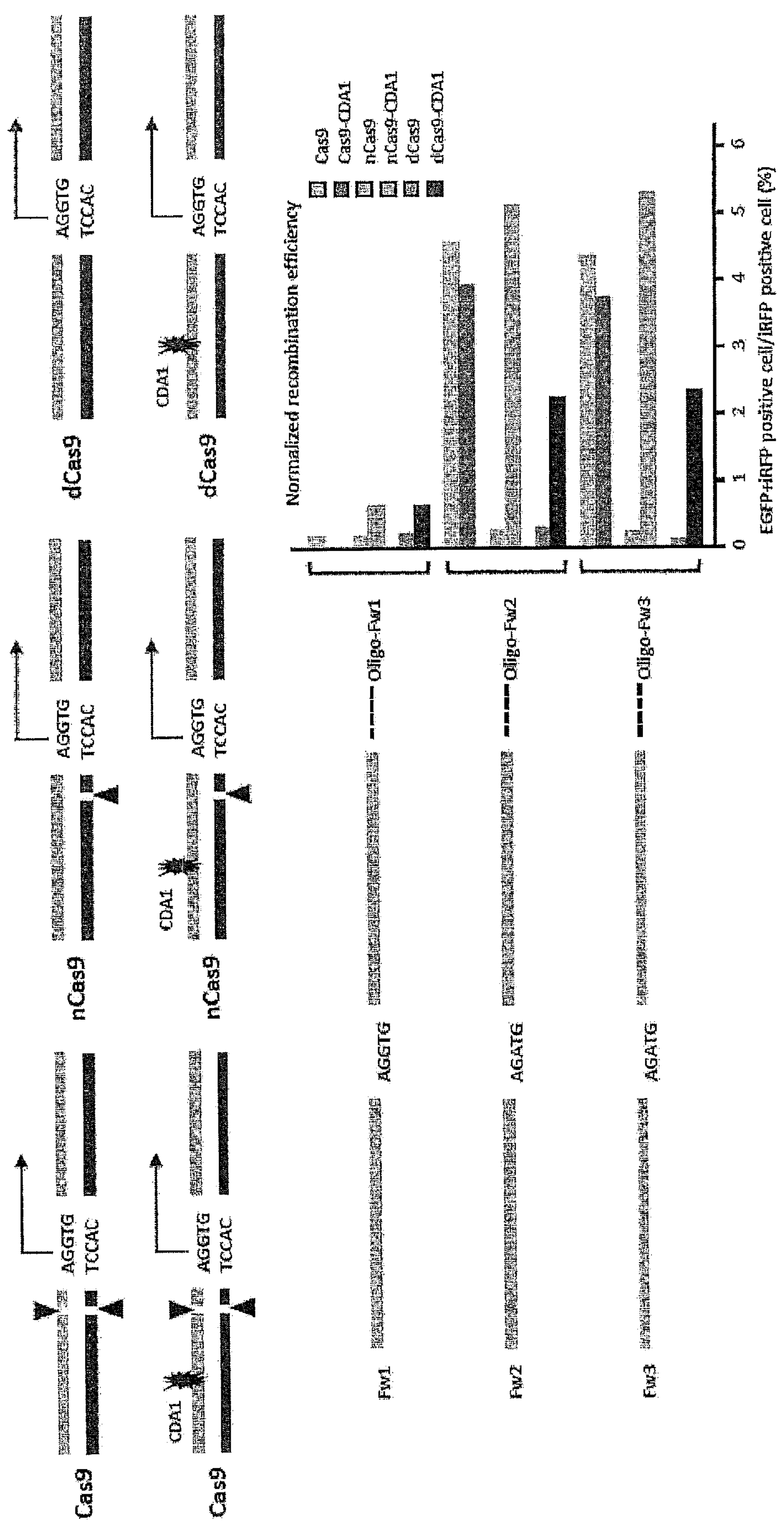
FIG. 8 shows the results of a demonstration experiment of a recombination reaction using the recombination evaluation system of FIG. 7. The horizontal axis of the graph shows homologous recombination rate (%).

The results are shown in FIG. 8. It was shown that when nCas9-pmCDA1 was used, the homologous recombination efficiency was higher than when nCas9 was used, and the homologous recombination efficiency was equal to or higher than that when Cas9 was used. In addition, significant homologous recombination was observed even when dCas9-pmCDA1 was used. There was no significant difference in the homologous recombination rate between when Fw2 was used as the donor DNA and when Fw3 was used as the donor DNA.

Figure 9:
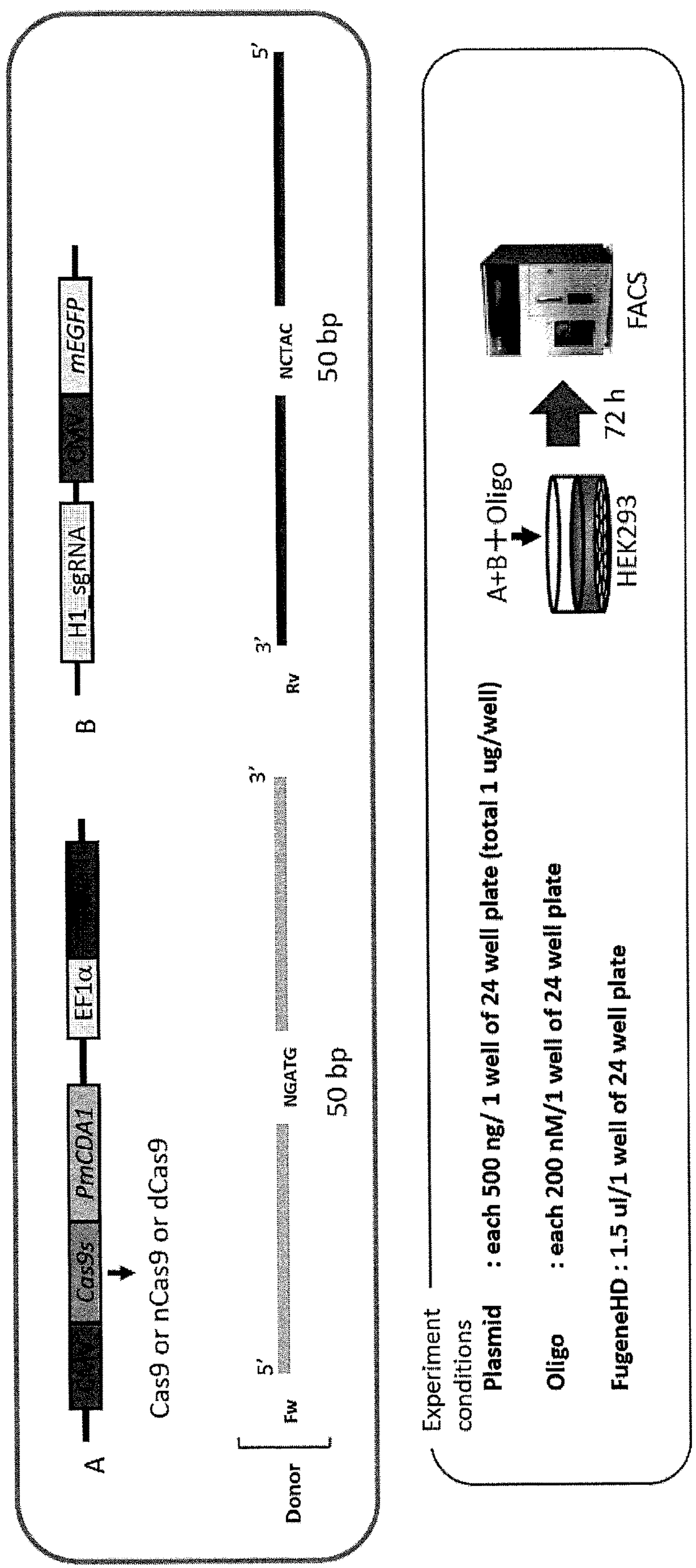
FIG. 9 shows a schematic diagram and experimental conditions of the evaluation system of recombination performed in Example 6 using animal cells.

Example 6: Verification of Influence of Base Number of Donor DNA, and Kind of Complementary Strand (Forward (Fw) or Reverse (Rv)) on Homologous Recombination Reaction Using a single-stranded oligo DNA (50 bases in length) (Table 1) as a donor DNA, whether or not a recombination reaction occurs in animal cells (HEK293T cells) was verified. A schematic drawing of the experiment is shown in FIG. 9. Vector SY4 (H1_sgRNA, CMV_mEGFP) was used as a reporter plasmid and vector SY45 (CMV_nCas9 (D10A))-PmCDA1, EF1_iRFP) or vector SY45 (CMV_nCas9(H840A))-PmCDA1 was used as an effector plasmid.

Figure 10:
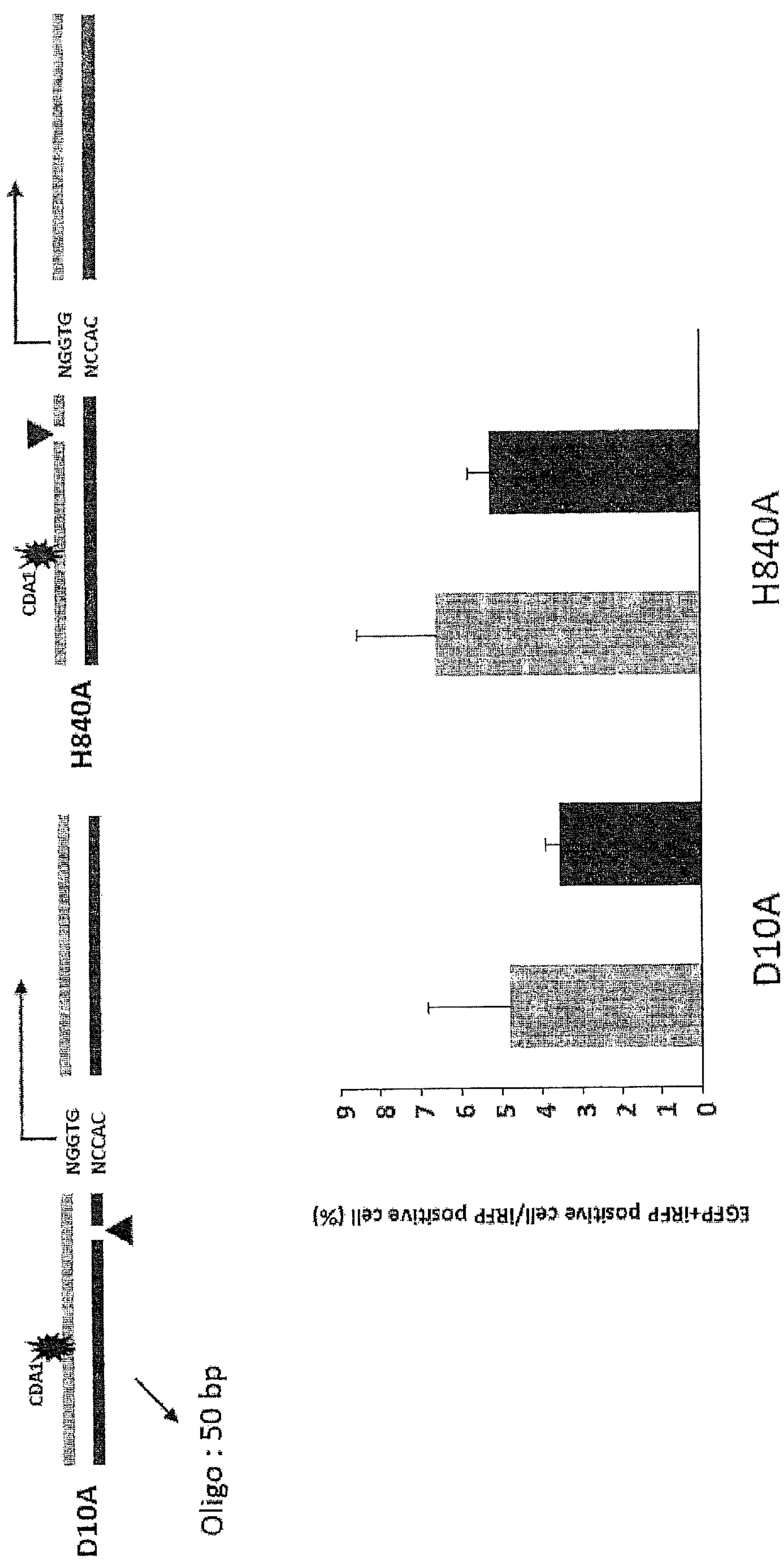
FIG. 10 shows the results of a demonstration experiment of a recombination reaction using the recombination evaluation system of FIG. 9. The vertical axis of the graph shows homologous recombination rate (%).

The results are shown in FIG. 10. It was shown that homologous recombination is possible even with a single-stranded oligo DNA having 50 bases in length, homologous recombination is possible with both complementary strands Fw and Rv, and that homologous recombination is possible with both versions of nCas9 of nCas9 (D10A) and nCas9 (H840A).

Example 7: Verification of Homology Arm of Donor DNA

Figure 11:
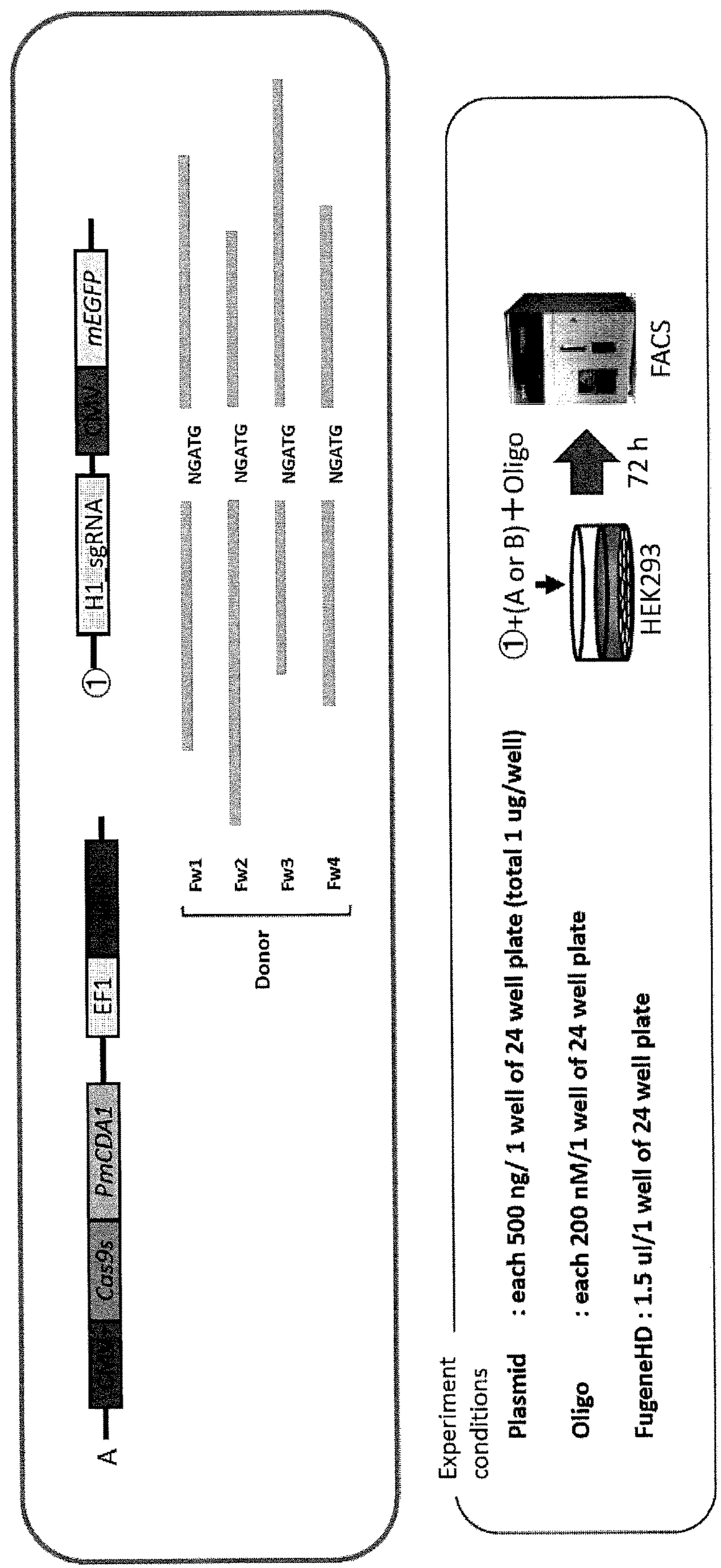
FIG. 11 shows a schematic diagram and experimental conditions of the evaluation system of recombination performed in Example 7 using animal cells.

Using a donor DNA having a homology arm for a different homologous region (Table 1), variation in the efficiency of homologous recombination reaction due to homologous region was verified. A schematic drawing of the experiment is shown in FIG. 11. Vector SY4 (H1_sgRNA, CMV_mEGFP) was used as a reporter plasmid and vector SY45 (CMV_nCas9(D10A))-PmCDA1, EF1 _iRFP) or vector SY45 (CMV_nCas9(H840A))-PmCDA1 was used as an effector plasmid.

Figure 12:
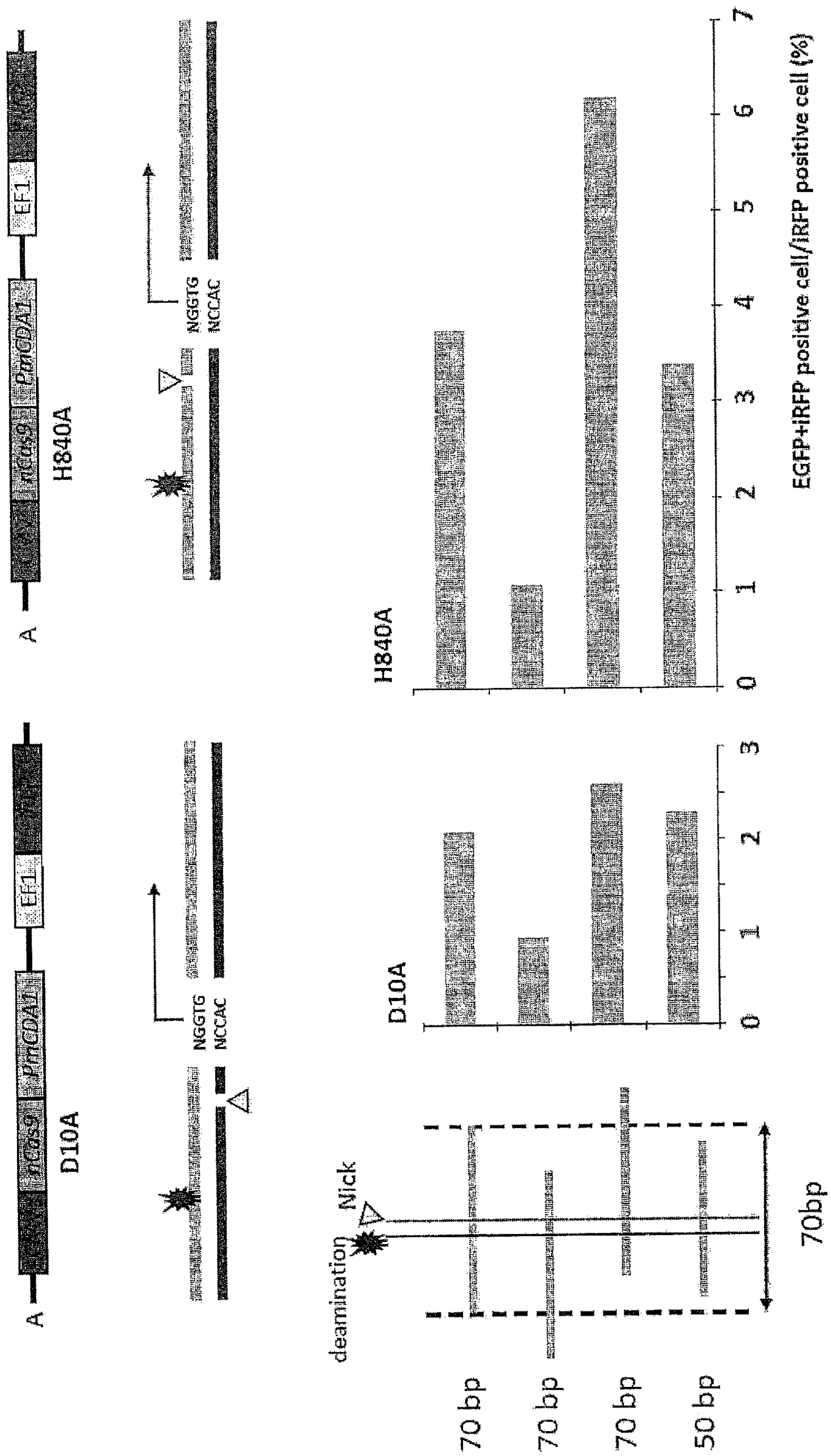
FIG. 12 shows the results of a demonstration experiment of a recombination reaction using the recombination evaluation system of FIG. 11. The horizontal axis of the graph shows homologous recombination rate (%).

The results are shown in FIG. 12. It was shown that the efficiency of homologous recombination is improved by designing donor DNA such that when the site where a nick is generated or the deaminase site of PmCDA1 in the homologous region is considered as the center, the homology arm on the 3'-side of the region would be longer than the homology arm on the 5'-side.

Example 8: Verification of Modification of DNA of Mammalian Cell

Using the same gRNA and donor DNA as in the experiment using Fw2 in Example 5, modification of DNA was verified. The results are shown in the following Table 2. It was demonstrated that when nCas9(D10A)-PmCDA1 and nCas9(H840A)-PmCDA1 were used, the occurrence of Indel, a by-product, is remarkably suppressed compared to the use of Cas9, that is, cytotoxicity is reduced. The term “DNA” used in this Example includes both genomic DNA and plasmid DNA.

TABLE 2

| vector | SEQ success/failure | Indel | Substitution |
|---|---|---|---|
| nCas9 (D10A) | 23/24 | 0/23 | 1/23 |
| Cas9 | 22/24 | 5/22 | 0/22 |
| nCas9 (D10A)-CDA1 | 23/24 | 1/23 | 0/23 |
| nCas9 (H840A)-CDA1 | 22/24 | 0/22 | 3/22 |

Substitution in this study shows base substitution seen in the target sequence of gRNA.

Mutation such as base substitution C→T assumed to have involvement in the action of CDA1 is not found.

From the above, when nCas9-CDA is used, the efficiency of homologous recombination is at least as high as that using Cas9, and it avoids generating Indel as a by-product and high cytotoxicity that occurs when using Cas9. Therefore, a method using nCas9-CDA can be more beneficial and useful than the conventional method. Furthermore, nCas9-CDA can achieve higher efficiency than nCas9 for the purpose of avoiding the above-mentioned problem that occurs when using Cas9.

This application is based on Japanese Patent Application No. 2018-059073 filed in Japan (filing date: Mar. 26, 2018), the contents of which are incorporated in full herein.

INDUSTRIAL APPLICABILITY

The present invention provides a novel DNA modification technique using a nucleic acid base converting enzyme such as deaminase and the like or DNA glycosylase, wherein the technique is not limited by the type of mutation that can be introduced or the site of mutation, can switch the direction and combination of genes, and can knock-in gene segments. Since the DNA modification technique of the present invention can modify the targeted site without cleaving the double-stranded DNA, unexpected rearrangement and toxicity accompanying the cleavage are suppressed, and the targeted site can be modified much more efficiently compared to the conventional methods, it is extremely useful.

The invention claimed is:

1. A method for modifying a targeted site of a double-stranded DNA of a cell, comprising a step of bringing a complex in which a nucleic acid sequence-recognizing module that specifically binds to a selected target nucleotide sequence in a double-stranded DNA and a nucleic acid base converting enzyme or DNA glycosylase are linked, and a donor DNA containing an insertion sequence into contact with said double-stranded DNA, to substitute the targeted site with the insertion sequence, or to insert the insertion sequence into said targeted site, without cleaving at least one strand of said double-stranded DNA in the targeted site.

2. The method according to claim 1, wherein the donor DNA comprises a sequence homologous to a region adjacent to the targeted site.

3. The method according to claim 1, wherein the nucleic acid sequence-recognizing module is selected from the group consisting of a CRISPR-Cas system in which at least one DNA cleavage ability of Cas effector protein is inactivated, a zinc finger motif, a TAL effector and a PPR motif, wherein the Cas effector protein is Cas9 or Cpf1.

4. The method according to claim 3, wherein the nucleic acid sequence-recognizing module is a CRISPR-Cas system in which only one of the two DNA cleavage abilities of the Cas effector protein is inactivated.

5. The method according to claim 3, wherein the nucleic acid sequence-recognizing module is a CRISPR-Cas system in which both DNA cleavage abilities of the Cas effector protein are inactivated.

6. The method according to claim 1, wherein the nucleic acid base converting enzyme is a deaminase.

7. The method according to claim 6, wherein the deaminase is cytidine deaminase.

8. The method according to claim 7, wherein the cytidine deaminase is PmCDA1.

9. The method according to claim 1, wherein the double-stranded DNA is contacted with the complex by introducing a nucleic acid encoding the complex into the cell.

10. The method according to claim 1, wherein the cell is a prokaryotic cell or a eukaryotic cell.

11. The method according to claim 10, wherein the cell is a microbial cell.

12. The method according to claim 10, wherein the cell is a plant cell, an insect cell or an animal cell.

13. The method according to claim 12, wherein the animal cell is a vertebrate cell.

14. The method according to claim 13, wherein the vertebrate cell is a mammalian cell.

* * * * *